(12) United States Patent
Zhang et al.

(10) Patent No.: US 9,938,502 B2
(45) Date of Patent: Apr. 10, 2018

(54) TISSUE-SPECIFIC EXTRACELLULAR MATRIX WITH OR WITHOUT TISSUE PROTEIN COMPONENTS FOR CELL CULTURE

(75) Inventors: Yuanyuan Zhang, Winston Salem, NC (US); Shay Soker, Greensboro, NC (US); Anthony Atala, Winston Salem, NC (US); Aleksander Skardal, Clemmons, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 586 days.

(21) Appl. No.: 13/882,429

(22) PCT Filed: Nov. 4, 2011

(86) PCT No.: PCT/US2011/059349
§ 371 (c)(1),
(2), (4) Date: Jul. 17, 2013

(87) PCT Pub. No.: WO2012/064606
PCT Pub. Date: May 18, 2012

(65) Prior Publication Data
US 2013/0288375 A1    Oct. 31, 2013

Related U.S. Application Data

(60) Provisional application No. 61/412,193, filed on Nov. 10, 2010.

(51) Int. Cl.
*C12N 5/00* (2006.01)
*C12N 5/071* (2010.01)

(52) U.S. Cl.
CPC ......... *C12N 5/0671* (2013.01); *C12N 5/0068* (2013.01); *C12N 2513/00* (2013.01); *C12N 2533/54* (2013.01); *C12N 2533/80* (2013.01); *C12N 2533/90* (2013.01)

(58) Field of Classification Search
None
See application file for complete search history.

(56) References Cited

U.S. PATENT DOCUMENTS

| 2006/0121606 A1* | 6/2006 | Ito ................. C12N 5/0062 435/325 |
| 2007/0269476 A1 | 11/2007 | Voytik-Harbin et al. |
| 2008/0194010 A1 | 8/2008 | Liu |
| 2010/0093077 A1 | 4/2010 | McClelland et al. |

OTHER PUBLICATIONS

Liu et al., "Optimization of a natural collagen scaffold to aid cell-matrix penetration for urologic tissue engineering." 2009, Biomaterials, 30:3865-73.
McClelland et al., "Gradients in the liver's extracellular matrix chemistry from periportal to pericentral zones: influence on human hepatic progenitors." 2008, Tissue Eng Part A, 14:59-70.
Wu et al., "Human urine-derived stem cells seeded in a modified 3D porous small intestinal submucosa scaffold for urethral tissue engineering." 2011, Biomaterials, 32:1317-26.
Zhang et al., "Tissue-specific extracellular matrix coatings for the promotion of cell proliferation and maintenance of cell phenotype." 2009, Biomaterials, 30:4021-8.
International Search Report, issued for PCT Application No. PCT/US11/59349, dated May 14, 2012.

* cited by examiner

*Primary Examiner* — Blaine Lankford
(74) *Attorney, Agent, or Firm* — Saul Ewing Arnstein & Lehr LLP; Kathryn Doyle

(57) ABSTRACT

The present invention relates to compositions and methods for mimicking an in vivo environment for culturing cells in vitro. The in vivo mimicking environment is based on the generation of a tissue-specific extracellular matrix wherein the matrix provides a substrate for which the cultured cell originated from. The tissue-specific extracellular matrix can further comprise a component of a whole tissue-specific homogenate.

54 Claims, 26 Drawing Sheets

| A | B | C | D |
|---|---|---|---|
| P, P+ES, Col, Col+EG, Col+ES, HA, HP | P+TS, Col+TG, Col+EG+TS, Col+TS, HA+TG | HA+EG, HP+EG, HP+TG | HA+EG, HA+EG+TS, HA+TS, HP+EG+TS, HP+TS, HP+ES |
| Monolayer Clusters | Spindle-Shaped | Tight Aggregates | Aggregates + Spreading |

Figure 12

TISSUE-SPECIFIC EXTRACELLULAR MATRIX WITH OR WITHOUT TISSUE PROTEIN COMPONENTS FOR CELL CULTURE

CROSS-REFERENCE TO RELATED APPLICATION

This application is the U.S. national phase application filed under 35 U.S.C. § 371 claiming benefit to International Patent Application No. PCT/US2011/059349, filed on Nov. 4, 2011, which is entitled to priority under 35 U.S.C. § 119(e) to U.S. Provisional Patent Application No. 61/412,193, filed on Nov. 10, 2010, each of which application is hereby incorporated herein by reference in its entirety.

BACKGROUND OF THE INVENTION

The liver is the only internal organ capable of natural regeneration of large portion's of lost tissue. As little as one third of a liver can regenerate itself in vivo (Michalopoulos, 2010, Am J Pathol, 176:2-13). However, liver cells placed in culture rapidly lose their in vivo phenotypic characteristics and functional abilities. This situation has limited the ability to study regenerative properties and basic functions of liver cells in vitro. As shown previously, it is difficult to maintain liver-specific function of primary hepatocytes in culture for more than one week without an adequate supportive microenvironment including substrates, e.g. extracellular matrix (ECM) coatings or feeder layers (Dunn et al., 1989, FASEB J, 3:174-7). The lack of a suitable culture platform has restricted drug discovery, toxicology, cancer, and tissue regeneration studies for liver cells. Despite decades of research, current culture products are not suitable for the expansion and maintenance of the highly specialized functions of hepatocytes. While some generic products and systems are available, they do not meet the specific culture requirements of primary liver cells. Thus, there is a need for cell culture systems that mimic the in vivo characteristics of hepatocytes.

Elements that influence human hepatocyte cultures include cell-ECM interactions, soluble growth factors and cytokines, physical factors (e.g. stress and strain) (Sadoshima et al., 1997, Annu Rev Physiol, 59:551-71; Syedain et al., 2008, Proc Natl Acad Sci USA, 105:6537-42), and cell-cell communications (Funderburgh et al., 2008, Mol Vis, 14:308-17). Importantly, cell-ECM interactions play a fundamental role in hepatocyte growth (Apte et al., 2009, Hepatology, 50:844-51; Hammond et al., 2011, J Hepatol, 54:279-87), liver organ development (Hanley et al., 2008, J Biol Chem, 283:14063-71; Semler et al., 2006, Adv Biochem Eng Biotechnol, 102:1-46), tissue regeneration (Apte et al., 2009, Hepatology, 50:844-51; Jun et al., 2010; Aging, 2:627-31; Tai et al., 2010, Biomaterials, 31:48-57), wound healing (Jun et al., 2010; Aging, 2:627-31; Gilbert et al., 2009, Laryngoscope, 119:1856-63; Povero et al., 2010, Histol Histopathol, 25:1075-91) and malignancy (Hanley et al., 2008, J Biol Chem, 283:14063-71; Mon et al., 2009, Methods Mol Biol, 512:279-93). The liver ECM contains proteins and carbohydrates that provide support and anchorage for cells, segregate tissues, and regulate intercellular communication. Commercially available tissue extracts enriched in matrix (e.g. Matrigel, collagen-I, extracts from amnions) have been used successfully as culture substrata for many years (Yamasaki et al., 2006, J Hepatol, 44:749-57). However, they are not tissue-specific (Everitt et al., 1996, J Leukoc Biol, 60:199-206; Shirahashi et al., 2004, Cell Transplant, 13:197-211). It was reported that tissue-derived ECM could be used successfully as a 2D substrate for the cell type that originated from that tissue (Zhang et al., 2009, Biomaterials, 30:4021-8). Additionally, a 3D co-culture system using a porous ECM scaffold combined with dynamic culture conditions promoted the formation of a multilayered urothelium and infiltration of smooth muscle cells into the matrix. This construct could be used to engineer urological tissue for bladder or urethral tissue reconstruction (Liu et al., 2009, Biomaterials, 30:3865-73).

Conventional tissue culture techniques relate to growing cells in vitro. Usually, the cells are cultured on a coated surface having a negative charge to enhance the attachment and sometimes proliferation of mammalian cells in culture. However, traditionally it has been most difficult to achieve a satisfactory attachment, maintenance, and propagation of mammalian cells using conventional tissue culture surfaces. Improvements have been made by adding layers of collagen gel or depositing an extracellular matrix onto the tissue culture plates and dishes to facilitate cellular attachment and proliferation. These techniques, however, are hindered by the shortcoming that the cultured cells often lose their function and viability.

Tissue engineered products hold immense potential for treating and curing disease. However, due to the complex nature of constructs comprised of living cells, biomaterials, and soluble factors, current regulatory practices and the need for long validation studies impede the clinical and commercial success of such products. One solution is the application of tissue-engineered products in commercial in vitro settings that both yield financial gain for industry while providing platforms for research, testing, and validation. The use of human cells for efficacy and toxicology screening of potential pharmaceutical agents is a current practice, but more complex human tissue constructs might yield better results that are more clinically relevant. Engineered human tissues have the potential to screen drug candidates quicker and more inexpensively in comparison to animal studies, while returning desirable results that are more relevant to humans. Incorporation of such practices in the early phases of drug development may successfully bridge the gap between laboratory research and clinical application of tissue-engineered products, both scientifically and financially (Greenhough, et al., 2010, Toxicology 278(3): 250-255). To that end, there is a need for a new biomaterial system for preparing and maintaining human hepatocyte tissue constructs with potential to be used as a drug and toxicology screening tool.

Despite many years of tissue culture research, no techniques are currently available to expand and maintain the function of highly specified cells. While generic two-dimensional (2-D) and three-dimensional (3-D) coatings exist, these products are not specific to cells. The present invention fills this gap in the art.

SUMMARY OF THE INVENTION

The present invention provides a tissue-specific in vitro cell culturing system for expanding a cell while maintaining cellular function. In one embodiment, the cell culture system comprises a culture medium and a tissue-specific component that is isolated from a tissue that normally supports the growth and maturation of the cell in vivo.

In one embodiment, the tissue is a whole tissue. In another embodiment, the whole tissue is a homogenate. In yet another embodiment, the tissue is a decellularized tissue. In one embodiment, the decellularized tissue is a homogenate.

In one embodiment, the cell that is being cultured can be selected from the group consisting of an endothelial cell, a muscle cells, a smooth muscle cell, a fibroblast, an osteoblast, a myoblast, a neuroblast, a glioblast, a germ cell, a hepatocyte, a chondrocyte, a keratinocyte, a cardiac muscle cell, a connective tissue cell, an epithelial cell, a hormone-secreting cell, a cell of the immune system, a neuron, a stem cell, and any combination thereof.

In one embodiment, the tissue of the invention can be selected from the group consisting of heart, kidney, liver, lung, pancreas, spleen, bladder, cartilage, bone, brain, spine cord, peripheral nerve, ureter, urethra, and any combination thereof.

In one embodiment the tissue-specific component of the invention is a secreted factor selected from the group consisting of a growth factor, cytokine, and any combination thereof. In another embodiment, the tissue-specific component is in the form of a sterilized fine particle. Preferably, the particle size is less than about 40 μm. In yet another embodiment, the tissue-specific component is in the form of a tissue extract supernatant.

In one embodiment, the cell culture system of the invention includes a tissue-specific component selected from the group consisting of a tissue-specific whole tissue particle, a tissue-specific decellularized tissue particle, a tissue-specific whole tissue extract, a tissue-specific decellularized tissue extract, a tissue-specific whole tissue particulate, a tissue-specific decellularized tissue particulate, and any combination thereof.

In one embodiment, the tissue-specific component is incorporated into a 2.5 D tissue particle coating. In another embodiment, the tissue-specific component is incorporated into a 3-D culture gel. In yet another embodiment, the tissue-specific component is incorporated into a 3-D porous tissue disc.

In one embodiment of the invention, the tissue-specific component is incorporated with a biopolymer. The biopolymer can be selected from the group consisting of type I collagen, hyaluronic acid, heparin-conjugated hyaluronic acid, and any combination thereof.

The invention also provides a method of maintaining cellular function of a cell cultured in vitro. In one embodiment, the method includes culturing a cell in an in vitro cell culturing system, where the culturing system includes a tissue-specific component isolated from a tissue of a mammal. In one embodiment, the tissue normally supports the growth and maturation of the cell in vivo. In one embodiment, the tissue is a whole tissue. In one embodiment, the whole tissue is a homogenate. In another embodiment, the tissue of the invention is a decellularized tissue. In one embodiment, the decellularized tissue is a homogenate.

The invention also provides a method of making a tissue-specific particle for expanding a cell while maintaining cellular function. In one embodiment, the method comprises obtaining a whole tissue from a mammal, lyophilizing the whole tissue, and powderizing the lyophilized whole tissue into particles. In one embodiment, the whole tissue is decellularized prior to lyophilizing.

The invention also provides a method of making tissue-specific extract for expanding a cell while maintaining cellular function. In one embodiment, the method comprises obtaining a whole tissue from a mammal, lyophilizing the whole tissue, powderizing the lyophilized whole tissue to generate a tissue-specific particle, forming a solution comprising the tissue-specific particle to generate a tissue-specific particle solution, separating the tissue-specific particle solution to generate a supernatant and a particulate.

In one embodiment, the supernatant is a tissue-specific extract and the particulate is a tissue-specific particulate. In one embodiment, the tissue-specific extract is isolated from the particulate. In one embodiment, the whole tissue is decellularized prior to lyophilizing. In another embodiment, the solution comprises a culture medium and the tissue-specific particle solution is mechanically agitated prior to separation. In yet another embodiment, the tissue-specific particles are mixed with pepsin prior to forming a solution, wherein the solution comprises hydrochloric acid.

The invention also provides a method of making a culture system for expanding a cell while maintaining cellular function. In one embodiment, the method comprises applying a tissue-specific component onto a surface. In one embodiment, the tissue-specific component is selected from the group consisting of a tissue-specific whole tissue particle, a tissue-specific decellularized tissue particle, a tissue-specific whole tissue extract, a tissue-specific decellularized tissue extract, a tissue-specific whole tissue particulate, a tissue-specific decellularized tissue particulate, and any combination thereof.

The invention also provides a method of making a culture system for expanding a cell while maintaining cellular function. In one embodiment, the method comprises mixing a first solution comprising a tissue-specific component with a second solution comprising a biopolymer, to generate a hydrogel. In one embodiment, the tissue-specific component is selected from the group consisting of a tissue-specific whole tissue particle, a tissue-specific decellularized tissue particle, a tissue-specific whole tissue extract, a tissue-specific decellularized tissue extract, a tissue-specific whole tissue particulate, a tissue-specific decellularized tissue particulate, and any combination thereof.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIGS. 2A through 2C, is a series of images depicting a cell viability assay (FIG. 2A) Plastic, (FIG. 2B) 3-D Liver Tissue Particulars (LTP) on day 7 of culture, (FIG. 2B) 3-D LTP on day 14 of culture.

FIGS. 4A through 4D, is a series of images depicting safranin O stain (represented by the pink) using magnification 100×; (FIG. 4A) Plastic, (FIG. 4B) 3-D collagen gel, (FIG. 4C) 3-D collagen gel mixed with cartilage tissue particulate, (FIG. 4D) 3-D collagen gel plus cartilage tissue supernatant.

FIGS. 5A through 5D, is a series images depicting morphology, immunofluorescence and myotubule analysis of cells cultured in plastic and 3-D gels. (FIG. 5A) Plastic Dish (control), (FIG. 5B) 3-D collagen type I gel, (FIG. 5C) 3-D SMT Gel, (FIG. 5D) Matrigel.

FIG. 6A and FIG. 6B, is a series of images depicting mitochondrial metabolism of primary human hepatocytes cultured in HA-based ECMs and HP-based sECMs. FIG. 6A demonstrates that hepatocytes are cultured in HA-based ECMs and FIG. 6B depicts that hepatocytes is cultured in HP-based ECMs. MTS assays were performed on week 1, 2, 3, and 4. Significance: *p<0.01; **p<0.05.

FIG. 7A through 7D, is a series of images demonstrating that ECMs and extract combinations induce distinct morphological differences in primary human hepatocyte culture. Representative images from week 1 and week 4 are shown: FIG. 7A is an image that depicts monolayer clusters; FIG. 7B is an image that depicts interconnected structures that deteriorated; FIG. 7C is an image that depicts individual cells with no cell-cell organization; and FIG. 7D is an image that depicts stable interconnected structure. Constructs were LIVE/DEAD-stained to highlight viable and dead cells. Green fluorescence indicates calcein-AM-stained live cells and red fluorescence indicates ethidium homodimer-1-stained dead cells.

FIG. 8A through FIG. 8H, is a series images demonstrating that hepatocytes in HA and HP constructs secrete consistent levels of albumin, quantified by ELISA. FIG. 8A depicts the results in HA constructs and FIG. 8B depicts the results in HP constructs. Albumin IHC revealed differences in intracellular albumin. FIG. 8C is an image of HP+EG; FIG. 8D is an image of HP+EG+TS, HP+TG; FIG. 8E is an image of HP, HA+EG, HA+EG+TS; FIG. 8F is an image of HA, HA+TS, CG+EG, CG+EG+TS, CG+TG, CG+ES; FIG. 8G is an image of P, P+ES, P+TS; and FIG. 8H is an image of HP+ES, HP+TS, HA+ES, HA+TS.

FIG. 9A and FIG. 9B, is a series of images demonstrating that hepatocytes in HA and HP constructs secrete consistent levels of urea, respectively, quantified by a colorimetric assay. FIG. 9A depicts the results in HA constructs and FIG. 9B depicts the results in HP constructs.

FIG. 10A through FIG. 10C, is a series of images depicting kinetic assay of Cytochrome p450-dependent metabolism of the drug ethoxycoumarin by hepatocytes cultured in HA and HP constructs. FIG. 10A depicts the results in HA constructs, and FIG. 10B depicts the results in HP constructs. RFUs are proportional to the amount of drug metabolized. The assay was performed at week 4. FIG. 10C depicts cumulative Cytochrome p450 activity at the end of the 15 minute kinetic assay. Significance: *p<0.05.

FIG. 12, comprising FIG. 12A through FIG. 12D, is a series of images demonstrating that the 21 groups fell into 4 main categories of differing morphology. FIG. 12A demonstrates that the groups P, P+ES, COL, COL+EG, COL+ES, HA, and HP displayed the monolayer cluster morphology commonly observed when HEPG2s are cultured on plastic. FIG. 12B demonstrates that the groups P+TS, COL+TG, COL+EG+TS, COL+TS, and HA+TG displayed a different spindle shaped morphology. FIG. 12C demonstrates that the groups HA+EG, HP+EG, and HP+TG, in which the cells formed tight rounded aggregates. FIG. 12D demonstrates that the groups HA+EG, HA+EG+TS, HA+TS, HP+EG+TS, HP+TS, and HP+ES supported cells to formed tight aggregates but then the cells spread outwards from the aggregates over time.

FIG. 14A and FIG. 14B, is a series of images depicting albumin and urea production in plastic and collagen-based substrates groups over the 4 week experiment. FIG. 14A demonstrates that all plastic and collagen-based groups showed a week-to-week decreasing trend in albumin production for plastic and collagen groups, and FIG. 14B demonstrates that all 3 plastic groups secreted significantly less urea on week 4 than on week 1

(FIG. 16B) water, (FIG. 16C) PBS, (FIG. 16D) salt, (FIG. 16E) water+PAA, (FIG. 16F) PBS+PAA, (FIG. 16G) salt+PAA. Magnification=200×.

FIG. 18A through FIG. 18C, illustrates the analysis of ECM discs following decellularization. FIG. 18A shows the histological analysis of liver ECM discs following each of the six methods of decellularization. Note the absence of nuclei in decellularized tissue. Hematoxylin and eosin staining. Scale bar=50 µm. Magnification=200×. FIG. 18B shows that proteoglycans and collagen components were retained within decellularized liver ECM. Alcian Blue and Sirius Red staining showed that the proteoglycans and collagen were retained within ECM after each of the six decellularization methods. Magnification=100×. FIG. 18C shows scanning electron microscopy of decellularized liver ECM discs. Electron micrographs display the surface architecture of scaffolds after each of the six methods of decellularization.

FIG. 20A and FIG. 20B, depicts ECM components after dellularization. FIG. 20A shows the detection of multiple types of collagen retained during decellularization with the water wash method. Immunohistochemical staining of liver ECM discs for collagens-I, -III and -IV are shown. Bar=100 µm. Magnification=200×. FIG. 20B shows the detection of fibronectin, laminin, and elastin retained during decellularization with the water-wash method. Immunohistochemical staining of liver ECM discs for fibronectin, laminin and elastin is depicted. Bar=100 µm. Magnification=200×.

FIG. 23A through FIG. 23D, shows the morphology of HepG2 cells and human hepatocytes cultured on decellularized liver ECM discs. FIG. 23A shows HepG2 cells cultured on ECM discs under dynamic culture conditions on day 12 (H&E stain). FIG. 23B and FIG. 23C depict primary human hepatocytes cultured on ECM discs under static culture conditions on day 21 (H&E and Masson's trichrome stains, respectively). FIG. 23D shows Live/dead staining of hepatocytes cultured on ECM discs (green staining=viable). Magnification: i-iii=400×; iv=200×.

FIG. 26A shows HepG2 cells cultured on polystyrene culture plates as a control. FIG. 26B shows human hepatocytes grown on polystyrene dishes. FIG. 26C shows sandwich culture of human hepatoctyes viewed via confocal microscopy; FIG. 26D shows human hepatocytes grown on liver ECM discs (cross section). Specific albumin staining appears bright green and nuclear staining either as blue (DAPI) or red (PI). Magnification=400×.

DETAILED DESCRIPTION

Figure 1:
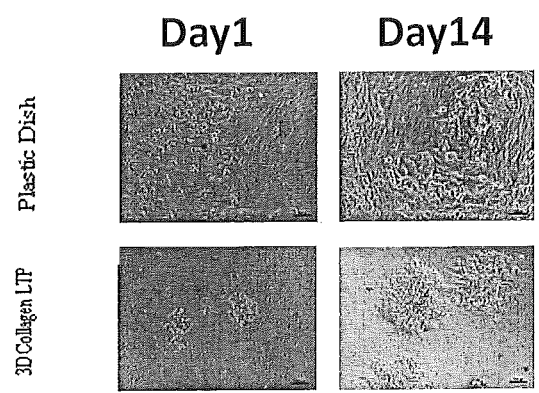
FIG. 1 is an image depicting cellular morphology of plastic and 3-D gel matrices; magnification of 100×.

The present invention is based on the discovery that culturing a cell in vitro in the presence of a tissue-specific extracellular matrix (ECM) allows the cell to grow as it would typically in the in vivo environment with which it is naturally associated and maintain its natural function while doing so. In some embodiments, the tissue-specific ECM comprises components derived from a whole tissue-specific homogenate. A whole tissue-specific homogenate may contain epithelium, supportive stroma and vessels, as well as any secretions such as growth factors and cytokines that are normally present in the tissue in vivo. Therefore, as used elsewhere herein, a tissue-specific ECM refers to a tissue-specific ECM that includes components of a whole tissue-specific homogenate or is devoid of some or all components of the whole tissue-specific homogenate. In any event, the tissue-specific ECM, with or without a component of a whole tissue-specific homogenate, can be used as a substrate to culture a cell type that originated from that tissue.

The invention provides compositions and methods for culturing, maintaining, and inducing a cell to exhibit characteristics similar to that of the corresponding cell naturally found in vivo. In one embodiment, the invention provides compositions and methods for enhancing cell growth and maintaining cellular function.

The cell culturing model of the invention is useful for investigating tissue developmental biology, stem cell differentiation and tissue engineering. In addition, the model is useful for among other things, drug discovery, toxicity testing, elucidation of disease pathology and thereby enhancing diagnosis and therapy, and the like.

In one embodiment, the invention includes a tissue-specific ECM coating, with or without a component of a whole tissue-specific homogenate, for cell culture that provides tissue-specific cues unlike traditional cell culture coatings, thereby enabling the culturing and maturation of a desired cell type. The tissue-specific ECM coating is applicable to any cell provided that the desired cell type is cultured with the matched tissue-specific ECM. A matched tissue-specific ECM, with or without protein, is one where the cultured cell would normally be found in vivo or is otherwise the tissue of origin of the cell.

In one embodiment, the tissue-specific ECM, with or without a component of a whole tissue-specific homogenate, can be derived by decellularization or partial decellularization of a desired tissue. In some instances, it is desirable to not decellularize the desired tissue.

In one embodiment, the whole tissue or decellularized tissue is minced, lyophilized and grounded into a fine powder (e.g., particle size <40 µm). The fine powder is sterilized using gamma irradiation thereby generating a sterile tissue particle. In other instances, the sterile tissue particle is mixed with a desired culture medium and cultured with the appropriate cell type. In yet other instances, the sterile tissue particle is mixed with other biopolymers or synthetic polymers in the formation of a hydrogel, and cultured with the appropriate cell type. In another embodiment, the sterile tissue particle is mixed with a desired culture medium and the supernatant thereof is mixed with a desired culture medium and cultured with the appropriate cell type. In yet another embodiment, the supernatant is mixed with other biopolymers or synthetic polymers in the formation of a hydrogel, and cultured with the appropriate cell type. An advantage of using the tissue-specific ECM of the invention allows the culturing of a cell in vitro where the cultured cell does not lose function and viability.

In one embodiment, the invention provides a 2.5-D tissue particle coating for culturing cells. The 2.5-D tissue particle coating can be generated by mixing the sterile tissue particle of the invention with a solution and applying the mixture on a cell culturing surface.

In one embodiment, the invention provides a 3-D tissue-specific ECM for culturing cells. In one embodiment of the 3-D tissue-specific ECM of the invention is generated by mixing the tissue component of the invention with a biopolymer in the formation of a hydrogel. A tissue component of the invention can include but is not limited to a tissue-specific whole tissue particle, a tissue-specific decellularized tissue particle, a tissue-specific whole tissue extract, a tissue-specific decellularized tissue extract, a tissue-specific whole tissue particulate, and a tissue-specific decellularized tissue particulate. Preferably, the biopolymer includes but is not limited to type I collagen, hyaluronic acid, heparin-conjugated hyaluronic acid, and the like.

Another embodiment of the 3-D tissue specific ECM provides a 3-D porous tissue disc for culturing cells. The 3-D porous tissue disc is generated by incubating a fully decellularized tissue disc with a desired solution for a period time and washing away cellular compound to generate a porous surface. In some instances, it is beneficial to leave certain cellular protein compounds within the center of the tissue disc (i.e., partially decellularized tissue disc). The 3-D porous tissue disc can be used to culture the desired cell type.

In one embodiment, the invention provides a tissue extract supernatant for culturing cells. The tissue extract supernatant is generated by mixing the sterile tissue particles with a culture medium. The resulting suspension can be mechanically agitated through high speed mixing (e.g. vortexing). In another embodiment, instead of mechanical agitation, the suspension can be agitated chemically. A non-limiting example of chemical agitation includes mixing the suspension with an acidic solution comprising pepsin and hydrochloric acid. Following mechanical or chemical agitation, the suspension can then be centrifuged to generate a supernatant tissue extract that can be used for culturing cells or for incorporation into an engineered ECM. Preferably, the tissue extract comprises soluble growth factors and cytokines. In some instances, the tissue extract comprises insoluble growth factors and cytokines. In other instances, the tissue extract solution comprises both soluble and insoluble growth factors and cytokines.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The terms "cells" and "population of cells" are used interchangeably and refer to a plurality of cells, i.e., more than one cell. The population may be a pure population comprising one cell type. Alternatively, the population may comprise more than one cell type. In the present invention, there is no limit on the number of cell types that a cell population may comprise.

As used here, "biocompatible" refers to any material, which, when implanted in a mammal, does not provoke an adverse response in the mammal. A biocompatible material, when introduced into an individual, is not toxic or injurious to that individual, nor does it induce immunological rejection of the material in the mammal.

As used herein, the term "biocompatible lattice," is meant to refer to a substrate that can facilitate formation into three-dimensional structures conducive for tissue development. Thus, for example, cells can be cultured or seeded onto such a biocompatible lattice, such as one that includes extracellular matrix material, synthetic polymers, cytokines, growth factors, etc. The lattice can be molded into desired shapes for facilitating the development of tissue types. Also, at least at an early stage during culturing of the cells, the medium and/or substrate is supplemented with factors (e.g., growth factors, cytokines, extracellular matrix material, etc.) that facilitate the development of appropriate tissue types and structures.

"Bioactive agents," as used herein, can include one or more of the following: chemotactic agents; therapeutic agents (e.g., antibiotics, steroidal and non-steroidal analgesics and anti-inflammatories (including certain amino acids such as glycine), anti-rejection agents such as immunosuppressants and anti-cancer drugs); various proteins (e.g., short term peptides, bone morphogenic proteins, collagen, hyaluronic acid, glycoproteins, and lipoprotein); cell attachment mediators; biologically active ligands; integrin binding sequence; ligands; various growth and/or differentiation agents and fragments thereof (e.g., epidermal growth factor (EGF), hepatocyte growth factor (HGF), vascular endothelial growth factors (VEGF), fibroblast growth factors (e.g., bFGF), platelet derived growth factors (PDGF), insulin derived growth factor (e.g., IGF-1, IGF-II) and transforming growth factors (e.g., TGFβ I-III), parathyroid hormone, parathyroid hormone related peptide, bone morphogenic proteins (e.g., BMP-2, BMP-4; BMP-6; BMP-7; BMP-12; BMP-13; BMP-14), sonic hedgehog, growth differentiation factors (e.g., GDF5, GDF6, GDF8), recombinant human growth factors (e.g., MP52, and MP-52 variant rhGDF-5), cartilage-derived morphogenic proteins (CDMP-1; CDMP-2, CDMP-3)); small molecules that affect the upregulation of specific growth factors; tenascin-C; hyaluronic acid; chondroitin sulfate; fibronectin; decorin; thromboelastin; thrombin-derived peptides; heparin-binding domains; heparin; heparan sulfate. Suitable effectors likewise include the agonists and antagonists of the agents described above. The growth factor can also include combinations of the growth factors described above. In addition, the growth factor can be autologous growth factor that is supplied by platelets in the blood. In this case, the growth factor from platelets will be an undefined cocktail of various growth factors. If other such substances have therapeutic value in the orthopedic field, it is anticipated that at least some of these substances will have use in the present invention, and such substances should be included in the meaning of "bioactive agent" and "bioactive agents" unless expressly limited otherwise. Preferred examples of bioactive agents include culture media, bone morphogenic proteins, growth factors, growth differentiation factors, recombinant human growth factors, cartilage-derived morphogenic proteins, hydrogels, polymers, antibiotics, anti-inflammatory medications, immunosuppressive mediations, autologous, allogenic or xenologous cells such as stem cells, chondrocytes, fibroblast and proteins such as collagen and hyaluronic acid. Bioactive agents can be autologus, allogenic, xenogenic or recombinant.

The term "biologically compatible carrier" or "biologically compatible medium" refers to reagents, cells, compounds, materials, compositions, and/or dosage formulations which are suitable for use in contact with the tissues of human beings and animals without excessive toxicity, irritation, allergic response, or other complication commensurate with a reasonable benefit/risk ratio.

As used herein, the term "bone marrow stromal cells," "stromal cells," "mesenchymal stem cells," "mesenchymal stromal cells" or "MSCs" are used interchangeably and refer to a cell derived from bone marrow (reviewed in Prockop, 1997), peripheral blood (Kuznetsov et al., 2001), adipose tissue (Guilak et al., 2004), umbilical cord blood (Rosada et al., 2003), synovial membranes (De Bari et al., 2001), and periodontal ligament (Seo et al., 2005). MSCs are characterized by their ability to adhere to plastic tissue culture surfaces (Friedenstein et al.; reviewed in Owen & Friedenstein, 1988), and by being an effective feeder layers for hematopoietic stem cells (Eaves et al., 2001). In addition, MSCs can be differentiated both in culture and in vivo into osteoblasts and chondrocytes, into adipocytes, muscle cells (Wakitani et al., 1995) and cardiomyocytes (Fukuda and Yuasa, 2006), into neural precursors (Woodbury et al., 2000; Deng et al., 2001, Kim et al., 2006; Mareschi et al., 2006; Krampera et al., 2007). Mesenchymal stem cells (MSCs) may be purified using methods known in the art (Wakitani et al., 1995; Fukuda and Yuasa, 2006; Woodbury et al., 2000; Deng et al., 2001; Kim et al., 2006; Mareschi et al., 2006; Krampera et al., 2007).

The term "cell medium" as used herein, refers to a medium useful for culturing cells. An example of a cell medium is a medium comprising DMEM/F 12 Ham's, 10% fetal bovine serum, 100 U penicillin/100 µg streptomycin/0.25 µg Fungizone. Typically, the cell medium comprises a base medium, serum and an antibiotic/antimycotic. However, cells can be cultured with stromal cell medium without an antibiotic/antimycotic and supplemented with at least one growth factor. Preferably the growth factor is human epidermal growth factor (hEGF). The preferred concentration of hEGF is about 1-50 ng/ml, more preferably the concentration is about 5 ng/ml. The preferred base medium is DMEM/F12 (1:1). The preferred serum is fetal bovine serum (FBS) but other sera may be used including horse serum or human serum. Preferably up to 20% FBS will be added to the above media in order to support the growth of stromal cells. However, a defined medium could be used if the necessary growth factors, cytokines, and hormones in FBS for cell growth are identified and provided at appropriate concentrations in the growth medium. It is further recognized that additional components may be added to the culture medium. Such components include but are not limited to antibiotics, antimycotics, albumin, growth factors, amino acids, and other components known to the art for the culture of cells. Antibiotics which can be added into the medium include, but are not limited to, penicillin and streptomycin. The concentration of penicillin in the culture medium is about 10 to about 200 units per ml. The concentration of streptomycin in the culture medium is about 10 to about 200 µg/ml. However, the invention should in no way be construed to be limited to any one medium for culturing cells. Rather, any media capable of supporting cells in tissue culture may be used.

The term "decellularized" or "decellularization" as used herein refers to a biostructure (e.g., an organ, or part of an organ), from which the cellular and tissue content has been removed leaving behind an intact acellular infra-structure. Organs such as the kidney are composed of various specialized tissues. The specialized tissue structures of an organ, or parenchyma, provide the specific function associated with the organ. The supporting fibrous network of the organ is the stroma. Most organs have a stromal framework composed of unspecialized connecting tissue which supports the specialized tissue. The process of decellularization removes the specialized tissue, leaving behind the complex three-dimensional network of connective tissue. The connective tissue infra-structure is primarily composed of collagen. The decellularized structure provides a biocompatible substrate onto which different cell populations can be infused. Decellularized biostructures can be rigid, or semi-rigid, having an ability to alter their shapes. Examples of decellularized organs useful in the present invention include, but are not limited to, the heart, kidney, liver, pancreas, spleen, bladder, ureter and urethra, cartilage, bone, brain, spine cord, peripheral nerve.

The term "dedifferentiation", as used herein, refers to the return of a cell to a less specialized state. After dedifferentiation, such a cell will have the capacity to differentiate into more or different cell types than was possible prior to re-programming. The process of reverse differentiation (i.e., de-differentiation) is likely more complicated than differentiation and requires "re-programming" the cell to become more primitive.

"Differentiation medium" is used herein to refer to a cell growth medium comprising an additive or a lack of an additive such that a stem cell, adipose derived adult stromal cell or other such progenitor cell, that is not fully differentiated when incubated in the medium, develops into a cell with some or all of the characteristics of a differentiated cell.

As used herein "endogenous" refers to any material from or produced inside an organism, cell or system.

"Exogenous" refers to any material introduced from or produced outside an organism, cell, or system.

"Expandability" is used herein to refer to the capacity of a cell to proliferate, for example, to expand in number or in the case of a cell population to undergo population doublings.

As used herein, a "graft" refers to a cell, tissue or organ that is implanted into an individual, typically to replace, correct or otherwise overcome a defect. A graft may further comprise a scaffold. The tissue or organ may consist of cells that originate from the same individual; this graft is referred to herein by the following interchangeable terms: "autograft", "autologous transplant", "autologous implant" and "autologous graft". A graft comprising cells from a genetically different individual of the same species is referred to herein by the following interchangeable terms: "allograft", "allogeneic transplant", "allogeneic implant" and "allogeneic graft". A graft from an individual to his identical twin is referred to herein as an "isograft", a "syngeneic transplant", a "syngeneic implant" or a "syngeneic graft". A "xenograft", "xenogeneic transplant" or "xenogeneic implant" refers to a graft from one individual to another of a different species.

As used herein "growth factors" is intended the following non-limiting factors including, but not limited to, growth hormone, erythropoietin, thrombopoietin, interleukin 3, interleukin 6, interleukin 7, macrophage colony stimulating factor, c-kit ligand/stem cell factor, osteoprotegerin ligand, insulin, insulin like growth factors, epidermal growth factor (EGF), fibroblast growth factor (FGF), nerve growth factor, ciliary neurotrophic factor, platelet derived growth factor (PDGF), transforming growth factor (TGF-beta), hepatocyte growth factor (HGF), and bone morphogenetic protein at concentrations of between picogram/ml to milligram/ml levels.

As used herein "angiogenic growth factors" is intended the following non-limiting factors including, but are not limited to ARTS-1, ECGF1, EREG, FGF1, FGF2, FGF6, FIGF, IL18, JAG1, PGF, TNNT1, VEGFA, VEGFC, and the like.

As used herein "cell differentiation markers" is intended the following non-limiting factors including, but are not limited to ARTS-1, BMP1, BMP2, BMP3, BMP4, BMP5, BMP6, BMP7, BMP8B, CSF1, CSPG5, ECGF1, EREG, FGF1, FGF2, FGF22, FGF23, FGF6, FGF9, FIGF, IL10, IL11, IL12B, IL2, IL4, INHA, INHBA, INHBB, JAG1, JAG2, LTBP4, MDK, NRG1, OSGIN1 (OKL38), PGF, SLCO1A2, SPP1, TDGF1, TNNT1, VEGFC, and the like.

As used herein "development controllers" is intended the following non-limiting controllers including, but are not limited to embryonic development markers, nervous system development markers, central nervous system development markers, muscle development markers, skeletal development markers, cartilage development markers, ovarian follicle development, and the like. Angiogenic Growth Factors include but are not limited to ARTS-1, ECGF1, EREG, FGF1, FGF2, FGF6, FIGF, IL18, JAG1, PGF, TNNT1, VEGFA, VEGFC, and the like. Cell Differentiation markers include but are not limited to ARTS-1, BMP1, BMP2, BMP3, BMP4, BMP5, BMP6, BMP7, BMP8B, CSF1, CSPG5, ECGF1, EREG, FGF1, FGF2, FGF22, FGF23, FGF6, FGF9, FIGF, IL10, IL11, IL12B, IL2, IL4, INHA, INHBA, INHBB, JAG1, JAG2, LTBP4, MDK, NRG1, OSGIN1 (OKL38), PGF, SLCO1A2, SPP1, TDGF1, TNNT1, VEGFC, and the like. Embryonic Development markers include but are not limited to BMP10, NRG1, NRG2, NRG3, TDGF1, and the like. Nervous System Development markers include but are not limited to BDNF, CSPG5, CXCL1, FGF11, FGF13, FGF14, FGF17, FGF19, FGF2, FGF5, GDF11, GDNF, GPI, IL3, INHA, INHBA, JAG1, MDK, NDP, NRG1, NRTN, NTF3, PTN, VEGFA, and the like. Central Nervous System Development markers include but are not limited to PDGFC, PSPN, and the like. Muscle Development markers include but are not limited to FGF2, GDF8, HBEGF, IGF1, TNNT1, and the like. Skeletal Development markers include but are not limited to GDF10, GDF11, IGF1, IGF2, INHA, INHBA, and the like. Cartilage Development markers include but are not limited to BMP2, BMP3, BMP4, BMP5, BMP6, BMP7, BMP8B. Ovarian Follicle Development markers include but are not limited to INHA, INHBA, INHBB, and the like. Others markers include but are not limited to AMH, CECR1, CSF2, CSF3, DKK1, FGF7, LEFTY1, LEFTY2, LIF, LTBP4, NGFB, NODAL, TGFB1, THPO, and the like.

As used herein, the term "growth medium" is meant to refer to a culture medium that promotes growth of cells. A growth medium will generally contain animal serum. In some instances, the growth medium may not contain animal serum.

The term "hydrogel" as used herein refers to a network of oligomers or polymer chains that are water-insoluble. In some instance, the hydrogel can be found as a colloidal gel in which water is the dispersion medium.

An "isolated cell" refers to a cell which has been separated from other components and/or cells which naturally accompany the isolated cell in a tissue or mammal.

As used herein, the term "multipotential" or "multipotentiality" is meant to refer to the capability of a stem cell of the central nervous system to differentiate into more than one type of cell.

As used herein, the term "modulate" is meant to refer to any change in biological state, i.e. increasing, decreasing, and the like.

The terms "precursor cell," "progenitor cell," and "stem cell" are used interchangeably in the art and herein and refer either to a pluripotent, or lineage-uncommitted, progenitor cell, which is potentially capable of an unlimited number of mitotic divisions to either renew itself or to produce progeny cells which will differentiate into the desired cell type. Unlike pluripotent stem cells, lineage-committed progenitor cells are generally considered to be incapable of giving rise to numerous cell types that phenotypically differ from each other. Instead, progenitor cells give rise to one or possibly two lineage-committed cell types.

"Proliferation" is used herein to refer the reproduction or multiplication of similar forms, especially of cells. That is, proliferation encompasses production of a greater number of cells, and can be measured by, among other things, simply counting the numbers of cells, measuring incorporation of $^3$H-thymidine into the cell, and the like.

"Progression of or through the cell cycle" is used herein to refer to the process by which a cell prepares for and/or enters mitosis and/or meiosis. Progression through the cell cycle includes progression through the G1 phase, the S phase, the G2 phase, and the M-phase.

As used herein, "scaffold" refers to a structure, comprising a biocompatible material that provides a surface suitable for adherence and proliferation of cells. A scaffold may further provide mechanical stability and support. A scaffold may be in a particular shape or form so as to influence or delimit a three-dimensional shape or form assumed by a population of proliferating cells. Such shapes or forms include, but are not limited to, films (e.g. a form with two-dimensions substantially greater than the third dimension), ribbons, cords, sheets, flat discs, cylinders, spheres, 3-dimensional amorphous shapes, etc.

As used herein, a "substantially purified" cell is a cell that is essentially free of other cell types. Thus, a substantially purified cell refers to a cell which has been purified from other cell types with which it is normally associated in its naturally occurring state.

The phrase "three-dimensional scaffold" as used herein refers to the residual infra-structure formed when a natural biostructure, e.g. an organ, is decellularized. This complex, three-dimensional, scaffold or gel provides the supportive framework that allows cells to attach to it, and grow on it. Cultured populations of cells can then be grown on the three-dimensional scaffold or gel, which provides the exact interstitial distances required for cell-cell interaction and cell matrix interaction. This provides a reconstructed organ that resembles the native in vivo organ.

As used herein, "tissue engineering" refers to the process of generating tissues ex vivo for use in tissue replacement or reconstruction. Tissue engineering is an example of "regenerative medicine," which encompasses approaches to the repair or replacement of tissues and organs by incorporation of cells, gene or other biological building blocks, along with bioengineered materials and technologies.

"Transplant" refers to a biocompatible lattice or a donor tissue, organ or cell, to be transplanted. An example of a transplant may include but is not limited to skin cells or tissue, bone marrow, and solid organs such as heart, pancreas, kidney, lung and liver.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention provides compositions and methods for culturing cells in an environment that resembles the in vivo environment of the cell. Thus, the invention provides an in vitro culturing model that mimics the in vivo environment of the cell in a tissue-specific manner.

In one embodiment, the invention includes a biocompatible scaffold comprising a tissue-specific ECM, with or without a component of a whole tissue-specific homogenate, where the scaffold can be seeded with a desired cell type, provided that the ECM is a substrate for the cell type that originated from that tissue. The biocompatible scaffold comprising the desired cell type can be used as a model for preclinical in vitro pharmacological, physiological, and drug testing.

In some instances, progenitor or stem cells may be cultured with the tissue-specific ECM, with or without a component of a whole tissue-specific homogenate, and may be induced to differentiate prior to implantation for tissue reconstruction (i.e. ex vivo), or may be induced to differentiate after implantation (i.e. in vivo).

In a preferred embodiment, tissue-specific ECM can be used to make a biocompatible scaffold which is seeded with a desired cell type. After seeding, the cells on the scaffold are optionally subjected to an expansion medium or to a differentiation medium, or are cultured in the presence of tissue-specific growth factors. The composition can be implanted into a subject in need thereof. The subject may be a mammal, but is preferably a human. The source of the cells for growth and implantation is any mammal, but also preferably a human. The implanted composition supports additional cell growth in vivo, thus facilitating tissue reconstruction. Accordingly, the invention includes the use of engineered three dimensional structures for tissue grafting therapies.

The compositions and methods of the instant invention have a myriad of useful applications. The compositions may be used in therapeutic methods for alleviating or treating tissue defects in an individual. The compositions may also be used in vitro or in vivo to identify compounds that may have therapeutic potential.

In one embodiment, the cell cultures can be maintained in vitro and be exposed to the compound to be tested. The activity of a cytotoxic compound can be measured by its ability to damage or kill cells in culture. This may readily be assessed using vital staining techniques. The effect of growth/regulatory factors may be assessed by analyzing the cellular content of the matrix, e.g., by total cell counts, and differential cell counts. This may be accomplished using standard cytological and/or histological techniques including the use of immunocytochemical techniques employing antibodies that define type-specific cellular antigens. The effect of various drugs on normal cells cultured in the artificial tissue may be assessed.

Tissue-Specific ECM Preparations

The present invention is based on the discovery that a tissue-specific ECM, with or without a component of a whole tissue-specific homogenate, is useful for culturing a cell type that originated from that tissue. In one embodiment, the invention provides a tissue-specific ECM coating for cell culture that provides tissue-specific cues unlike traditional cell culture coatings, thereby enabling the culturing and maturation of a desired cell type. The tissue-specific ECM coating is applicable to any cell provided that the desired cell type is cultured with the matched tissue-specific ECM. A matched tissue-specific ECM is one that the cultured cell would normally be found in vivo or otherwise is the tissue of origin of the cell.

In one embodiment, the tissue-specific ECM, with or without a component of a whole tissue-specific homogenate, can be derived from decellularization of a desired tissue. In some instances, the tissue-specific ECM is generated using a decellularization/oxidation procedure. In some instances, the tissue is minced, lyophilized and grounded into a fine powder (e.g., particle size <40 µm). The fine powder is sterilized using gamma irradiation thereby generating a sterile tissue particulate that can provide a substrate for culturing cells.

Natural biostructures, e.g. an organ or tissue, can be obtained from a donor of the same species as the subject, for example, a human cadaver kidney for a human kidney recipient. The natural biostructure can also be obtained from a different species which includes, but is not limited to, monkeys, dogs, cats, mice, rats, cows, horses, pigs, goats and sheep. The natural biostructure can also be obtained from a subject requiring a reconstructed organ. For example, a subject with one dysfunctional kidney and one functional kidney can have the dysfunctional kidney removed and decellularized using the process described below. As a non-limiting example, the decellularized kidney of the subject can be used as the three-dimensional scaffold to reconstruct an artificial kidney using cultured endothelial cells and kidney cells isolated from the subject. The artificial reconstructed kidney can then be implanted back into the subject for further development.

Biostructures, e.g., whole organs, or parts of organs can be decellularized by removing the entire cellular and tissue content from the organ. The decellularization process comprises a series of sequential extractions. One feature of this extraction process is that harsh extraction that may disturb or destroy the complex infra-structure of the biostructure, can be avoided. The first step involves removal of cellular debris and solubilization of the cell membrane. This is followed by solubilization of the nuclear cytoplasmic components and the nuclear components.

Preferably, the biostructure, e.g., an organ or tissue, is decellularized by removing the cell membrane and cellular debris surrounding the organ using gentle mechanical disruption methods. The gentle mechanical disruption methods must be sufficient to disrupt the cellular membrane. However, the process of decellularization should avoid damage or disturbance of the biostructure's complex infra-structure. Gentle mechanical disruption methods include scraping the surface of the organ, agitating the organ, or stirring the organ in a suitable volume of fluid, e.g., distilled water. In one preferred embodiment, the gentle mechanical disruption method includes magnetically stirring (e.g., using a magnetic stir bar and a magnetic plate) the organ in a suitable volume of distilled water until the cell membrane is disrupted and the cellular debris has been removed from the organ.

After the cell membrane has been removed, the nuclear and cytoplasmic components of the biostructure are removed. This can be performed by solubilizing the cellular and nuclear components without disrupting the infra-structure. To solubilize the nuclear components, non-ionic detergents or surfactants may be used. Examples of non-ionic detergents or surfactants include, but are not limited to, the Triton series, available from Rohm and Haas of Philadelphia, Pa., which includes Triton X-100, Triton N-101, Triton X-114, Triton X-405, Triton X-705, and Triton DF-16, available commercially from many vendors; the Tween series, such as monolaurate (Tween 20), monopalmitate (Tween 40), monooleate (Tween 80), and polyoxethylene-23-lauryl ether (Brij. 35), polyoxyethylene ether W-1 (Polyox), and the like, sodium cholate, deoxycholates, CHAPS, saponin, n-Decyl beta-D-glucopyranoside, n-heptyl.beta.-D glucopyranoside, n-Octyl-alpha-D-glucopyranoside and Nonidet P-40.

The concentration of the non-ionic detergent may be altered depending on the type of biostructure being decellularized. For example, for delicate tissues, e.g., blood vessels, the concentration of the detergent should be decreased. Preferred concentration ranges of non-ionic detergent can be from about 0.001 to about 2.0% (w/v); more preferably, about 0.05 to about 1.0% (w/v); even more preferably, about, 0.1% (w/v) to about 0.8% (w/v). Preferred concentrations range from about 0.001 to about 0.2% (w/v), with about 0.05 to about 0.1% (w/v) being particular preferred.

The cytoskeletal component, comprising the dense cytoplasmic filament networks, intercellular complexes and apical microcellular structures, may be solubilized using alkaline solution, such as, ammonium hydroxide. Other alkaline solutions comprising ammonium salts or their derivatives may also be used to solubilize the cytoskeletal components. Examples of other suitable ammonium solutions include ammonium sulphate, ammonium acetate and ammonium hydroxide. In a preferred embodiment, ammonium hydroxide is used.

The concentration of the alkaline solutions, e.g., ammonium hydroxide, may be altered depending on the type of biostructure being decellularized. For example, for delicate tissues, e.g., blood vessels, the concentration of the detergent should be decreased. Preferred concentrations ranges can be from about 0.001 to about 2.0% (w/v); more preferably, about 0.005 to about 0.1% (w/v); even more preferably, about, 0.01% (w/v) to about 0.08% (w/v).

In some embodiments, decellularization of the biostructure comprises incubation of the biostructure in at least one of distilled water, PBS, or salt solution. In another embodiment, after decellularization, the biostructure is treated with an acid, preferably peracetic acid (PAA). Preferred concentration ranges of PAA can be from about 0.05 to about 20% (w/v); more preferably, about 0.5 to about 15% (w/v); even more preferably, about, 0.1 (w/v) to about 10% (w/v). Preferred concentrations range from about 1 to about 8% (w/v), with about 2.5 to about 5% (w/v) being particular preferred.

In some instances, following decellularization, the biostructure is lyophilized. The decellularized, lyophilized structure may be stored at a suitable temperature until required for use. Prior to use, the decellularized structure can be equilibrated in suitable isotonic buffer or cell culture medium. Suitable buffers include, but are not limited to, phosphate buffered saline (PBS), saline, MOPS, HEPES, Hank's Balanced Salt Solution, and the like. A suitable cell culture medium includes, but is not limited to, RPMI 1640, Fisher's, Iscove's, McCoy's, Dulbecco's medium, and the like.

The decellularized and lyophilized biostructure can be sterilized using gamma irradiation thereby generating a sterile tissue-specific construct. The construct can be cut to any size prior to culturing. In some instances, the tissue-specific construct is seeded with the appropriate cell type.

In some instances, following decellularization and lyophilization, the biostructure is processed into a fine powder. Preferably, the fine powder has a particle size about <40 µM. The fine powder can be sterilized using gamma irradiation thereby generating sterile decellularized tissue particles. In some further instances, the sterile decellularized tissue particles are mixed with a desired culture medium and cultured with the appropriate cell type. In other instances, the sterile decellularized tissue particle is incorporated into a hydrogel and cultured with the appropriate cell type.

In some instances, the sterile decellularized tissue particles can be further processed. In some instances, decellularized tissue particles can be mechanically agitated. For example, particles can be mixed with culture medium and the resulting solution can be vortexed. In some instances, decellularized tissue particles can be chemically or enzymatically agitated. For example, tissue particles can be mixed with a solution comprising pepsin, hydrochloric acid, or both. In some instances, the mechanically agitated or chemically/enzymatically agitated decellularized particle solutions can be centrifuged to form a supernatant and a particulate. The supernatant is known as the tissue-specific decellularized tissue extract, and the particulate is known as the tissue-specific decellularized tissue particulate. In some instances the decellularized tissue extract is substantially separated from the decellularized tissue particulate. In some instances the decellularized tissue extract is mixed with a desired culture medium and cultured with the appropriate cell type. In other instances, the decellularized tissue extract is incorporated into a hydrogel and cultured with the appropriate cell type.

In some instances the decellularized tissue particulate is mixed with a desired culture medium and cultured with the appropriate cell type. In other instances, the decellularized tissue particulate is incorporated into a hydrogel and cultured with the appropriate cell type.

In some instances, the entire decellularized particle solution following mechanically or chemically/enzymatically agitation is mixed with a desired culture medium and cultured with the appropriate cell type. In other instances, the particle solution is incorporated into a hydrogel and cultured with the appropriate cell type.

In some instances, it is beneficial to only partially decellularize the tissue. For example it is beneficial to leave certain components of the whole tissue-specific within the center of the tissue disc (i.e. partially decellularized tissue disc).

In some instances, it is desirable to use a whole tissue that that has not been decellularized. For example, using a whole tissue-specific homogenate allows for the preservation of the in vivo environment including the preservation of endometrial epithelium, supportive stroma and vessels, as well as any secretions such as growth factors and cytokines that are normally present in the tissue in vivo.

In some instances, whole tissue can be lyophilized and processed into a fine powder. Preferably, the fine powder has a particle size about <40 µM. The fine powder can be sterilized using gamma irradiation thereby generating a sterile whole tissue particle. In some further instances, the sterile whole tissue particle is mixed with a desired culture medium and cultured with the appropriate cell type. In other instances, the sterile whole tissue particle is incorporated into a hydrogel and cultured with the appropriate cell type.

In some instances, the sterile whole tissue particles can be further processed. In some instances, whole tissue particles can be mechanically agitated. For example, particles can be mixed with culture medium and the resulting solution can be vortexed. In some instances, whole tissue particles can be chemically or enzymatically agitated. For example, tissue particles can be mixed with pepsin and hydrochloric acid. In some instances, the mechanically agitated or chemically/enzymatically agitated whole particle solutions can be centrifuged to form a supernatant and a particulate. The supernatant is known as the tissue-specific whole tissue extract, and the particulate is known as the tissue-specific whole tissue particulate. In some instances the whole tissue extract is substantially separated from the whole tissue particulate. In some instances the whole tissue extract is mixed with a desired culture medium and cultured with the appropriate cell type. In other instances, the whole tissue extract is incorporated into a hydrogel and cultured with the appropriate cell type. In some instances the whole tissue particulate is mixed with a desired culture medium and cultured with the appropriate cell type. In other instances, the whole tissue particulate is incorporated into a hydrogel and cultured with the appropriate cell type.

Culturing Cells

In one embodiment, the invention includes a tissue-specific ECM coating for cell culture that provides tissue-specific cues unlike traditional cell culture coatings, thereby enabling the culturing and maturation of a desired cell type. The tissue-specific ECM coating is applicable to any cell provided that the desired cell type is cultured with the matched tissue-specific ECM. A matched tissue-specific ECM is one that the cultured cell would normally be found in vivo or otherwise is the tissue of origin of the cell.

Cells may be isolated using techniques known to those skilled in the art. For example, the tissue can be cut into pieces, disaggregated mechanically and/or treated with digestive enzymes and/or chelating agents that weaken the connections between neighboring cells making it possible to disperse the tissue into a suspension of individual cells without appreciable cell breakage. If necessary, enzymatic dissociation can be accomplished by mincing the tissue and treating the minced tissue with any of a number of digestive enzymes either alone or in combination. These include but are not limited to, trypsin, chymotrypsin, collagenase, elastase, and/or hyaluronidase, DNase, pronase, and dispase. Mechanical disruption can also be accomplished using a number of methods including, but not limited to, scraping the surface of the tissue, the use of grinders, blenders, sieves, homogenizers, pressure cells, or insonators to name but a few.

Cell types include, but are not limited to, progenitor cells isolated from peripheral blood that can be induced to differentiate into different cells. Stem cells, committed stem cells, and/or differentiated cells may be used. Also, depending on the desired type of tissue or organ, specific types of committed stem cells can be used. For instance, myoblast cells can be used to build various muscle structures. Other types of committed stem cells can be used to make organs or organ-like tissue such as heart, kidney, liver, pancreas, spleen, bladder, cartilages, bone, brain, spine cord and peripheral nerve, ureter and urethra. Other cells include, but are not limited to, endothelial cells, muscle cells, smooth muscle cells, fibroblasts, osteoblasts, myoblasts, neuroblasts, fibroblasts, glioblasts; germ cells, hepatocytes, chondrocytes, keratinocytes, cardiac muscle cells, connective tissue cells, epithelial cells, endothelial cells, hormone-secreting cells, cells of the immune system, neurons, cells from the heart, kidney, liver, pancreas, spleen, bladder, cartilages, bone, brain, spine cord and peripheral nerve, ureter and urethra, and the like. In some embodiments it is not necessary to pre-select the type of stem cell that is to be used, because many types of stem cells can be induced to differentiate in an organ specific pattern once delivered to a given organ. For example, a stem cell delivered to the liver can be induced to become a liver cell simply by placing the stem cell within the biochemical environment of the liver.

Examples also include cells that have been genetically engineered, transformed cells, and immortalized cells. One example of genetically engineered cells useful in the present invention is a genetically engineered cell that makes and secretes one or more desired molecules. When the matrices comprising genetically engineered cells are implanted in an organism, the molecules produced can produce a local effect or a systemic effect, and can include the molecules identified above as possible substances.

Cells may produce substances that inhibit or stimulate inflammation; facilitate healing; resist immunorejection; provide hormone replacement; replace neurotransmitters; inhibit or destroy cancer cells; promote cell growth; inhibit or stimulate formation of blood vessels; augment tissue; and to supplement or replace the following tissue, neurons, skin, synovial fluid, tendons, cartilage, ligaments, bone, muscle, organs, dura, blood vessels, bone marrow, and extracellular matrix.

Culturing cells in the presence of the tissue-specific ECM of the invention, with or without components of a whole tissue-specific homogenate, provides the advantage that the tissue-specific ECM helps send signals to the cells to grow and reproduce in a specific type of desired way as normally would in an in vivo environment. Other factors and differentiation inducers may be added to the matrix to promote specific types of cell growth.

Once the tissue has been reduced to a suspension of individual cells, the suspension can be fractionated into subpopulations from which the cells elements can be obtained. This also may be accomplished using standard techniques for cell separation including, but not limited to, cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counterstreaming centrifugation), unit gravity separation, countercurrent distribution, electrophoresis and fluorescence-activated cell sorting. For example, salivary cells may be enriched by fluorescence-activated cell sorting. Magnetic sorting may also be used.

Cell fractionation may also be desirable, for example, when the donor has diseases such as cancer or tumor. A cell population may be sorted to separate the cancer or tumor cells from normal noncancerous cells. The normal noncancerous cells, isolated from one or more sorting techniques, may then be used for tissue reconstruction.

Isolated cells can be cultured in vitro to increase the number of cells available for seeding into the biocompatible substrate. To prevent an immunological response after implantation of the artificial tissue construct, the subject may be treated with immunosuppressive agents such as, cyclosporin or FK506.

Isolated cells may be transfected with a nucleic acid sequence. Useful nucleic acid sequences may be, for example, genetic sequences which reduce or eliminate an immune response in the host. For example, the expression of cell surface antigens such as class I and class II histocompatibility antigens may be suppressed. In addition, transfection can also be used for gene delivery. Cells may be transfected with specific genes prior to seeding onto the biocompatible substitute. Thus, the cultured cells can be engineered to express gene products that would produce a desired protein that helps ameliorate a particular disorder.

Methods for genetically engineering cells for example using retroviral vectors, adenoviral vectors, adeno-associated viral vectors, polyethylene glycol, or other methods known to those skilled in the art can be used. These include using expression vectors which transport and express nucleic acid molecules in the cells.

Vector DNA is introduced into prokaryotic or eukaryotic cells via conventional transformation or transfection techniques. Suitable methods for transforming or transfecting host cells can be found in Sambrook et al. Molecular Cloning: A Laboratory Manual, 2nd Edition, Cold Spring Harbor Laboratory press (2001), and other laboratory textbooks.

Once seeded onto the tissue-specific ECM of the invention, the cells proliferate and develop on the matrix to form a tissue layer. In some instances, because the matrix has an infra-structure that permits culture medium to reach the tissue layer, the cell population continues to grow, divide, and remain functionally active so that it can develop into a tissue that has a morphology which resembles the analogous structure in vivo.

It is important to recreate, in culture, the cellular microenvironment found in vivo for the particular tissue being engineered. By using the tissue-specific ECM of the invention that retains an infra-structure that is similar or the same as an in vivo tissue structure, the optimum environment for cell-cell interactions, cell-matrix interactions, development and differentiation of cell populations, is created.

Growth factors and regulatory factors can be added to the media to enhance, alter or modulate proliferation and cell maturation and differentiation in the cultures. The growth and activity of cells in culture can be affected by a variety of growth factors such as growth hormone, somatomedins, colony stimulating factors, erythropoietin, epidermal growth factor, hepatic erythropoietic factor (hepatopoietin), and like. Other factors which regulate proliferation and/or differentiation include prostaglandins, interleukins, and naturally-occurring chalones.

In another embodiment of the invention, the cells can be cultured following isolation without differentiation using standard cell culture media disclosed herein in the presence of the tissue-specific ECM, with or without components of a whole tissue-specific homogenate. Preferably, the cells can be passaged to at least five passages, and more preferably, the cells can be passaged to at least 10 passages or more. For example, the cells can be passaged to at least 15 passages, preferably at least 16 passages, more preferably at least 17 passages, yet more preferably at least 18 passages, preferably at least 19 passages or even at least 20 passages without losing their multipotentiality.

Any medium capable of supporting fibroblasts in cell culture may be used to culture the cells. Media formulations that support the growth of fibroblasts include, but are not limited to, Minimum Essential Medium Eagle, ADC-1, LPM (bovine serum albumin-free), F10 (HAM), F12 (HAM), DCCM1, DCCM2, RPMI 1640, BGJ Medium (with and without Fitton-Jackson Modification), Basal Medium Eagle (BME—with the addition of Earle's salt base), Dulbecco's Modified Eagle Medium (DMEM-without serum), Yamane, IMEM-20, Glasgow Modification Eagle Medium (GMEM), Leibovitz L-15 Medium, McCoy's 5A Medium, Medium M199 (M199E—with Earle's salt base), Medium M199 (M199H—with Hank's salt base), Minimum Essential Medium Eagle (MEM-E—with Earle's salt base), Minimum Essential Medium Eagle (MEM-H—with Hank's salt base) and Minimum Essential Medium Eagle (MEM-NAA with non-essential amino acids), and the like.

Additional non-limiting examples of media useful in the methods of the invention can contain fetal serum of bovine or other species at a concentration at least 1% to about 30%, preferably at least about 5% to 15%, most preferably about 10%. Embryonic extract of chicken or other species can be present at a concentration of about 1% to 30%, preferably at least about 5% to 15%, most preferably about 10%.

Another embodiment of the invention includes tissue-specific culture media comprising tissue-specific components. The tissue-specific culture media can comprise at least one of tissue-specific particles, tissue-specific extract, or tissue-specific particulate. The tissue-specific particles, tissue-specific extract, and tissue-specific particulate of the tissue-specific culture media, can be derived from decellularized tissue or whole tissue, as described elsewhere herein. The tissue-specific culture media can be used for the culturing of the appropriate cell type in two-dimensional or three-dimensional culturing. The tissue-specific culture media can be used to culture the appropriate cell type seeded in the tissue-specific ECM of the invention.

Tissue Engineering

The invention provides a tissue-specific ECM coating, with or without components of a whole tissue-specific homogenate, for cell culture that provides tissue-specific cues unlike traditional cell culture coatings, thereby enabling the culturing and maturation of a desired cell type. The tissue-specific ECM coating is applicable to any cell provided that the desired cell type is cultured with the matched tissue-specific ECM. A matched tissue-specific ECM is one that the cultured cell would normally be found in vivo or otherwise is the tissue of origin of the cell.

The tissue-specific ECM coating can comprise tissue-specific whole tissue particles or decellularized tissue particles. In another embodiment, the tissue-specific coating comprises tissue-specific whole tissue extract. In another embodiment, the tissue-specific coating comprises tissue-specific decellularized tissue extract. In another embodiment, the tissue-specific coating comprises tissue-specific whole tissue particulate. In another embodiment, the tissue-specific coating comprises tissue-specific decellularized tissue particulate.

The tissue-specific ECM coating of the invention can be used to coat two dimensional tissue culturing vessels. Non-limiting examples include tissue culturing vessels that are made from glass, polystyrene, or polypropylene. The tissue-specific ECM coating of the invention can also be used to coat tissue-specific ECMs of the invention. The tissue-specific ECM coating can be applied to a surface prior to contact with the appropriate cell type. The tissue-specific coating can be rinsed off the surface prior to contact with the appropriate cell type. Rinsing liquids include, but are not limited to, culture media, sterile water, PBS, or any other buffered solutions.

Preferred cell types include, but are not limited to, kidney cells, urothelial cells, mesenchymal stem cells bone marrow progenitor cells, smooth or skeletal muscle cells, myocytes (muscle stem cells), fibroblasts, chondrocytes, adipocytes, fibromyoblasts, and ectodermal cells, including dulctile and skin cells, hepatocytes, Islet cells, cells present in the intestine, and other parenchymous cells, osteoblasts and other cells forming bone, ligament, tendon, fibrocartilage, or cartilage.

The invention provides the ability to recreate, in culture, the cellular microenvironment found in vivo for a particular tissue being reconstructed. The invention provides a method in which a tissue-specific ECM of the invention, with or without components of a whole tissue-specific homogenate, is used as a three-dimensional scaffold to reconstruct an artificial tissue. By using a tissue-specific ECM that retains the properties of the native tissue (e.g., biochemical and mechanical properties), the tissue-specific ECM of the invention provides an scaffold for cell growth and proliferation which mimics cell growth an proliferation that occurs in vivo. By retaining a three-dimensional interstitial structure that is similar to an in vivo tissue, an optimum environment is created for cell-cell interactions, development and differentiation of cell populations.

In some embodiments, the tissue-specific ECM of the invention is a tissue-specific 3-D porous tissue disc. The 3-D porous tissue discs of the invention are derived from tissue-specific decellularized tissue, prepared by decellularizing, lyophilizing, and sterilizing biostructures as described elsewhere herein. The 3-D porous tissue discs can be cut to any size or thickness. In this embodiment, the tissue discs comprise a porous matrix.

In one embodiment, the tissue-specific ECM of the invention comprises a hydrogel. In another embodiment, the ECM comprises a tissue-specific decellularized tissue particle. In another embodiment, the ECM comprises a tissue-specific whole tissue particle. In another embodiment, the ECM comprises a tissue-specific decellularized tissue extract. In yet another embodiment, the ECM comprises a tissue-specific whole tissue extract. In another embodiment, the ECM comprises a tissue-specific decellularized tissue particulate. In yet another embodiment, the ECM comprises a tissue-specific whole tissue particulate.

Hydrogels can generally absorb a great deal of fluid and, at equilibrium, typically are composed of 60-90% fluid and only 10-30% polymer. In a preferred embodiment, the water content of hydrogel is about 70-80%. Hydrogels are particularly useful due to the inherent biocompatibility of the cross-linked polymeric network (Hill-West, et al., 1994, Proc. Natl. Acad. Sci. USA 91:5967-5971). Hydrogel biocompatibility can be attributed to hydrophilicity and ability to imbibe large amounts of biological fluids (Brannon-Peppas. Preparation and Characterization of Cross-linked Hydrophilic Networks in Absorbent Polymer Technology, Brannon-Peppas and Harland, Eds. 1990, Elsevier: Amsterdam, pp 45-66; Peppas and Mikos. Preparation Methods and Structure of Hydrogels in Hydrogels in Medicine and Pharmacy, Peppas, Ed. 1986, CRC Press: Boca Raton, Fla., pp 1-27). The hydrogels can be prepared by crosslinking hydrophilic biopolymers or synthetic polymers. Examples of the hydrogels formed from physical or chemical crosslinking of hydrophilic biopolymers, include but are not limited to, hyaluronans, chitosans, alginates, collagen, dextran, pectin, carrageenan, polylysine, gelatin or agarose. (see: W. E. Hennink and C. F. van Nostrum, 2002, Adv. Drug Del. Rev. 54, 13-36 and A. S. Hoffman, 2002, Adv. Drug Del. Rev. 43, 3-12). These materials consist of high-molecular weight backbone chains made of linear or branched polysaccharides or polypeptides. Examples of hydrogels based on chemical or physical crosslinking synthetic polymers include but are not limited to (meth)acrylate-oligolactide-PEO-oligolactide-(meth)acrylate, poly(ethylene glycol) (PEO), poly(propylene glycol) (PPO), PEO-PPO-PEO copolymers (Pluronics), poly(phosphazene), poly(methacrylates), poly(N-vinylpyrrolidone), PL(G)A-PEO-PL(G)A copolymers, poly(ethylene imine), etc. (see A. S Hoffman, 2002 Adv. Drug Del. Rev, 43, 3-12). In some embodiments, the transparent hydrogel scaffold comprises poly(ethylene glycol) diacrylate (PEGDA).

Hydrogels closely resemble the natural living extracellular matrix (Ratner and Hoffman. Synthetic Hydrogels for Biomedical Applications in Hydrogels for Medical and Related Applications, Andrade, Ed. 1976, American Chemical Society: Washington, D.C., pp 1-36). Hydrogels can also be made degradable in vivo by incorporating PLA, PLGA or PGA polymers. Moreover, hydrogels can be modified with fibronectin, laminin, vitronectin, or, for example, RGD for surface modification, which can promote cell adhesion and proliferation (Heungsoo Shin, 2003, Biomaterials 24:4353-4364; Hwang et al., 2006 Tissue Eng. 12:2695-706). Indeed, altering molecular weights, block structures, degradable linkages, and cross-linking modes can influence strength, elasticity, and degradation properties of the instant hydrogels (Nguyen and West, 2002, Biomaterials 23(22):4307-14; Ifkovits and Burkick, 2007, Tissue Eng. 13(10):2369-85).

Hydrogels can also be modified with functional groups for covalently attaching a variety of proteins (e.g., collagen) or compounds such as therapeutic agents. Therapeutic agents which can be linked to the matrix include, but are not limited to, analgesics, anesthetics, antifungals, antibiotics, anti-inflammatories, anthelmintics, antidotes, antiemetics, antihistamines, antihypertensives, antimalarials, antimicrobials, antipsychotics, antipyretics, antiseptics, antiarthritics, antituberculotics, antitussives, antivirals, cardioactive drugs, cathartics, chemotherapeutic agents, a colored or fluorescent imaging agent, corticoids (such as steroids), antidepressants, depressants, diagnostic aids, diuretics, enzymes, expectorants, hormones, hypnotics, minerals, nutritional supplements, parasympathomimetics, potassium supplements, radiation sensitizers, a radioisotope, sedatives, sulfonamides, stimulants, sympathomimetics, tranquilizers, urinary anti-infectives, vasoconstrictors, vasodilators, vitamins, xanthine derivatives, and the like. The therapeutic agent can also be other small organic molecules, naturally isolated entities or their analogs, organometallic agents, chelated metals or metal salts, peptide-based drugs, or peptidic or non-peptidic receptor targeting or binding agents. It is contemplated that linkage of the therapeutic agent to the matrix can be via a protease sensitive linker or other biodegradable linkage. Molecules which can be incorporated into the hydrogel matrix include, but are not limited to, vitamins and other nutritional supplements; glycoproteins (e.g., collagen); fibronectin; peptides and proteins; carbohydrates (both simple and/or complex); proteoglycans; antigens; oligonucleotides (sense and/or antisense DNA and/or RNA); antibodies (for example, to infectious agents, tumors, drugs or hormones); and gene therapy reagents.

In one embodiment of the invention, the tissue-specific ECM is a type I collagen hydrogel. In another embodiment of the invention, the tissue-specific ECM is a hyaluronic acid (HA) based hydrogel. In one embodiment, the hyaluronic acid is conjugated with heparin, thereby forming a HP hydrogel.

In certain embodiments, one or more multifunctional cross-linking agents may be utilized as reactive moieties that covalently link biopolymers or synthetic polymers. Such bifunctional cross-linking agents may include glutaraldehyde, epoxides (e.g., bis-oxiranes), oxidized dextran, p-azidobenzoyl hydrazide, N-[α.-maleimidoacetoxy]succinimide ester, p-azidophenyl glyoxal monohydrate, bis-[β-(4-azidosalicylamido)ethyl]disulfide, bis[sulfosuccinimidyl]suberate, dithiobis[succinimidyl proprionate, disuccinimidyl suberate, 1-ethyl-[β-dimethylaminopropyl]carbodiimide hydrochloride (EDC), N-hydroxysuccinimide (NHS) and other bifunctional cross-linking reagents known to those skilled in the art.

In another embodiment utilizing a cross-linking agent, polyacrylated materials, such as ethoxylated (20) trimethylpropane triacrylate, may be used as a non-specific photoactivated cross-linking agent. Components of an exemplary reaction mixture would include a thermoreversible hydrogel held at 39° C., polyacrylate monomers, such as ethoxylated (20) trimethylpropane triacrylate, a photo-initiator, such as eosin Y, catalytic agents, such as 1-vinyl-2-pyrrolidinone, and triethanolamine. Continuous exposure of this reactive mixture to long-wavelength light (>498 nm) would produce a cross-linked hydrogel network The stabilized cross-linked hydrogel matrix of the present invention may be further stabilized and enhanced through the addition of one or more enhancing agents. By "enhancing agent" or "stabilizing agent" is intended any compound added to the hydrogel matrix, in addition to the high molecular weight components, that enhances the hydrogel matrix by providing further stability or functional advantages. Suitable enhancing agents, which are admixed with the high molecular weight components and dispersed within the hydrogel matrix, include many of the additives described earlier in connection with the thermoreversible matrix discussed above. The enhancing agent can include any compound, especially polar compounds, that, when incorporated into the cross-linked hydrogel matrix, enhance the hydrogel matrix by providing further stability or functional advantages.

Preferred enhancing agents for use with the stabilized cross-linked hydrogel matrix include polar amino acids, amino acid analogues, amino acid derivatives, intact collagen, and divalent cation chelators, such as ethylenediaminetetraacetic acid (EDTA) or salts thereof. Polar amino acids are intended to include tyrosine, cysteine, serine, threonine, asparagine, glutamine, aspartic acid, glutamic acid, arginine, lysine, and histidine. The preferred polar amino acids are L-cysteine, L-glutamic acid, L-lysine, and L-arginine. Suitable concentrations of each particular preferred enhancing agent are the same as noted above in connection with the thermoreversible hydrogel matrix. Polar amino acids, EDTA, and mixtures thereof, are preferred enhancing agents. The enhancing agents can be added to the matrix composition before or during the crosslinking of the high molecular weight components.

The enhancing agents are particularly important in the stabilized cross-linked bioactive hydrogel matrix because of the inherent properties they promote within the matrix. The hydrogel matrix exhibits an intrinsic bioactivity that will become more evident through the additional embodiments described hereinafter. It is believed the intrinsic bioactivity is a function of the unique stereochemistry of the cross-linked macromolecules in the presence of the enhancing and strengthening polar amino acids, as well as other enhancing agents.

The tissue-specific ECM of the invention, with or without components of a whole tissue-specific homogenate, can be pre-treated with agents prior to perfusion of cultured cells in order to enhance the attachment of cultured cell populations to the tissue-specific ECM. For example, the tissue-specific ECM of the invention can be treated with collagens, elastic fibers, reticular fibers, glycoproteins, glycosaminoglycans (e.g., hyaluronic acid or its analogs, heparin, heparan sulfate, chondroitin-4-sulfate, chondroitin-6-sulfate, dermatan sulfate, keratin sulfate, etc.)

Additional populations of cultured cells, such as parenchymal cells, can be perfused onto the tissue-specific ECM, with or without components of a whole tissue-specific homogenate. Parenchyma cells perfused onto the tissue-specific ECM can be incubated to allow the cells to adhere to the tissue-specific ECM. The parenchyma cells can be cultured in vitro in culture medium to allow the cells to grow and develop until the cells resemble a morphology and structure similar to that of the native tissue.

The tissue-specific ECM of the invention can be used for the culturing of the appropriate cell type in a three-dimensional environment. The appropriate cell type can be seeded on the surface of the tissue-specific ECM. Alternatively, the cells can be perfused within the tissue-specific ECM constructs. These cells can adhere to the tissue-specific constructs of the invention, and grow and multiply throughout the construct. The tissue-specific ECM construct supports the appropriate functionality of the seeded cells. After in vitro culture of cells within the tissue-specific ECM constructs for an appropriate time, wherein the cells display appropriate functionality, the construct may be used as a model system for the screening of therapeutic compounds. Non-limiting examples of assays that may be used with such a model system include the effect of potential compounds on cell viability, metabolism, differentiation, proliferation, and mutagenesis. The constructs can also be seeded with cells derived or isolated from a disease state (e.g. a transgenic animal or diseased patient), thus creating a model system that replicates the disease state. As such, this model system can be used in experiments investigate the mechanism of the disease state. Further, such a model system can be used in assays that evaluate the effect of potential therapeutic compounds on cell survival and disease progression.

The methods and compositions of the invention can be used to replace, or repair a structural component in the subject such as ligaments, tendons, cartilage, joints, and bones. The methods and compositions of the invention can be used to create artificial tissue such as kidney, liver, bladder, skin, and the like.

In one embodiment, the invention provides a reconstituted artificial organ or tissue generated by contacting a tissue-specific ECM of the invention with a population of regenerative cells. Regenerative cells as used herein are any cells used to recellularize a tissue-specific ECM of the invention. Regenerative cells can be totipotent cells, pluripotent cells, multipotent cells, mature or immature cells, and can be uncommitted or committed. Regenerative cells also can be single-lineage cells alone or in combination. In addition, regenerative cells can be undifferentiated cells, partially differentiated cells, or fully differentiated cells. Regenerative cells as used herein include embryonic stem cells. Regenerative cells also include progenitor cells, precursor cells, and "adult" derived stem cells including umbilical cord cells and fetal stem cells. Regenerative cells further include adult organ cells of non-stem or progenitor cells types, such as vascular and parenchymal cells, and inducible pluripotent stem cells. In one embodiment, combinations of different cells, or cell "cocktails" containing different cell population types, can be employed to reconstruct the target organ or tissue.

Examples of regenerative cells that can be used to recellularize include, without limitation, embryonic stem cells, inducible pluripotent stem cells, umbilical cord blood cells, tissue-derived stem or progenitor cells, bone marrow-derived stem or progenitor cells, blood-derived stem or progenitor cells, mesenchymal stem cells (MSC), skeletal muscle-derived cells, adipose-derived stem or progenitor cells, multipotent adult progenitor cells (MAPC), multipotent adult stem cells, amniotic fluid-derived cells, or urine-derived cells. Additional regenerative cells that can be used include cardiac stem cells (CSC), multipotent adult cardiac-derived stem cells, cardiac fibroblasts; cardiac microvasculature endothelial cells, or aortic endothelial cells. Bone marrow-derived stem cells such as bone marrow mononuclear cells (BM-MNC), stromal cells, endothelial or vascular stem or progenitor cells, and peripheral blood-derived stem cells such as endothelial progenitor cells (EPC) also can be used as regenerative cells. It may also be possible to use bone cells, bone marrow cells, neural and spinal cord cells, blood, fat, neural cells from tissue, liver, skin, heart, and the like. Any organ or tissue derived cells including primary cells may be possible to use.

The number of regenerative cells that is introduced into and onto a tissue-specific ECM of the invention in order to generate an organ or tissue is dependent on both the organ (e.g., which organ, the size and weight of the organ) or tissue and the type and developmental stage of the regenerative cells. Different types of cells may have different tendencies as to the population density those cells will reach. Similarly, different organ or tissues may be cellularized at different densities. By way of example, a decellularized organ or tissue can be "seeded" with at least about 1,000 (e.g., at least 10,000; 100,000, 1,000,000, 10,000,000, or 100,000,000) regenerative cells; or can have from about 1,000 cells/mg tissue (wet weight, i.e., prior to decellularization) to about 10,000,000 cells/mg tissue (wet weight) attached thereto.

During recellularization, an organ or tissue is maintained under conditions in which at least some of the regenerative cells can reside, multiply and/or differentiate within and on the tissue-specific ECM of the invention. Those conditions include, without limitation, the appropriate temperature and/or pressure, electrical and/or mechanical activity, force, the appropriate amount of $O_2$ and/or $CO_2$, an appropriate amount of humidity, and sterile or near-sterile conditions. During recellularization, the tissue-specific ECM of the invention and the regenerative cells attached thereto are maintained in a suitable environment. For example, the regenerative cells may require a nutritional supplement (e.g., nutrients and/or a carbon source such as glucose), exogenous hormones or growth factors, and/or a particular pH.

In some instances, an organ or tissue generated by the methods described herein is to be transplanted into a patient. In those cases, the regenerative cells used for tissue engineering can be obtained from the patient such that the regenerative cells are "autologous" to the patient. Regenerative cells from a patient can be obtained from, for example, blood, bone marrow, tissues, or organs at different stages of life (e.g., prenatally, neonatally or perinatally, during adolescence, or as an adult) using methods known in the art. Alternatively, regenerative cells used for tissue engineering can be syngeneic (i.e., from an identical twin) to the patient. Regenerative cells can be allogeneic to the patient from, for example, a non-HLA-matched donor.

Irrespective of the source of the regenerative cells (e.g., autologous or not), the decellularized solid organ can be autologous, allogeneic or xenogeneic to a patient. In certain instances, a tissue-specific ECM of the invention may be recellularized with cells in vivo (e.g., after the organ or tissue has been transplanted into an individual).

The progress of regenerative cells can be monitored during recellularization. The amount of differentiation that regenerative cells have undergone can be monitored by determining whether or not various markers or functions are present in a cell or a population of cells. Markers associated with different cells types and different stages of differentiation for those cell types are known in the art, and can be readily detected using antibodies, metabolic profiles, standard immunoassays, metabolic capabilities, physiological responses, etc. Nucleic acid assays as well as morphological and/or histological evaluation can be used to monitor recellularization as can organ function.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: 3-D Liver Tissue-Specific Extracellular Matrix for Hep G2 Cell Growth The following results are based on the observation that decellularization/oxidation procedures provide an optimal 3-D biological collagen matrix with high porosity and increased pore size with minimal retention of cellular components. The present invention is based on the discovery that each cell type grew best (cell proliferation and differentiation) when cultured on an extracellular matrix (ECM) derived from the same tissue origin as the cell.

Experiments were designed to further expand the development of such matrices for use in the expansion of human primary hepatocytes. Experiments were also designed to evaluate the interactions between hepatocyte and liver specific ECM with 3-D structure and their role in long-term expansion and functional maintenance of human hepatocytes. The feasibility of developing 3-D liver ECM culture disks was also evaluated. For example, it was investigated whether tissue-specific 3-D porous ECM derived from porcine liver could facilitate liver cell line (Hep G2) expansion and cell-matrix infiltration in a dynamic culture.

To obtain the liver ECM, 15 fresh livers were harvested from adult swine. Porcine liver lobes were sliced to 3 mm thickness. To generate liver ECM disks for HepG2 cell culture, the sliced liver tissues were cut into 1 cm discs to fit 24-well plates. Four methods were used to decellularize liver ECM (see Table 1). To enhance decellularization in each of the steps described, the bottles for washing the tissue samples were set onto a rotating shaker at 4° C. Each solution was changed 2-3 times a day. The decellularized liver samples were placed into 24-well plates, lyophilized, and sterilized with gamma irradiation.

HepG2 cells ($1 \times 10^6$) were seeded onto each disc. Then, 2 ml of culture medium was added slowly to the edge of the well, taking care not to dislodge cells from the scaffold. The scaffolds were cultured under static or 3-D dynamic conditions. Hep G2 cells were seeded on liver ECM scaffolds and culture dishes as a control for 14 days. Histological staining, cell proliferation testing, immunocytochemistry, Western blot analysis, and hepatocyte functional analysis were carried out.

It was observed that decellularization/oxidation procedures removed up to 95% of cellular compounds and preserved several key molecular composition complexes of ECM, i.e. collagen I-V, proteoglycans and glycosaminoglycans, fibronectin and laminin, and fabricated 3-D liver ECM discs with micro-architecture (porous sizes arranged from 20-100 µm). Uniform multi-layers of Hep G2 cells were formed on liver ECM discs, and cells exhibited more infiltration into the ECM under a dynamic culture. Human hepatocytes expressed albumin and p450 proteins up to 14 days after seeding on a liver ECM matrix.

The results presented herein demonstrate that 3-D porous ECM derived from porcine liver was optimized for culturing liver cells. It was observed that 3-D liver ECM retained the liver ECM compounds using method 1 as described in Table 1. The liver-specific ECM composition, micro-structure and dynamic culture conditions together facilitated 3-D growth of hepatocytes and cell-matrix infiltration and supported the long-term maintenance of phenotype and functionality of human hepatocytes.

Without wishing to be bound by any particular theory, it is believed that the 3-D liver ECM biomaterials can be applicable to cell- and tissue-based therapies, and efficient industrial scale-up for drug and toxicology testing to reduce use of animals in research.

TABLE 1

Four methods for decellularization of liver ECM

| | |
|---|---|
| Method 1 | Distilled water for 3 days, 1% Triton1 and 0.1% ammonium hydroxide in distilled water for 5 days, distilled water for 3 days at 4 C.° |
| Method 2 | 3.4M NaCl for 30 min., PBS 3 days, DNase/RNase for 3 hrs, 1% Triton1X-100 for 3 hrs, PBS wash for 3 days |
| Method 3 | PBS for 3 days, 1% Triton1X-100 for 3 days, 0.04% ammonium hydroxide for 1 day, PBS for 3 days |
| Method 4 | 3.4M NaCl for 30', PBS for 3 days, DNase/RNase for 3 hrs, 1% Triton1X-100 for 3 hrs, 1.6% PAA for 3 hrs, PBS for 3 days |

Example 2: 3-D Tissue Gel Model for Hepatocyte Culture in Drug Development

Liver tissue displays robust regeneration capability when damaged or injured. However, when liver cells are cultured on 2-D plastic platforms in vitro, these cells quickly lose most of their function. Without wishing to be bound by any particular theory, it is believed that the novel culture system of the invention relating to a 3-D liver tissue gel that contains and preserves growth factors, cytokines, and extracellular compounds derived from the liver tissue provide a favorable environment for liver tumor cells (Hep G2) or normal human hepatocyte growth, and maintain liver function in vitro.

Experiments were designed to determine whether a tissue gel derived from pig liver is non-toxic to cell growth in vitro and is biocompatible. The effect of 3-D liver tissue (LT) gel on maintaining liver function of hepatocytes in vitro for potential use in drug screen and liver tissue regeneration was assessed. Briefly, Hep G2 carcinoma cells, McArdle RH777 Red cells, and human primary hepatocytes were used to assess cell proliferation, cell viability and functionality. Fresh porcine liver tissues were minced, lyophilized for 24 hrs, ground into fine powder (particle size <40 µm) and sterilized with gamma irradiation. Liver tissue particulates were mixed with collagen type I gel. Eight different treatments were tested in this study, including 2-D plastic (negative control); 2-D collagen coating, 2-D liver tissue particle coating; 3-D collagen I gel and 3D Matrigel as control; and 3-D liver tissue gel (1 mg/ml). Hep G2 cells ($2 \times 10^4$/well) were seeded onto the surface of 2-D gels, and ($4 \times 10^4$) Hep G2 cells were cultured into 3-D gel for 14 days. Using Alamar Blue, cellular growth was analyzed every other day through the second week of cultivation. Morphology and cell-matrix interactions within the 3-D gel structure were evaluated histologically.

Figure 2:
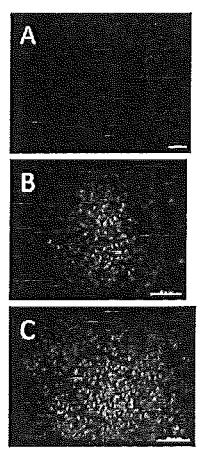
FIG. 2, comprising

A significant difference in morphology and cell proliferation was observed between 2-D plastic and 3-D gel matrix. Hep G2 cells grew rapidly and formed a flat monolayer on 2-D plastic treatments; they formed 3-D aggregated clusters typical of tumor growth in vivo when grown into 3-D gel matrices (FIG. 1). The majority of Hep G2 cells survive in 3-D tissue gel for 14 days (FIG. 2). McArdle RH777 Red cells and human primary hepatocytes displayed growth patterns similar to Hep G2 cells.

The results presented herein demonstrate that the liver tissue gel was not cytotoxic. Cell viability on 3-D and plastic-treated dishes was approximately the same. Furthermore, 3-D liver tissue gel models proved to be sufficient to sustain Hep G2 cellular growth. The 3-D models allowed the cells to grow as is typical in the in vivo environment. Without wishing to be bound by any particular theory, it is believed that the matrices and models of the invention can be used to evaluate cell growth and differentiation of human primary hepatocytes for drug development.

Example 3: Chondrogenic Differentiation of Urine Derive Stem Cells within 3-D Tissue Gel for Cartilage Tissue Engineering Fresh cartilage tissue contains vital growth factors, cytokines, and extracellular matrix that might provide a favorable environment for chondrogenic differentiation of stem cells. It has previously been demonstrated that urine-derived stem cells (USC) can differentiate into several mesoderm cell lineages, including chondrocytes. The following experiments were designed to fabricate a tissue-engineered ear with chondroctye-differentiated USC in vitro, which could be used in auricular construction.

Briefly, in order to prepare the applicable "powder", skin from fresh pig ear was removed, leaving only cartilage. The cartilage tissue was washed in chilled Dulbecco's Phosphate Buffered Saline (PBS) and minced into 1×1 mm pieces. The tissue was then flash-frozen in liquid nitrogen and lyophilized for 2 days. The lyophilized tissue was ground into powder using the 6478 Grinder Mill. Next the tissue was gamma radiated using 1 kilorad. This cartilage tissue powder was mixed with collagen type I gel.

The treatments in this study included plastic (negative control), 2-D gel, and 3-D gel. The 2-D gel was separated into 3 different treatments, i.e. 2-D collagen, 2-D collagen plus cartilage tissue powder (dissolved into medium), and 2-D collagen plus liver powder supernatant (dissolved into PBS). The 2-D was left to dry overnight in sterilized conditions. The 3-D gel had four different treatments, i.e. 3-D collagen, 3-D collagen plus liver powder, 3-D collagen plus liver powder supernatant, and 3-D Matrigel. Final concentrations of collagen, cartilage tissue powder, and tissue powder extract were all 1 mg/ml.

For cell seeding experiments, USC cells ($2 \times 10^4$/well) were seeded onto the surface of 2-D gels, and USC cells ($4 \times 10^4$/well) were seeded in DMEM 10% FBS into 3-D gel mixtures with a cultivation period of 14 days. Morphology and cell proliferation were analyzed on Day 1, 3, 7, and day 9 of the 2-week cultivation period. Following the 2-week cultivation period, cells were stained with chondrocyte-specific makers (such as Safranin 0) to determine differentiation.

Figure 3:
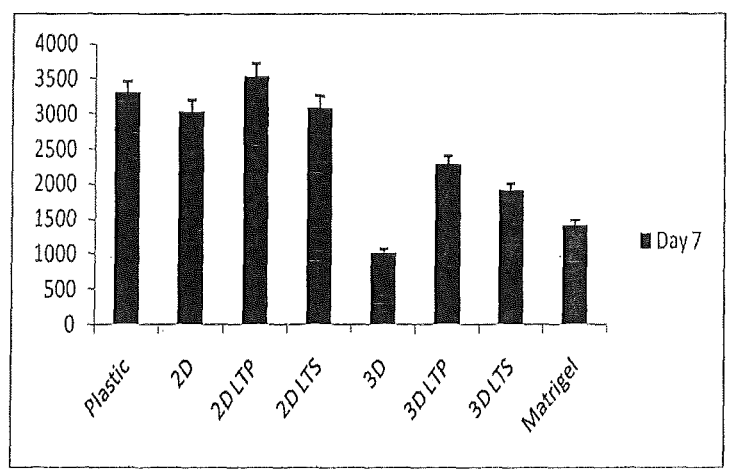
FIG. 3 is an image depicting cell proliferation analysis taken on Day 7 of cultivation.
Figure 4:
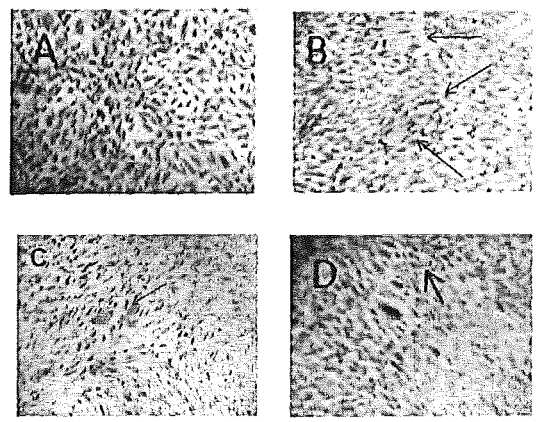
FIG. 4, comprising
Figure 5:
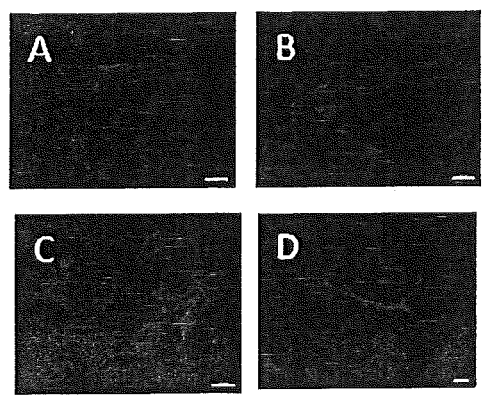
FIG. 5, comprising

Although USC typically grew quicker in 2-D plastic dishes (FIG. 3), it was observed that chondrogenic differentiation of USC was remarkably enhanced in 3-D tissue gel and cartilage tissue extract treatment (FIG. 4). It was also observed that cartilage tissue gel and its tissue extract was not cytotoxic to the cells.

The results presented herein suggest that cartilage tissue gel or its tissue extract could induce USC to differentiate into chondrocytes. These tissue products were not cytotoxic. Without wishing to be bound by any particular theory, the cartilage tissue gel or its tissue extract can be used to differentiate USCs of for that matter any progenitor or stem cell for cartilage tissue engineering, such as ear construction.

Example 4: 3-D Tissue Gel for Skeletal Muscle Cell Growth and Functional Maintenance The present study was designed to maintain the phenotypes and functionality of skeletal muscle cells for use in skeletal muscle regeneration for trauma and muscular dystrophy. As a non-limiting example, cells were cultured within a 3-D tissue gel derived from pig muscle.

Briefly, in order to prepare a skeletal muscle 3-D model, fresh porcine skeleton muscle tissues were minced, lyophilized for 24 hrs, ground into fine powder (particle size <40 μm) and sterilized with gamma irradiation. Skeleton muscle tissue particulates were mixed with collagen type I gel. Collagen gel was neutralized with NaOH, F12, and NaHCO$_3$ prior to cell seeding. The neutralized gel was premixed with medium and tsp of the desired powder (e.g., skeletal muscle powder). Once thoroughly mixed, the cells were added to collagen and aliquoted into a 24-well plate. The final cell concentration in each well was $4 \times 10^4$ cells/well.

In order to assess cell proliferation, Alamar Blue (Invitrogen), a nontoxic cell growth agent, was added to the cells every other day for 2 weeks. Prior to Alamar Blue treatment, old medium was extracted from gel and 1 ml of fresh PBS and mounted with DAPI nuclear stain. Photos were taken on the Leica Upright Microscope using magnifications 200× and 400×.

It was observed that myotube formation (linkage of nuclei to form a 3-D tubular structure) occurred more rapidly in the 3-D tissue gel compared to plastic-treated cells, assessed by rhodamine phalloidin and skeletal muscle cell-specific markers. 3-D skeletal muscle tissue (SMT) had the greatest myotubule formation, which is directly linked to the increased contractility ratio. Cell-gel matrix contractility was directly correlated with myotubule formation. Proliferation of skeletal muscle cells indicates that muscle tissue gel is not cytotoxic.

The results presented herein demonstrate that 3-D tissue gel provided a benign environment for maintaining myogenic function of skeletal muscle cells. Skeletal muscle tissue gel was proved to be safe for muscle cell culture without inducing cell toxicity. Without wishing to be bound by any particular theory, the skeletal muscle tissue gels can be used in skeletal muscle regeneration for massive soft tissue trauma and muscular dystrophy.

Example 5: Types of Applications on Tissue-Specific Biomaterials

The results presented herein demonstrate that the tissue-specific ECM can be used in different applications of cell culture. Table 2 discloses representative types of applications that can be used by the tissue-specific ECM.

TABLE 2

| Types of applications on tissue-specific biomaterials for cell culture | |
|---|---|
| 2.5 D tissue particle coating | 1. Mixed sterile tissue particles either with culture medium as "Muddy" solution or collagen gel; <br> 2. Bushed the solution on the culture plate and let them dry out. <br> 3. Seeded the relative cells on the surface of 2.5-D coatings |
| 3-D Culture Gel | 1. Mixed sterile tissue particles with collagen I gel as 3-D tissue gel; <br> 2. Either mixed the cells with this 3-D tissue gel or seeded the cells on the top of the 3-D tissue gel |
| 3-D porous tissue discs (different from tissue ECM discs) | 1. Decellularized tissue discs with distill water for 3 days; <br> 2. Most of cell compounds on tissue discs were washed away to make porous surface; <br> 3. Certain cell compounds within the center of tissue discs are still remaining; <br> 4. seeded cells on the top of tissue discs |
| Tissue extract supernate | 1. Mixed sterile tissue particles with culture medium very well with vortexer for 10-15 minutes; <br> 2. Resuspended the tissue particular solution; <br> 3. aspirate the supernate from the tissue particular solution for feeding the cells | medium was added. Samples incubated for 18 hrs. Samples were read using fluorescence on the Spectra Max microplate reader.

For contractility assessment, 3-D skeleton muscle-collagen gel matrices were contracted and prefixed in 10% formalin for 1 hr. Gels were washed three times in Dulbecco's Phosphate Buffered Saline (PBS). Gels were removed from dish using a set of forceps and laid out into a 10 cm dish. Using a Prometix ruler, gels were measured accordingly.

For immunocytochemistry analysis, cells were stained with rhodamine phalloidin, which stains the actin-filled cytoskeleton; and 4 skeletal muscle markers (MyoD, Myogenin, Myosin, and Myf5). Prior to treatment 3-D gels were fixed in 10% formalin for 30 minutes. The antibody incubation period was 1hr. Following staining, gel was washed in Without wishing to be bound by any particular theory, the tissue-specific ECM of the invention has a myriad of useful applications for culturing cells. The cells cultured in the presence of the tissue-specific ECM may be used in therapeutic methods for alleviating or treating tissue defects in an individual. The cells in combination with the tissue-specific ECM may also be used in vitro or in vivo to identify therapeutic compounds and therefore may have therapeutic potential.

In the context of drug screening, the cell cultures can be maintained in vitro in the presence of the tissue-specific ECM and exposed to the compound to be tested. The activity of a compound can be measured by its ability to damage or kill cells in culture. This may readily be assessed by vital staining techniques. The effect of growth/regulatory factors may be assessed by analyzing the cellular content of the matrix, e.g., by total cell counts, and differential cell counts. This may be accomplished using standard cytological and/or histological techniques including the use of immunocytochemical techniques employing antibodies that define type-specific cellular antigens.

Example 6: Tissue Specific Synthetic ECM Hydrogels for In Vitro Maintenance of Hepatocyte Function The following experiments were designed to investigate whether extracts prepared from whole liver or decellularized liver could be supplemented into collagen Type I, hyaluronic acid (HA), or heparin-conjugated HA (HP) hydrogels to enhance survival, expansion and function of hepatocytes. First, liver-specific hydrogels were prepared by incorporating extracts from whole liver tissue (LTE) or decellularized liver ECM (LEE) into the hydrogels prior to gelation. The compositions of the liver tissue and ECM extracts were analyzed by colorimetric assays for GAG, collagen, and elastin content. Second, biocompatibility of these materials was confirmed with culture of HEPG2 cells, and morphological differences were noted between LTE and LEE treatments. Finally, primary hepatocytes were maintained in sandwich-style hydrogel cultures for 4 weeks and analyzed for morphological characteristics and functionality by way of ELISA for albumin, urea colorimetric assays, albumin IHC, and cytochrome p450-dependent drug metabolism activity. Plastic controls resulted in poor viability and functionality over time. Collagen gels supported relatively consistent functional behavior over time, but cell morphology and mitochondrial metabolism dropped off near the end of the experiment. Hepatocytes cultured in HA and HP hydrogels were highly dependent on incorporation of LTE or LEE in the hydrogels. Hepatocyte mitochondrial metabolism increased in all HA and HP groups from week 1 to week 4. In these groups viability was maintained and mitochondrial metabolism increased over the 4 weeks. Hepatocytes cultured in HP hydrogels containing LEE secreted consistent levels of albumin and urea. Immnunohistochemistry showed that the same groups stained strongest for albumin. Furthermore HP hydrogels containing either LEE or LTE supported hepatocytes with increased cytochrome p450-dependent drug metabolism of ethoxycoumarin.

These results presented herein demonstrate that the combination of HA-based biomaterials conjugated with heparin containing liver-specific ECM can be a system useful for liver tissue engineering and drug discovery research. Customizing heparinized HA hydrogels with liver-specific ECM components is an efficient method for building primary human hepatocyte-based tissue for hepatocyte expansion and in vitro drug and toxicology screening purposes.

The materials and methods employed in these experiments are now described.
Materials and Methods
Decellularization of 3-D Porous Liver Scaffolds Fresh porcine livers (Disher Packing, Inc., Yadkinville, N.C.) were pre-rinsed through the hepatic portal vein with chilled Dulbecco's Phosphate Buffered Saline (DPBS). The liver was cut into 7.6 cm by 10.2 cm blocks and placed in plastic containers. Blocks were flash frozen at −80° C. Frozen liver blocks were sectioned into 3 mm slices. Slices (6-10) were transferred to 500 ml distilled water and shook on a rotary shaker at 200 rpm for 3 days at 4° C., during which water was changed three times per day. The liver slices were treated with 2% Triton X-100 for 4 days followed by 2% TX-100+0.1% NH$_4$OH for 24 hr. During the TX-100 rinses, solutions were changed twice daily. The decellularized liver tissues were washed for 2 additional days in distilled water to remove any traces of TX-100. Decellularized liver scaffolds were stored at 4° C. until further use.

Preparation of Tissue and ECM Digest

Fresh liver tissues and decellularized liver ECMs were lyophilized for 48 hr. Following lyopholization, samples were powderized. One gram of liver tissue or liver ECM powder was mixed with 100 mg Pepsin (Porcine gastric mucosa, 3400 units of protein) and sterilized by gamma irradiation (1 Mrad). All subsequent procedures following sterilization were carried out under sterile conditions. Hydrochloric acid was added to the sterilized materials and incubated for 48 hrs at room temperature. The resulting mixture was transferred to a 50 ml conical tube and centrifuged at 3000 rpm for 15 minutes. The supernatant was removed. This was repeated 3 times until the supernatant was clear. To ensure there was no more particulate matter remaining, the suspension was filtered through a 0.2 um syringe filter. The resulting liver decellularized ECM extract (LEE) and liver tissue extracts (LTE) were stored at −80° C. until further use.

Collagen and Hyaluronic Acid Liver ECM and Liver Tissue Gel Preparation

Type I rat tail collagen was diluted to 1 mg/mL in PBS and adjusted to pH 7.0 by 1M NaOH. LEE and LTE solutions (1 mg/ml) were also adjusted to pH 7.0 by 1M NaOH. Collagen only gels (COL) were formed by mixing the prepared collagen solution with William's E Media 1:1 by volume. Collagen with LEE or LTE gels (COL+EG and COL+TG, respectively) were formed by mixing the collagen solution with LEE or LTE 1:1 by volume. Gels were allowed to crosslink for 1 hr before use.

For HA and HP gels, Extracel and Extracel-HP (Glycosan Biosystems, Alameda, Calif.) components were dissolved in sterile water. Briefly, Glycosil (for HA gels), Heprasil (for HP gels), and Gelin-S were dissolved in water to make 2% w/v solutions. Extralink, the crosslinker, was dissolved in water to make a 4% w/v solution. For HA-only and HP-only gels, Glycosil (or Heprasil), Gelin-S, and Extralink were mixed 2:2:1 by volume. The resulting solution was mixed 1:1 with additional water. For gels containing LEE or LTE (HA+EG, HA+TG, HP+EG, and HP+TG), LEE or LTE were substituted for the water in final mixing step. Solutions were allowed to crosslink for 30 min before use.

HEPG2 Biocompatibility

To assess substrate biocompatibility, gels were prepared as described elsewhere herein. Additionally, tissue culture plastic (P) was used as a control, and LEE and LTE in MEME media (1 mg/mL) was added to some groups instead of normal media. These groups are designated with ES and TS (ECM extract suspension and tissue extract suspension). In total 21 groups were prepared in 96-well plates (n=3, 50 µL): P, P+ES, P+TS, HA, HA+EG, HA+EG+TS, HA+TG, HA+TS, HA+ES, HP, HP+EG, HP+EG+TS, HP+TG, HP+TS, HP+ES, COL, COL+EG, COL+EG+TS, COL+TG, COL+TS, and COL+ES. All groups and concentrations are listed in Table 3.

HEPG2 hepatocellular carcinoma cells were expanded in 2-D on tissue culture plastic using 150 mm diameter dishes until 75% confluence with Minimum Essential Media Eagle (MEME, HyClone, Logan, Utah) with 10% FBS (HyClone).

Cells were detached from the substrate with Trypsin (HyClone) and counted prior to centrifugation. For proliferation assays, 5,000 cells were seeded per well in the 96-well plates containing the previously prepared liver substrates. The plates were then transferred to an incubator (37° C., 5% $CO_2$) and proliferation was determined using with 3-(4,5-dimethylthiazol-2-yl)-5-(3-carboxymethoxyphenyl)-2-(4-sulfophenyl)-2H-tetrazolium (MTS) assays (Promega, Madison, Wis.) on day 3, day 5, and day 7 of culture. Aliquots (100 μL) were removed and absorbance readings determined at 490 nm using a Spectramax M5 Tunable Microplate Reader (Molecular Devices, Sunnyvale, Calif.). Absorbance levels are directly proportional to the number of live cells. Media was changed on day 4. Images of the cells were taken on day 3, day 5, and day 7 prior to MTS assays for subsequent morphological analysis. Cell viability was assessed with the LIVE/DEAD© Viability/Cytotoxity Kit for mammalian cells (Invitrogen). Concentrations of 4 mM calcein-AM and 4 mM ethidium homodimer-1 in DPBS were prepared for the assay. Media was aspirated and 100 ml of the assay solutions was added to each well. Constructs were incubated for 30 min (37° C., 5% $CO_2$), followed by one wash with DPBS, and then imaged and photographed with fluorescence under the microscope (Zeiss). LIVE and DEAD photos were overlaid. Phase microscopy photos were taken at the same time. All pictures taken were representative of the entire well.

Primary Human Hepatocyte Culture on Liver-Specific sECMs

Primary human hepatocytes were extracted from the liver of a Caucasian, 50 yr old male. Cells were suspended in 25 ml of William's E Medium solution and counted on the hemocytometer with Trypan blue to assess viability (85%). Substrate groups (50 μL in 96-well plates) were prepared as described above and $6 \times 10^4$ cells were seeded on top of each substrate and incubated for 3 hrs (37° C., 5% $CO_2$). Following incubation substrates were washed 3 times with warm DPBS to remove any dead or unattached cells. An additional layer of the corresponding gel solutions were added to each well and allowed to crosslink for 1 hr to create sandwich culture tissue constructs. After the gels were sufficiently cross-linked, 100 μl of fresh William's E Medium or conditioned TS or ES media was added to the appropriate wells. The hepatocytes were maintained in culture for 4 weeks, with media changes every 2 days.

Every week, the constructs were analyzed for differences and similarities of cellular morphology. Phase microscopy photos were taken with a Zeiss Axiovert (Carl Zeiss MicroImaging, LLC, Thornwood, N.Y.) at 10× and 20× magnification. Mitochondrial metabolism, often a measure of proliferation, was assessed by MTS at week 1, 2, 3, and 4, in the same manner as described elsewhere herein. On week 4, cell viability was assessed using by LIVE/DEAD© as described

TABLE 3

Combinations of all substrate groups implemented within the invention.

| Abbreviation | Primary Component | Modification | Concentration | Gel Supplement | Gel Supp. Concentration | Media Supplement | Media Supp. Concentration |
|---|---|---|---|---|---|---|---|
| P | TC Plastic | — | — | — | — | — | — |
| P + ES | TC Plastic | — | — | — | — | ECM Extract | 1 mg/mL |
| P + TS | TC Plastic | — | — | — | — | Tissue Extract | 1 mg/mL |
| Col | Collagen I | — | 0.5 mg/mL | — | — | — | — |
| Col + EG | Collagen I | — | 0.5 mg/mL | ECM Extract | 0.5 mg/mL | — | — |
| Col + EG + TS | Collagen I | — | 0.5 mg/mL | ECM Extract | 0.5 mg/mL | Tissue Extract | 1 mg/mL |
| Col + TG | Collagen I | — | 0.5 mg/mL | Tissue Extract | 0.5 mg/mL | — | — |
| Col + TS | Collagen I | — | 0.5 mg/mL | — | — | Tissue Extract | 1 mg/mL |
| Col + ES | Collagen I | — | 0.5 mg/mL | — | — | ECM Extract | 1 mg/mL |
| HA | Hyaluronic Acid | — | 4 mg/mL | — | — | — | — |
| HA + EG | Hyaluronic Acid | — | 4 mg/mL | ECM Extract | 0.5 mg/mL | — | — |
| HA + EG + TS | Hyaluronic Acid | — | 4 mg/mL | ECM Extract | 0.5 mg/mL | Tissue Extract | 1 mg/mL |
| HA + TG | Hyaluronic Acid | — | 4 mg/mL | Tissue Extract | 0.5 mg/mL | — | — |
| HA + TS | Hyaluronic Acid | — | 4 mg/mL | — | — | Tissue Extract | 1 mg/mL |
| HA + ES | Hyaluronic Acid | — | 4 mg/mL | — | — | ECM Extract | 1 mg/mL |
| HP | Hyaluronic Acid | Heparin-Conjugation | 4 mg/mL | — | — | — | — |
| HP + EG | Hyaluronic Acid | Heparin-Conjugation | 4 mg/mL | ECM Extract | 0.5 mg/mL | — | — |
| HP + EG + TS | Hyaluronic Acid | Heparin-Conjugation | 4 mg/mL | ECM Extract | 0.5 mg/mL | Tissue Extract | 1 mg/mL |
| HP + TG | Hyaluronic Acid | Heparin-Conjugation | 4 mg/mL | Tissue Extract | 0.5 mg/mL | — | — |
| HP + TS | Hyaluronic Acid | Heparin-Conjugation | 4 mg/mL | — | — | Tissue Extract | 1 mg/mL |
| HP + ES | Hyaluronic Acid | Heparin-Conjugation | 4 mg/mL | — | — | ECM Extract | 1 mg/mL |

Nomenclature: P = plastic; Col = collagen; HA = Extracel (hyaluronic acid); HP = Extracel-HP (heparin-conjugated hyaluronic acid); ES = liver ECM extract delivered by media suspension; TS = whole liver tissue extract delivered by media suspension; EG = liver ECM extract incorporated into the gel. TG = whole liver tissue extract incorporated into the gel.

above, except due to the sandwich culture, the incubation period was extended to 45 min.

Human Albumin ELISA and Immunohistochemistry

For functional characterization, cells were assessed for albumin secretion. Once each week, during normal media changes, spent media was extracted from triplicate wells of each group and transferred to microcentrifuge tubes. Samples were stored at −80° C. until the end of the experiment. Secreted levels of albumin were quantified using a Human Albumin ELISA Kit (Bethyl Laboratories, Montgomery, Tex.). Samples were quantified on the plate reader at 450 nm.

For immunohistochemistry, at the end of the experiment, samples were prefixed in 4% paraformaldehyde for 30 min. Following fixation all samples were washed three times in PBS and stored at 4° C. Prior to staining, all samples were permeabilized with 0.1% Triton X-100 (TX-100) in PBS. Cells were washed twice to remove any remaining TX-100. Treatments were incubated in 100 μl of Dako Antibody Protein Block, Serium-Free (Dako, Carpinteria, Calif.) for 30 minutes. Following blocking, the human albumin primary antibody (1:100, raised in mouse, Sigma) was prepared in Dako Antibody Diluent with background reduction (Dako) and added to each well and allowed to incubate at 4° C. overnight. Samples were washed three times for 15 minutes in PBS followed by application of the secondary Anti-mouse IgG FITC antibody (1:200, Sigma). Samples were incubated with the secondary for 3 hr. Cells were washed three more times with PBS and viewed at 20× magnification with the Zeiss Axiovert.

Urea Drug Analysis

Spent media was extracted from triplicate wells of each group and transferred to microcentrifuge tubes once each week. Samples were stored at −80° C. until the end of the experiment. Urea levels in 75 μl media aliquots were analyzed using the QuantiChrom™ Urea Colorimetric Assay Kit (BioAssay Systems, Hayward, Calif.). Samples were quantified on the plate reader at 430 nm.

Cytochrome p450-Dependent Drug Metabolism Assay

On week 4 of culture a kinetic assay was performed to assess cytochrome p450-dependent drug metabolism activity. Solutions of 50 mM 3-cyano-7-ethoxycoumarin (1000) in William's Media were added to triplicate groups after aspirating spent media. The well-plates were immediately transferred to the plate reader where fluorescent readings (408 nm excitation/450 nm emission) were taken every 40 sec for 15 minutes to measure the fluorescent metabolized drug product.

Analysis of Decellularized ECM Contents

Fresh and Decellularized Liver ECM were fixed in 10% formalin for 6 hrs. Samples were placed in tissue cassettes and processed overnight. Tissue was embedded in wax and cross sectioned to a thickness of 5 um. Sections were mounted on slides and placed on a heating plate for 3 hrs. Slides were stained with Hematoxylin and Eosin (H&E) (Sigma), Masson Trichome (Sigma), and 4,6 diamidino-2-phenylindole (DAPI) (Vector) for observation of nuclear content and protein sustainability. Photos were taken at 100×, 200× and 400× magnifications.

DNA Content

Decellularized and Fresh samples were dabbed with gauze and placed on weighing trays. Samples were flash frozen for 3 hrs at −80° C. Samples were placed on the lyopholizer for 48 hrs. Lyopholoized samples were grinded into powder using the 6470 Freezer Mill (Spex, Sample Prep). 25 mg of powder was pre-weighed for Fresh and Decellularized samples. Triplicates were done for each treatment. Using the Qiagen DNEASY Kit DNA was extracted and analyzed on the Nano Drop for DNA concentration. DNA yield was normalized to the initial weight of each sample. The remaining portions of the samples were stored at −80° C.

The results of the experiments are now described.

HEPG2 Culture—Proliferation, Viability, and Morphology

Figure 11:
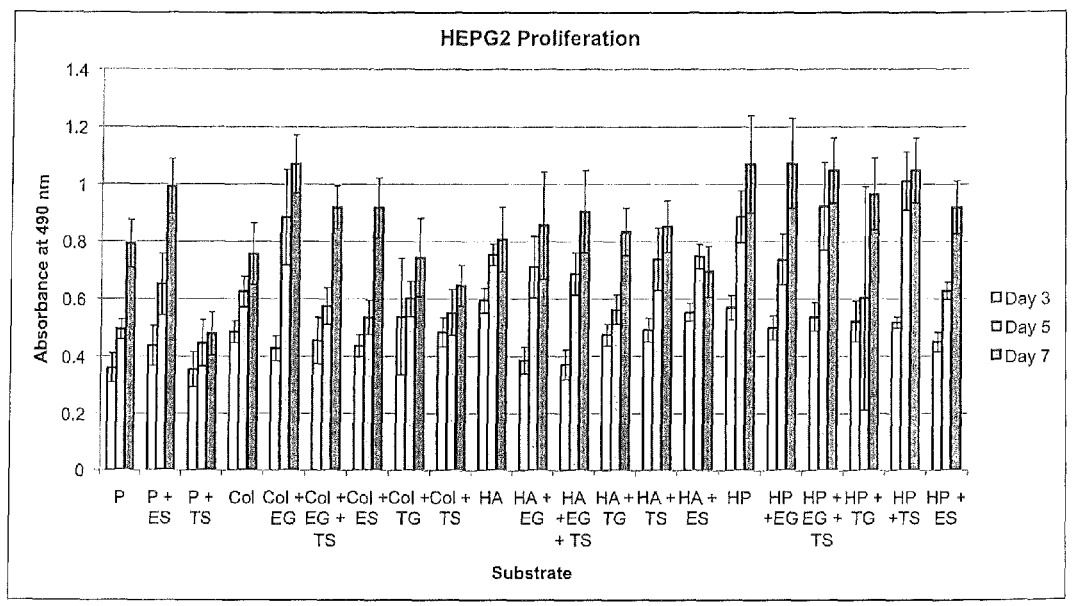
FIG. 11 is an image depicting proliferative data of HEPG2 cells cultured on plastic and collagen, HA, and HP-based sECMs. MTS assays were performed on days 3, 5, and 7.

HEPG2 cells showed proliferative trends on all substrates as depicted in FIG. 11. The differences between absorbance readings form the MTS assays on day 3 versus day 7 were significant (p<0.05) in all groups with the exception of P+TS and Col+TG, which were not significant. Cells proliferated the greatest on the following substrates: P+ES, Col+EG, and all HP groups. LIVE/DEAD stained images showed sufficient cell viability with all groups maintaining greater than 95% viable cells as depicted in FIG. 12. MTS and LIVE/DEAD data indicated sufficient biocompatibility of the liver-based sECMs to continue onto hepatocyte cultures.

It was also observed that the 21 groups fell into 4 main categories of differing morphology as depicted in FIG. 12. The groups P, P+ES, COL, COL+EG, COL+ES, HA, and HP displayed the monolayer cluster morphology commonly observed when HEPG2s are cultured on plastic. The groups P+TS, COL+TG, COL+EG+TS, COL+TS, and HA+TG clearly displayed a different spindle shaped morphology. The common factor in these groups was the addition of whole liver tissue-derived extract, either added in the media, or incorporated into the gel. This suggests that the distinct morphology was caused specifically by components in the whole liver tissue-derived extracts. The third category consisted of HA+EG, HP+EG, and HP+TG, in which the cells formed tight rounded aggregates. The last category seemed to have a combination of the traits observed in the second and third categories. In the HA+EG, HA+EG+TS, HA+TS, HP+EG+TS, HP+TS, and HP+ES groups, cells formed tight aggregates but then spread outwards from the aggregates over time. The morphological differences highlighted here suggest that the incorporation of LEE and LTE in culture do in fact induce observable differences in the cells.

Primary Hepatocyte Cell Culture

Figure 6:
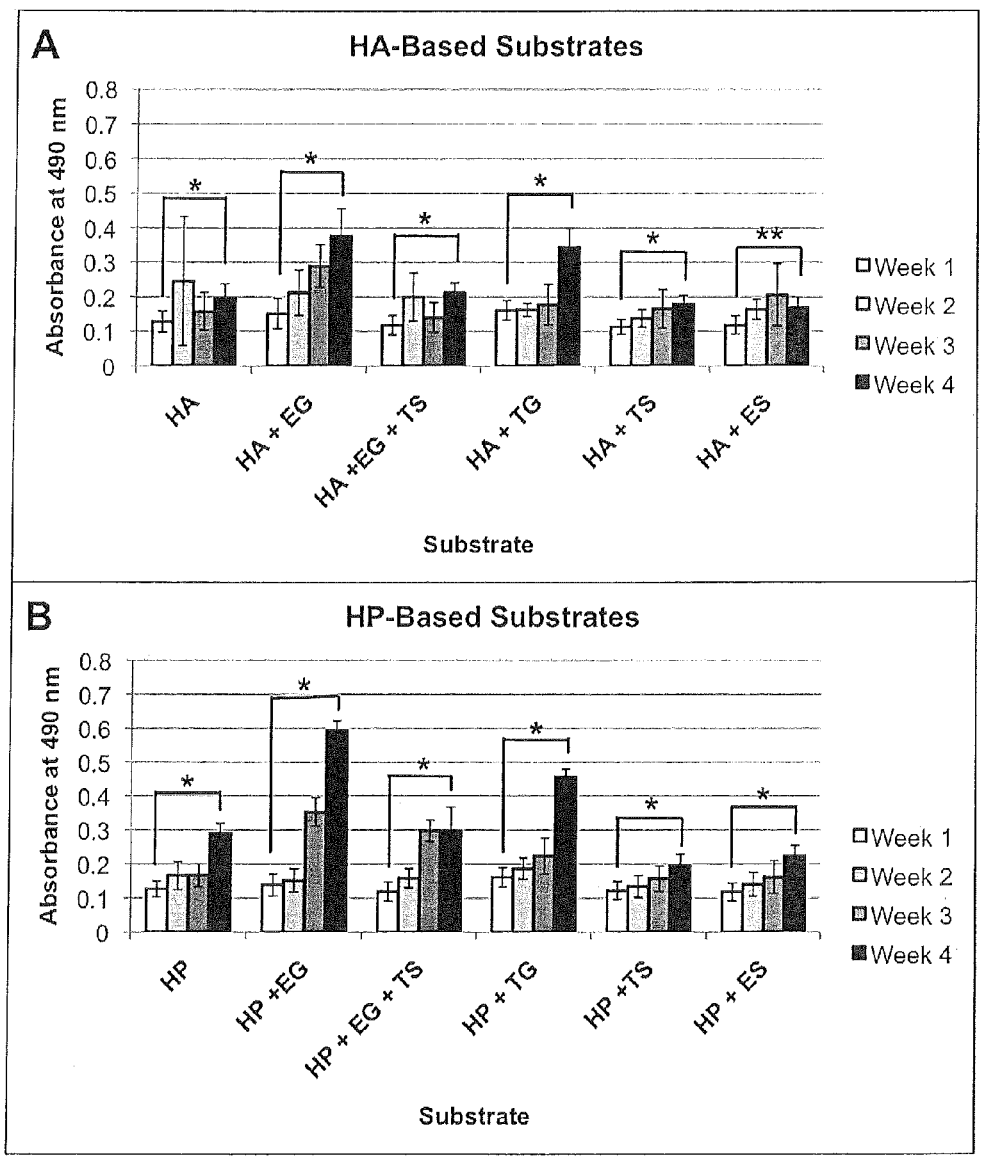
FIG. 6, comprising
Figure 13:
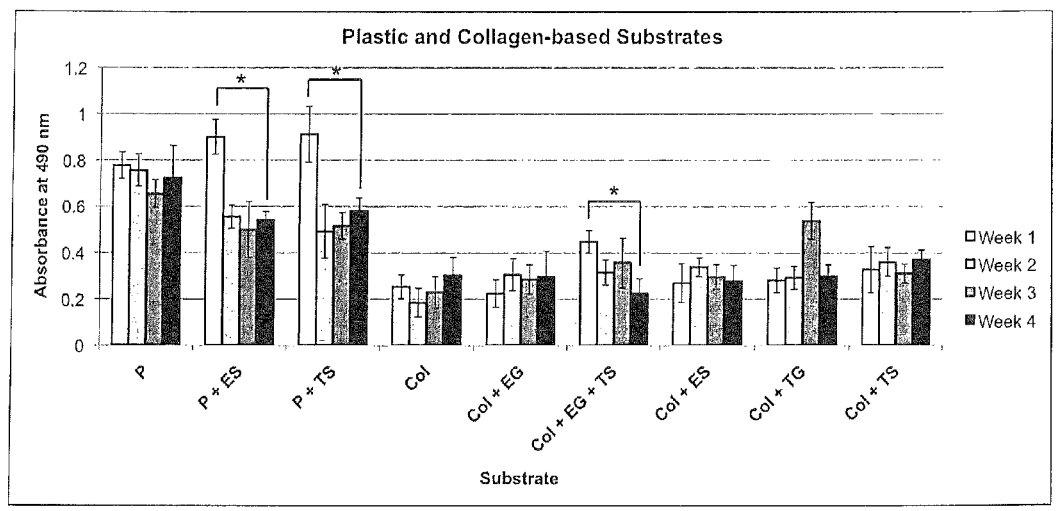
FIG. 13 is an image depicting mitochondrial metabolism of primary human hepatocytes cultured in plastic and collagen-based substrates.

MTS assays revealed that in general, the mitochondrial metabolism of each primary human hepatocyte construct prepared from HA and HP liver sECMs increased over the 4-week experiment as depicted in FIG. 6. Absorbance readings from week 1 vs week 4 for all groups were statistically significant at p<0.01, with the exception of HA+ES, which was still significant, but at p<0.05. The HP-EG constructs showed the greatest increase in absorbance levels from week 1 to week 2. Absorbance readings of plastic and collagen-based groups did not increase over the experiment. In fact, the absorbance levels of the P+ES, P+TS, and COL+EG+TS groups decreased significantly from week 1 to week 4 as depicted in FIG. 13 (p<0.01).

Figure 7:
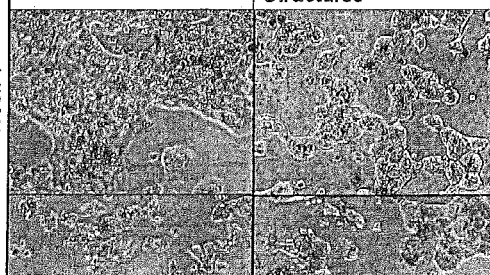
FIG. 7, comprising

Phase microscopy imaging showed remarkable differences in morphology between groups, allowing them to be organized into 4 categories as depicted in FIG. 7. Category 1 consisted of P, P+ES, and P+TS constructs; Category 2 consisted of COL, COL+EG, COL+EG+TS, COL+TG, COL+TS, COL+ES, HA+EG, and HA+EG+TS; Category 3 consisted of HA, HA+TG, HA+TS, HA+ES, HP, HP+TS, and HP+ES; and Category 4 consisted of HP+EG, HP+EG+TS, and HP+TG. In Category 1, hepatocytes initially formed monolayer-like clusters. However, over time the monolayers deteriorated and cell density decreased. This was mirrored for the most part in the MTS data discussed above. In Category 2, hepatocytes initially formed interconnecting structures, indicative of healthy hepatoctyes. However, like Category 1, by week 4, the interconnecting structures had severely deteriorated and cell density had decreased. In Category 3, there was no evidence of structural organization between cells at any time point. Finally, in Category 4, consisting of HP-EG, HP-EG+TS, and HP+TG, hepatocytes formed large interconnecting structures that remained healthy and stable throughout the experiment.

LIVE/DEAD staining on week 4 showed varying levels of cell viability between the construct categories as well. In general, Category 1 and Category 2 displayed the highest incidence of ethidium homodimer-1-stained dead cells, followed by Category 3, and lastly Category 4 with the most calcein-AM-stained viable cells and fewest dead cells as depicted in FIG. 7.

Figure 8:
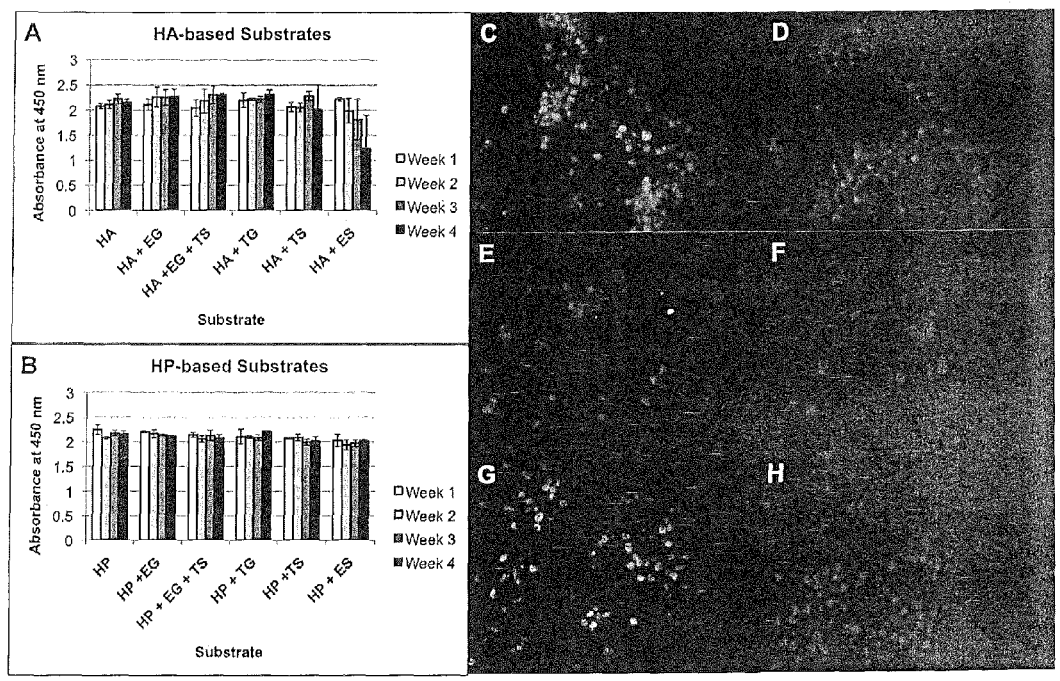
FIG. 8, comprising
Figure 14:
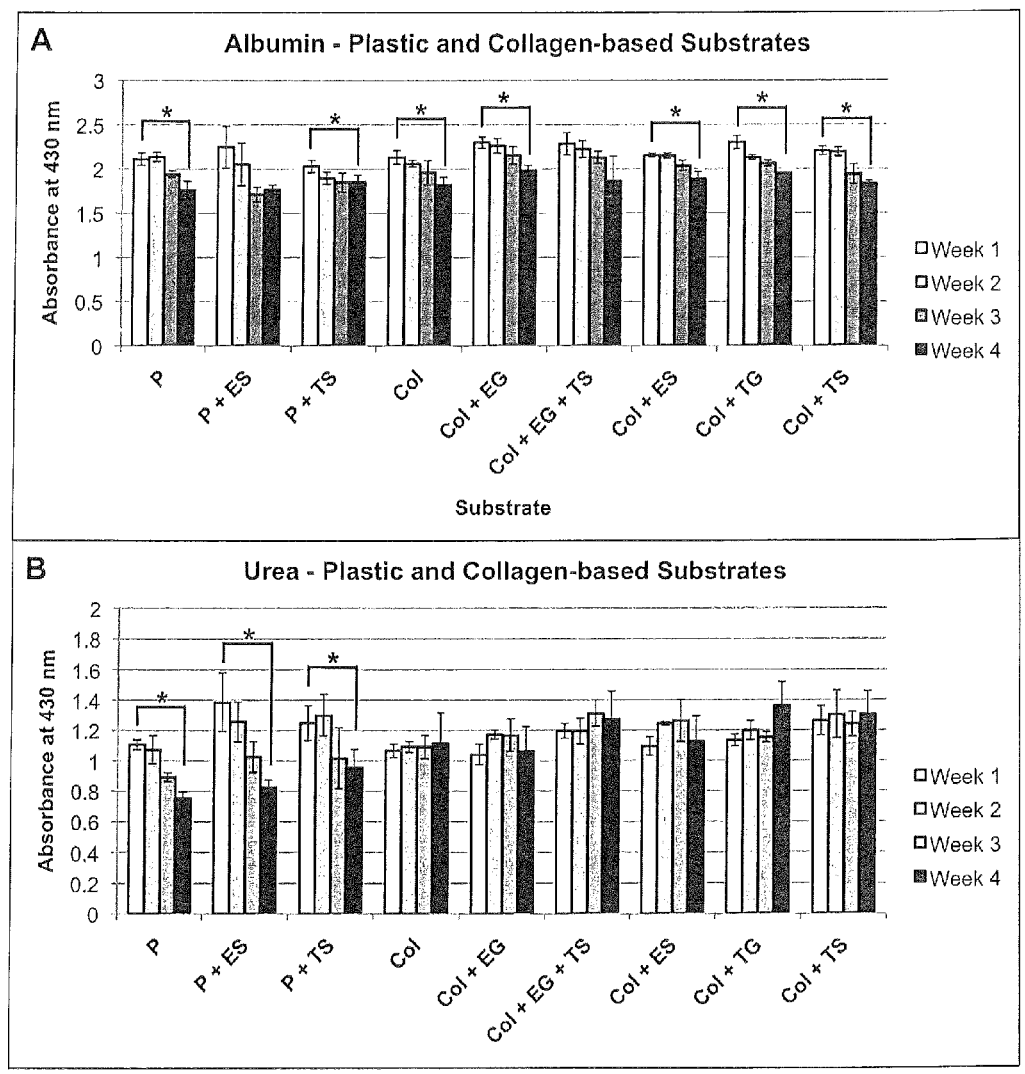
FIG. 14, comprising

Albumin ELISA showed albumin production was maintained in all HA and HP groups over the 4 week experiment, with the exception of one group, HA+ES, that showed a decreasing trend as depicted in FIG. 8A and FIG. 8B. In comparison, all plastic and collagen-based groups showed a week-to-week decreasing trend in albumin production for plastic and collagen groups as depicted in FIG. 14A. Albumin-depended absorbance levels in P, P+TS, COL, COL+EG, COL+ES, COL+TG, and COL+TS groups all decreased significantly between week 1 and week 4 ($p<0.05$).

Immunofluorescent staining of albumin showed different degrees of staining intensity depending on the base material and liver extract supplemented. HP+EG constructs by far showed the strongest albumin stains as depicted in FIG. 8C, followed by HP+EG+TS constructs as depicted in FIG. 8D. These groups also featured a higher incidence of cytoplasmic staining than other groups in which albumin staining remained near the cell nuclei as depicted in FIG. 8E through 8H. This observation suggests that the hepatocytes in HP+EG and HP+EG+TS constructs were more spread out, in stark contrast to the smaller rounded cells of other groups, and corresponds to the morphology observations discussed elsewhere herein.

Figure 9:
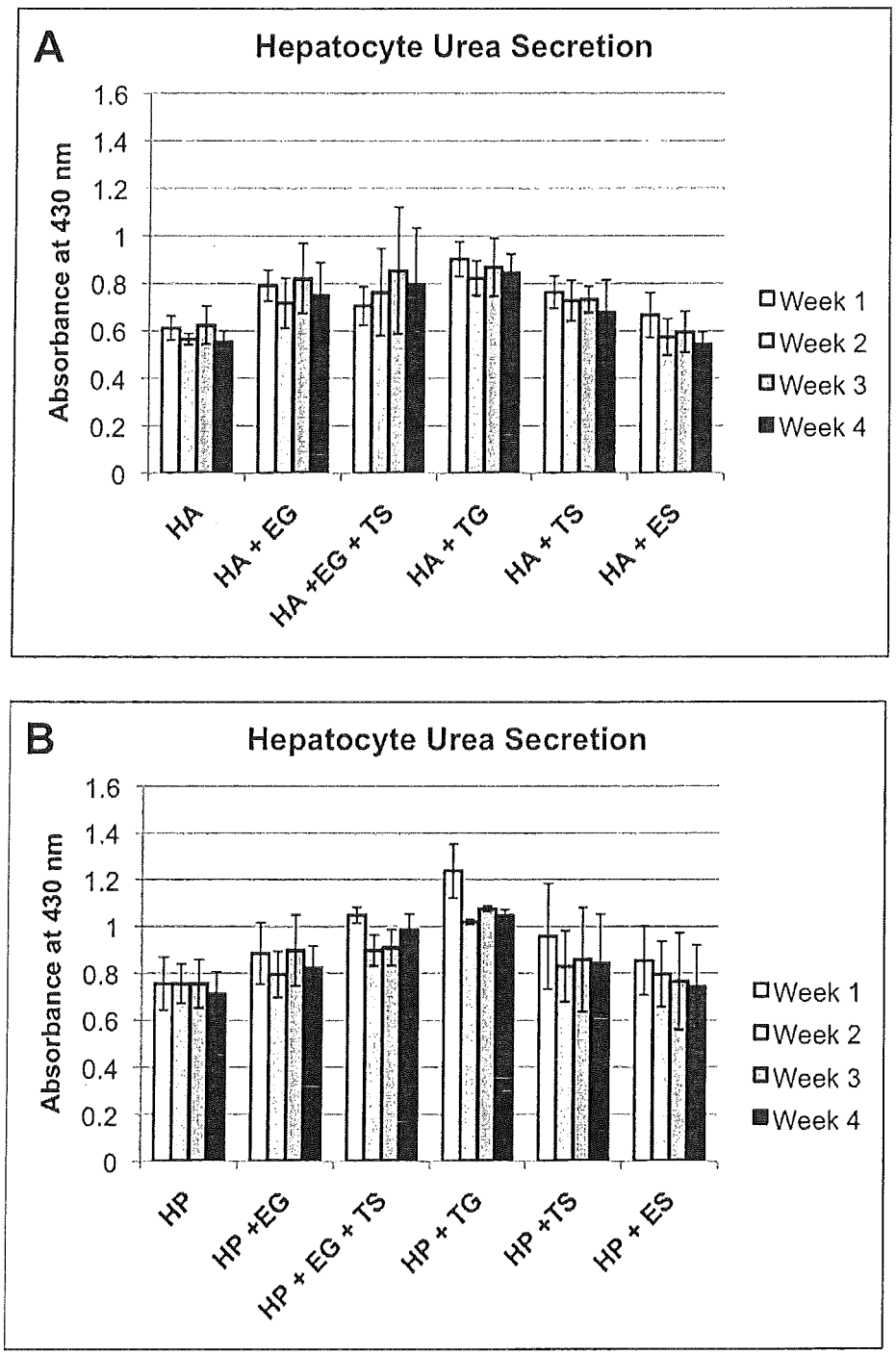
FIG. 9, comprising

Urea colorimetric assays revealed that in HA and HP constructs, levels of secreted remained consistent for the duration of the experiment. In no HA and HP groups did urea-dependent absorbance levels decrease significantly from week 1 to week 4 as depicted in FIG. 9. Similarly, collagen-based groups secreted consistent amounts of urea week to week. However, all 3 plastic groups secreted significantly less urea on week 4 than on week 1 as depicted in FIG. 14B. Also, in some instances, incorporation of LEE and LTE into HA and HP gels increased urea production.

Figure 10:
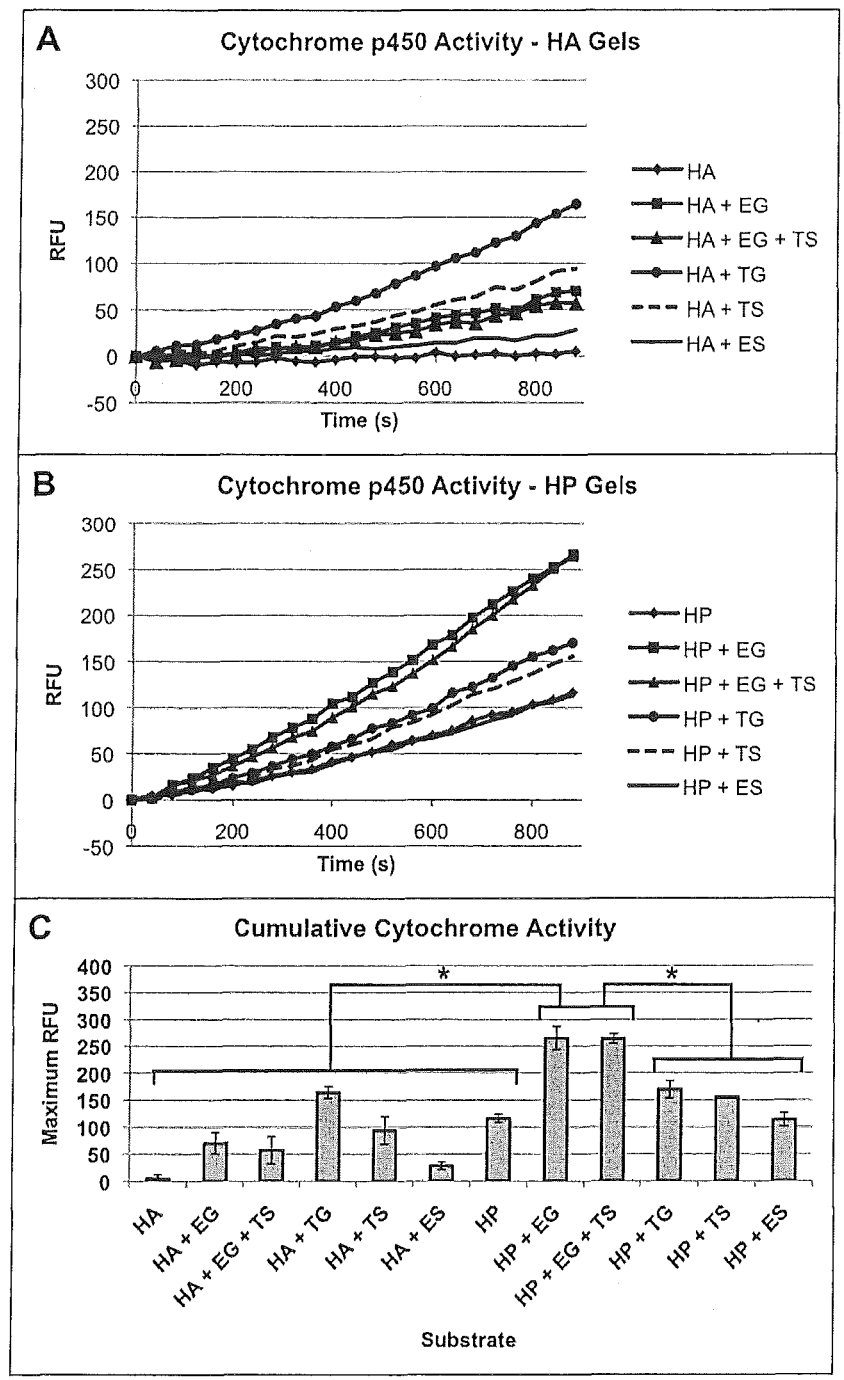
FIG. 10, comprising

Drug metabolism activity was investigated using a kinetic assay for Cytochrome p450-dependent metabolism. Media containing 3-cyano-7-ethoxycoumarin was added to the constructs, and the fluorescence of the metabolized drug product was measured on the plate read over a 15 min time course. Some plastic and collagen-based groups showed an increase in fluorescence during the kinetic assay, but in general performed poorly in comparison to HA and HP groups. Of the HA groups, HA+TG performed best as depicted in FIG. 10A. Other groups did not break 100 RFU. Maximum RFU output of HP was generally higher. In particular, RFU output of HP+EG and HP+EG+TS constructs were significantly higher than all other groups as depicted in FIG. 10B and FIG. 10C ($p<0.05$), indicating the best cytochrome p450-dependent drug metabolism.

Hyaluronic Acid-Based Systems

Despite performing all experiments with plastic, collagen, hyaluronic acid (with and without heparin)-based substrates, experiments were designed to focus on the hyaluronic acid-based systems. Extracel and Extracel-HP are pure systems that allowed for more sensitive screening of the liver-derived extracts. Without wishing to be bound by any particular theory, it is believed that collagen is one of the primary components of LEE and LTE. When the extracts are incorporated in collagen gels, the extract components may be largely overshadowed by the collagen in the gel. Furthermore, the high concentration of highly cell-adherent collagen in the collagen gels also may overshadow other ECM components from the added extracts, such as natural occurring HA and other GAGs, elastins, fibronectins, and laminins. Extracel and Extracel-HP provide structural integrity, some cell adherence, and in the case of Extracel-HP, regulation of GF release, while allowing the bioactive components of the extracts to play integral parts in influencing hepatocyte viability and function.

The differences in quantitative albumin and urea data between corresponding HA and HP groups was minimal, suggesting all the hepatocytes cultured in these matrices retained some basic level of function. This is in dramatic contrast to the albumin IHC and drug metabolism data. HP+EG, HP+EG+TS, and HP+TG stained significantly stronger for albumin. Additionally, these hepatocytes showed more fluorescence in the cytoplasm, indicating a more spread out morphology. Indeed, this was mirrored by phase microscopy, in which only HP+EG, HP+EG+TS, and HP+TG hepatocytes formed large interconnected structures that remained healthy and stable over 4 weeks. In the p450-dependent ethoxycoumarin drug metabolism assay, most groups showed some level of activity. However, HP+EG and HP+EG+TS constructs showed steeper RFU curves over the 15 minute kinetic assay. The cumulative cytochrome p450 activities of HP+EG and HP+EG+TS were significantly higher than those of all other groups indicating more efficient metabolism of the drug.

Without wishing to be bound by any particular theory, it is believed that two factors are likely responsible for the success of these 2 groups—first, heparin-regulated growth factor release, and second, the incorporation of the extract components directly into the matrices. In the present matrices, the conjugated heparin chains in the HP groups sequester and slowly release the various growth factors contained within the extracts. It is also believed that the localization of the extract components was important. Hepatocytes within matrices in which extracts were supplemented as components of the gels functioned better than those in matrices that were only supplemented with extracts suspended in the media. This is significant considering extracts were added to gels in a final concentration of 0.5 mg/mL in comparison to over 10 applications of 1.0 mg/mL concentrations of extracts in media. When added as part of the HP gels, growth factors were more readily sequestered by the heparin chains and already localized to the nearby hepatocytes. Furthermore, ECM components such as the collagens, GAGs, elastins, and others, become part of matrix and interact with the hepatocytes. In comparison, when added suspended in media, these ECM components are not readily available to the cells, as first they must diffuse through the upper layer of matrix, which is unlikely due to their molecular weights.

EG groups generally outperformed TG groups. ECM component quantification of the extracts showed increased collagen, GAG, and elastin content across the board in LEE compared to LTE. Without being held to any particular theory, it is believed that the increased levels of these components have substantial effect of hepatocyte function by providing a biomaterial environment closure to that of the liver. The differences in component concentrations could be a result of several factors.

These results presented herein demonstrate the successful development of a biomaterial system in which the viability and function of primary human hepatocytes could be supported for at least 4 weeks. A desirable construct can successfully metabolize ethoxycoumarin, a drug that targets the CYP1A2, CYP2C9, and CYP2C19 isoforms of cytochrome p450.

The constructs described herein are designed to transition to fully 3-D liver constructs by encapsulating cells in liver sECM hydrogels. This would allow for the preparation/cell seeding step to be more simple and efficient. A single encapsulation step is much quicker in comparison to sandwich culture setups, which require gel plating, crosslinking, cell seeding, waiting for attachment, washing, second gel plating, crosslinking, adding media.

The results presented herein demonstrate that a new hydrogel-based system that incorporates liver-derived extracts for maintenance of primary human hepatocyte viability and function in vitro has been developed and evaluated. Of all the hydrogel system variations investigated, a heparin-conjugated hyaluronic acid hydrogel containing ECM components and growth factors derived from a decellularized liver most desirably supported hepatocytes during the 4 week experiment. These hepatocyte-sECM constructs gave rise to interconnected hepatocyte structures that remained viable and stable throughout the experiment, while secreting albumin and urea at consistent levels. IHC showed strong presence of cytoplasmic albumin, further illustrating active albumin production. Lastly, these constructs were able to successfully metabolize the drug ethoxycoumarin at levels greater than all other groups tested, verifying activity of several cytochrome p450 isoforms. With an increasing need for functional human tissues to streamline the pharmaceutical pipeline, the liver-sECM constructs can give scientists the tools to perform drug and toxicology screening with increased efficiency. These experiments demonstrate that the combination of HA-based biomaterials conjugated with heparin containing liver-derived extracts provide a system useful for liver tissue engineering and drug discovery research.

Example 7: Three-Dimensional Culture of Hepatocytes on Porcine Liver Tissue-Derived Extracellular Matrix There is currently no optimal system to expand and maintain the function of human adult hepatocytes in culture. The experiments described herein investigate whether three-dimensional (3D) ECM derived from porcine liver can facilitate the growth and maintenance of physiological functions of liver cells. The results presented herein demonstrate that optimized decellularization/oxidation procedures removed up to 93% of the cellular components from porcine liver tissue and preserved key molecular components in the ECM, including collagen-I, -III, and -IV, proteoglycans, glycosaminoglycans, fibronectin, elastin, and laminin. When HepG2 cells or human hepatocytes were seeded onto ECM discs, uniform multi-layer constructs of both cell types were formed. Dynamic culture conditions yielded better cellular infiltration into the ECM discs. Human hepatocytes cultured on ECM discs expressed significantly higher levels of albumin over a 21-day culture period compared to cells cultured in traditional polystyrene cultureware or in a collagen gel "sandwich". The culture of hepatocytes on 3D liver-specific ECM resulted in considerably improved cell growth and maintained cell function; therefore, this system can be used in liver tissue regeneration, drug discovery or toxicology studies.

To further develop a culture platform for liver cell expansion, different methods to fabricate liver ECM discs and culturing conditions were tested to determine how their impact on the long-term expansion and maintenance of human hepatocytes. Further, it was investigated how the decellularization method influenced the composition of the liver ECM and affected cell expansion and function.

The materials and methods employed in these experiments are now described.

Materials and Methods

Hepatocytes and Liver Tissue

HepG2 cells (ATCC, Manassas, Va.) and human primary hepatocytes (Invitrogen, Carlsbad, Calif.) were used for this study. HepG2 cells, a human liver carcinoma cell line, were mainly used to optimize the decellularized liver ECM discs and confirm cell viability and cell-matrix interaction when the cells were cultured on the discs treated with six methods. Human primary hepatocytes were employed to test albumin secretion function. To obtain ECM from liver tissue, 15 fresh porcine livers were harvested from adult swine. Fresh porcine liver was dissected into individual lobes and frozen at −20° C. until use. Thawed liver lobes were cut into 3 mm thick slices using a deli-style slicer (Model 667, Chef's Choice, Avondale, Pa.). To generate the liver ECM discs for hepatocyte culture, the sliced liver tissues were cut into different sized discs (diameter from 1 to 1.5 cm) designed to fit into the wells of either 12 or 24 well multi-plates. The liver discs were frozen at −20° C. until use.

Liver Decellularization Methods

Several detergents and decellularization methods were selected to fabricate liver tissue ECM, i.e. decellularization with distilled water or phosphate-buffered saline (PBS) wash plus detergents (Zhang et al., 2009, Biomaterials, 30:4021-8; Liu et al., 2009, Biomaterials, 30:3865-73; Whitlock et al., 2007, Biomaterials, 28:4321-9; Wu et al., 2011, Biomaterials, 32:1317-26; Ott et al., 2008, Nat Med, 14:213-21), salt solution plus detergent to preserve GAGs (Rojkind et al., 1980, J Cell Biol, 87:255-63), and 5% peracetic acid (PAA) to increase the porosity of ECM (Liu et al., 2009, Biomaterials, 30:3865-73; Whitlock et al., 2007, Biomaterials, 28:4321-9; Wu et al., 2011, Biomaterials, 32:1317-26). To optimize the approach, six methods were tested to decellularize liver tissue in this study (see Table 4). Briefly, the liver disc samples were thawed and placed in a 500 ml bottle and decellularization solution was added. The ratio (w/v) of liver ECM to solution was 1:10, i.e. 10 g of liver tissue samples per 100 ml solution. The bottles for washing the liver ECM discs were placed on an orbital shaker (Barnstead MaxQ400, Dubuque, Iowa) at 200 rpm at 4° C. Some ECM discs were treated with 5% PAA for an extra 3 h and washed with distilled water or PBS. The solution in the bottles was changed 3 times per day for 3 days. The gross morphology of the decellularized liver samples was photographed, and then the size, thickness and shape of the samples were measured. The liver ECM discs were placed into 24-well plates for lyophilization as previously described (Zhang et al., 2009, Biomaterials, 30:4021-8) followed by sterilization with gamma irradiation (1000 rad) for 1-2 h. For convenience, the six decellularization methods are abbreviated as water-, PBS-, salt-wash, water+PAA, PBS+PAA, and salt+PAA wash (i.e. 5% PAA treatment for 3 h after each of first 3 wash methods).

TABLE 4

Different methods of decellularization of liver ECM:

| Method # | Method | Decellularization Process |
|---|---|---|
| 1 | Water wash | Distilled water for 3 days, 2% Triton X-100 and 0.1% ammonium hydroxide in distilled water for 5 days, distilled water for 3 days at 4 C. °. |
| 2 | Water wash + PAA | Same as Method-1 but with 5% PAA treatment for 3 h after decellularization. |
| 3 | PBS wash | PBS for 3 days, 2% Triton X-100 for 5 days, PBS for 3 days, |
| 4 | PBS wash + PAA | Same as Method-3 but with 5% PAA treatment for 3 h after decellularization |
| 5 | Salt wash | 3.4M NaCl for 30 min, PBS for 3 days, 2% Triton X-100 for 5 days, PBS wash for 3 days |
| 6 | Salt wash + PAA | Same as Method-5 but with 5% PAA treatment for 3 h after decellularization |

Decellularization Assessment

The decellularized liver ECM discs were fixed in 10% neutral buffered formalin, embedded in paraffin and processed for histology. The ECM samples were cut into 5 μm sections and stained with hematoxylin and eosin (H&E) and Masson's trichrome. Sections were mounted in mounting media containing 4,6-diamidino-2-phenylindole (DAPI) (Vector, Burlingame, Calif.) to confirm the extent of decellularization. To measure DNA content, a total of 2 decellularized ECM discs and a sample of the fresh-frozen liver tissue samples as a control were used. DNA content was measured as previously described (Zhang et al., 2009, Biomaterials, 30:4021-8; Liu et al., 2009, Biomaterials, 30:3865-73). Briefly, total DNA was isolated from 25 mg of tissue (dry weight) using a commercially available kit (DNeasy, Qiagen, Valencia, Calif.). The DNA concentration was estimated at 260 nm using a NanoDrop spectrophotometer (Thermo Scientific, Waltham, Mass.) and normalized to the initial dry weight of the samples.

Scanning Electron Microscopy (SEM)

Following decellularization, samples were fixed in 2.5% glutaraldehyde for at least 2 h at room temperature. Following fixation, samples were briefly rinsed in deionized water, dehydrated via a graded ethanol series, and dried in a critical point dryer (EMS 850, Electron Microscopy Sciences, Hatfield, Pa.). Samples were then sputter coated with gold (Hummer 6.2, Anatech Ltd, Union City, Calif.) prior to SEM imaging. Electron micrographs of liver cross-sections were obtained at 25.0 kV, 50 Pa, 50× magnifications using a Hitachi S-2600 SEM (Hitachi Technologies America, Pleasanton, Calif.).

Evaluation of ECM Components

Sections of ECM were stained with Alcian Blue and Sirius Red to visualize total collagen and PGs, respectively. To identify the total amount of collagen in the decellularized matrices, a Sircol™ kit (Biocolor Life Science Assays, UK) was used according to the manufacturer's instructions. To determine whether collagen-I, -III, -IV, laminin, fibronectin and elastin were retained in the decellularized matrices, the liver ECM samples were sectioned and stained using immunohistochemistry. Briefly, paraffin sections were rehydrated, incubated in antigen retrieval solution, and stained using antibodies to collagen-I, -III and -IV (Southern Biotech, Birmingham, Ala., 1:100 dilution), fibronectin (Santa Cruz Biotechnology, Santa Cruz, Calif., 1:100), laminin (Sigma Life Sciences, St Loius, Mo., 1:75) and elastin (Santa Cruz Biotechnology, 1:100). These sections were also counter-stained using hematoxylin. Images of the stained slides were captured using an upright microscope (Leica, Germany). To measure total GAGs among different treated liver ECM discs, 22 mg tissue pieces were obtained from ECM samples of each treatment (3 ECM samples/treatment). The Blyscan GAG assay (Biocolor Life Sciences Assays, UK) was used to quantify the amount of GAGs present according to the manufacturer's instructions.

Cell Seeding

To install liver ECM discs into multi plates, the discs were pushed to the bottom of each well using a segment of silicone tubing. The tubing height was 1.5 cm, inside diameter (ID) 0.9 cm and outer diameter (OD) 1.5 cm for 12 well plates or 0.5 ID×0.75 OD for 24 well plates (Nalgene Labware, Rochester, N.Y.). Prior to cell seeding, the discs were incubated in culture medium at 37° C. overnight. To select the best 3D liver ECM discs, HepG2 cells were seeded on the liver discs treated with each of six decellularization methods. Subsequently, human hepatocytes were cultured on the optimized 3D liver discs.

After the medium was aspirated, a cell suspension (50 μl) of HepG2 cells ($5 \times 10^5$ cells/cm$^2$) was pipetted onto the center of the disc. The cells were allowed to settle and attach to the disc scaffold for 3 h. Next, 2 ml of DMEM with 10% serum was added slowly. The HepG2 cell-seeded ECM discs were maintained under static and then dynamic culture conditions for 24 h on an orbital shaker (Belly Dancer, Stovall, Greensboro, N.C.) at 10 revolutions per minute and media was changed every other day. HepG2 cells at the same cell concentration as above were cultured in polystyrene dishes and collagen-I gel coating (BD Biosciences, Franklin Lakes, N.J.) as controls. For human primary hepatocyte ($1 \times 10^5$/cm$^2$) cultures, the same processes as above were followed and then hepatocytes were cultured in serum free Williams E medium.

Cell Proliferation Assay

To select the best liver ECM discs for hepatocyte growth, cell proliferation of HepG2 cells was measured using Alamar Blue according to the manufacturer's instructions (Invitrogen), for up to 12 days. At each time point, the seeded scaffolds were transferred into new wells prior to addition of the Alamar Blue reagent to ensure that the signal being measured was from cells on the scaffold and not cells that had attached to the surface or sides of the culture wells. A fluorescent plate reader (Molecular Devices Inc, Sunnyvale, Calif.) was used to measure fluorescence at 590 nm following excitation at 544 nm. Repeated measures (n=5) were used for each time point.

The optimized liver ECM discs tested above were used for primary human hepatocyte cultures. Cell viability and proliferation was measured for 21 days using an MTS (3-(4,5-dimethylthiazol-2-yl)-5-(3-carboxymethoxyphenyl)-2-(4-sulfophenyl)-2H-tetrazolium) assay. Hepatocytes were grown using 3 culture conditions: polystyrene dishes, collagen-I gel sandwich cultures, and the optimized liver ECM discs. Briefly, the MTS reagent was incubated with the cells in the dark for 1 h at 37° C. Following the incubation, 100 μl of the supernatant was transferred to a 96 well microplate and the absorbance was measured at 490 nm using a spectrophotometer (Molecular Devices, Sunnyvale, Calif.). Each sample was measured in triplicate.

Live/Dead Assays

To assess cell viability on day 21 of culture, human hepatocytes grown using 2D polystyrene plates, collagen gel sandwich cultures and the optimized liver ECM discs were subjected to live-dead staining using a commercial kit (L3224, Invitrogen) according to the manufacturer's instructions. Briefly, Calcein-AM and ethidium bromide homodimer were mixed in Hanks Balanced Salt Solution (HBSS) to a final concentration of 2 and 404, respectively. The mixture was then added to the cell cultures. Cultures were incubated for 15 min in the dark at room temperature, and the stained cells were washed and fixed in 4% glutaraldehyde before viewing under a fluorescent microscope. Primary hepatocytes appeared green (esterase activity on Calcein-AM) and dead cells appeared red (ethidium bromide) due to loss of membrane integrity. Multiple fields were photographed and 5 images were used for counting live (green) and dead cells (red).

Albumin Analysis

To test specific function of liver cells, the amount of albumin secreted into the culture medium was assessed. The culture media was collected from human hepatocytes grown on the optimized liver ECM discs for up to 21 days. The media was centrifuged at 500 g to remove cells and debris and the supernatant was frozen at $-80°$ C. until needed. Albumin was detected using an ELISA kit (Bethel Laboratories Inc., Montgomery, Tex.). To normalize albumin levels in the culture medium, the amount of albumin measured in one ml of medium was adjusted to the number of plated cells, i.e. ng/ml/1000 cells. Additionally, albumin expression in hepatocytes grown on the optimized liver ECM discs was assessed with immunocytochemistry.

Histological and Immunocytochemical Analysis

Liver ECM discs seeded with either HepG2 cells or primary human hepatocytes were fixed and sectioned for H&E, trichrome or DAPI staining. For immunocytochemistry, cells seeded in collagen gel sandwich cultures and on liver ECM discs were fixed with 4% paraformaldehyde for 20 min, washed with PBS three times, and incubated for an hour at room temperature with an antibody to albumin (Sigma, St Louis, Mo.) diluted 1:100 in PBS containing 0.5% Triton-X-100 and 5% goat serum. Cells were washed and incubated with a fluorescent-labeled secondary antibody (FITC-anti-mouse IgG2b, Southern Biotech, Birmingham, Ala.) for an additional hour. Cells were washed, sealed with DAPI-containing mounting medium (Vector Laboratories, Burlingame, Calif.), and analyzed using a fluorescent microscope (Leica, Germany).

Statistical Analysis

For the diameter, size area shrinkage (%) and thickness of 3D liver ECM discs, DNA content, cell proliferation assays, total collagen content, GAGs, and albumin measurement, means and standard error of the mean (SEM) (n=6 for DNA content, n=5 for cell proliferation experiments and n=4 for collagen detection) were calculated for each assay. Groups were compared using a two-tailed, Student's t-test with unequal variances. Differences were considered statistically significant at $p<0.05$.

The results of the experiments are now described.

Decellularized Liver ECM

Figure 15:
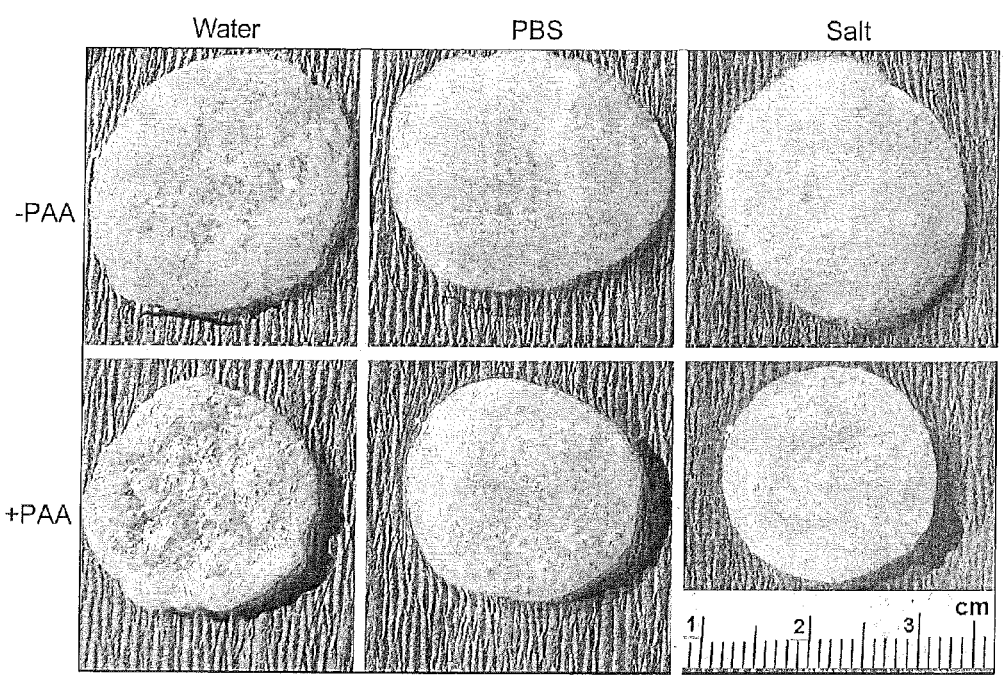
FIG. 15 depicts the gross appearance of liver ECM discs following decellularization. Liver ECM discs were subjected to decellularization using water, PBS or salt washes prior to treatment with PAA (top row) or after PAA (bottom row).
Figure 16:
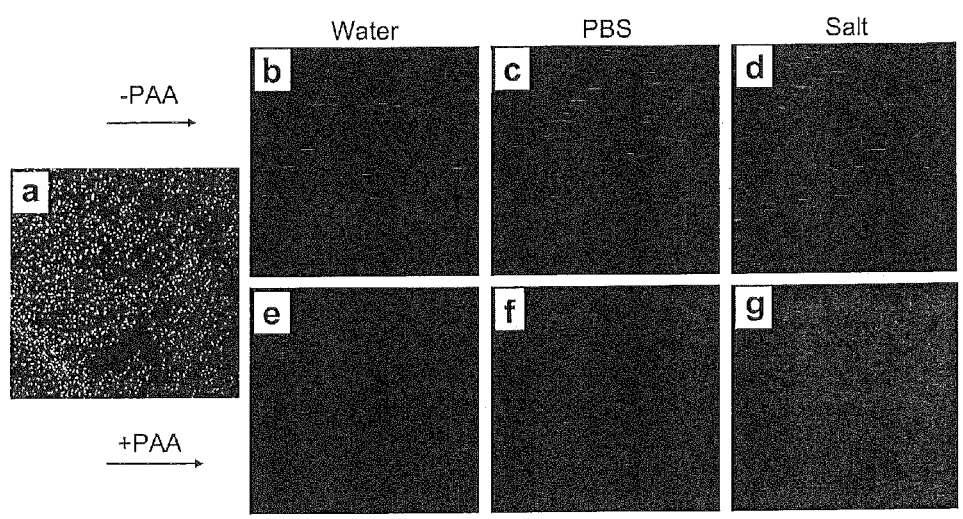
FIG. 16, comprising FIG. 16A through FIG. 16G, demonstrates that liver decellularization resulted in complete removal of nuclei. Liver tissue and scaffolds were sectioned and stained with the nuclear stain DAPI (blue), before decellularization (FIG. 16A) and following each of the six decellularization methods.

To optimize the decellularized liver ECM discs for liver cell culture, six wash methods (Table 4) were used. Grossly, the ECM discs maintained their original round shape throughout all wash protocols after decellularization. Although creating a rougher surface and greater porosity on the discs, all PAA treatments caused the discs to shrink significantly compared to their original size ($p<0.05$) (Table 5). The water-wash decellularization method generated less shrinkage and created more transparent ECM discs (see FIG. 15 and Table 5). DAPI staining of fresh-frozen liver tissue revealed punctate staining of cell nuclei within the tissue, clearly visible in all sections of fresh-frozen liver tissue. In contrast, no visible cell nuclei could be seen (FIG. 16B through 16G) in any decellularized sections, indicating that all six methods led to complete decellularization of the tissue.

Figure 17:
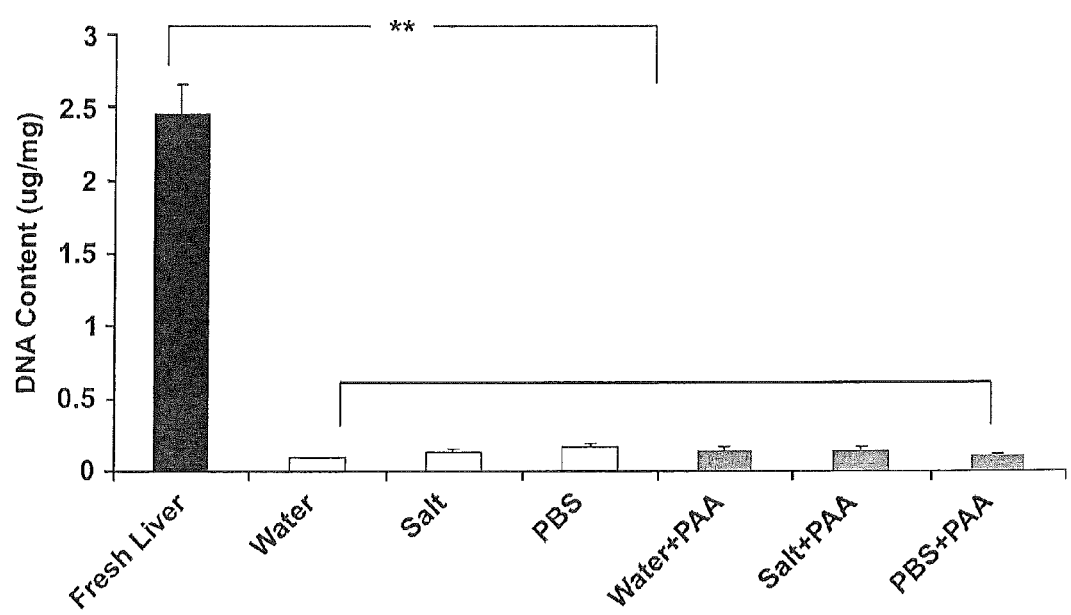
FIG. 17 shows DNA clearance in decellularized liver ECM. DNA content in fresh liver and after the six methods of decellularization was normalized to initial dry weight of the sample. **=p<0.01.
Figure 18:
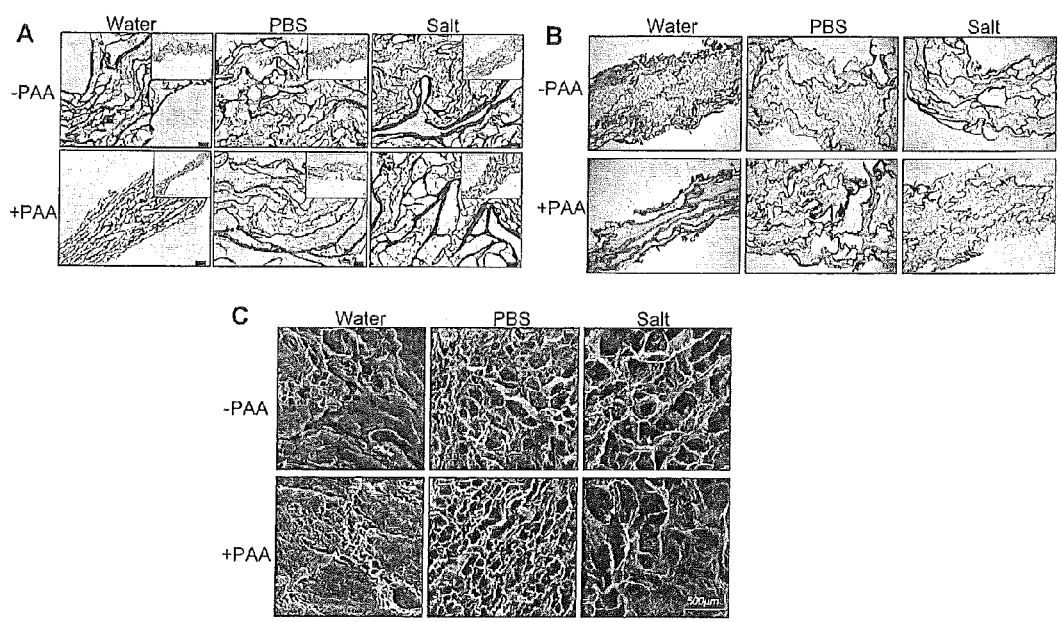
FIG. 18, comprising

To confirm this observation, the DNA content of the decellularized tissue ECM discs was quantified. While the DNA content in fresh-frozen liver tissue was 2.46±0.20 µg/mg, the DNA content in the decellularized ECM ranged from 0.09 to 0.16 µg/mg tissue, which represents 93-96% removal of DNA [n=6, $p<0.01$ (FIG. 17)]. Hematoxylin and eosin staining also revealed the absence of cell nuclei and other cellular components along with increases in intra-fascicular and inter-fascicular space (FIG. 18A). Decreased ECM thickness and increased porosity was noted in some cases when the water wash method was used (FIGS. 18A and 18B 19B).

TABLE 5

Assessment of liver ECM disc characteristics following decellularization:

| Wash | Water | Water | PBS | PBS | Salt | Salt |
|---|---|---|---|---|---|---|
| PAA | — | + | — | + | — | + |
| Diameter (mm) | 26.8 +/− 1.7 | 23.8 +/− 1.2 | 26.8 +/− 1.8 | 21.4 +/− 1.2 | 23.2 +/− 1.3 | 18.4 +/− 0.9 |
| Size Area Shrinkage (%) | 0 | 11.4 +/− 1.7 | 0 | 20.3 +/− 1.5 | 13.3 +/− 3.1 | 31.4 +/− 1.0 |
| Thickness (mm) | 0.8 +/− 0.10 | 0.6 +/− 0.08 | 0.9 +/− 0.12 | 1.2 +/− 0.18 | 1.1 +/− 0.15 | 1.1 +/− 0.16 |
| Shape (roundness) | + | ++ | + | +++ | ++ | +++ |
| Surface (roughness) | + | ++ | ++ | +++ | ++ | +++ |
| Color/Clarity | + | ++ | + | +++ | ++ | +++ |

Note:
Liver ECM discs were assessed for maintenance of round shape, uniform thickness, even surface, maintenance of size (area shrinkage) and appearance (color/clarity) by an experienced individual.
The gross morphology changes in liver ECM discs after decellularization were graded as follows: (+) mild change; (++) moderate change; (+++) severe change.

Scanning Electron Microscopy (SEM)

Remarkable differences in the pore size and the organization of the ultrastructure were observed via SEM in all decellularized liver ECM discs, no matter what method was used (FIG. 18C). Scaffolds decellularized via the PBS and salt wash methods appeared more porous than those decellularized using the water wash method. Additionally, the inclusion of PAA increased the apparent porosity of the ECM decellularized with water and PBS, but PAA had little impact on the salt decellularized scaffolds (FIG. 18C, top vs. bottom rows).

Complex Molecular Composition Within Liver ECM Discs

Figure 19:
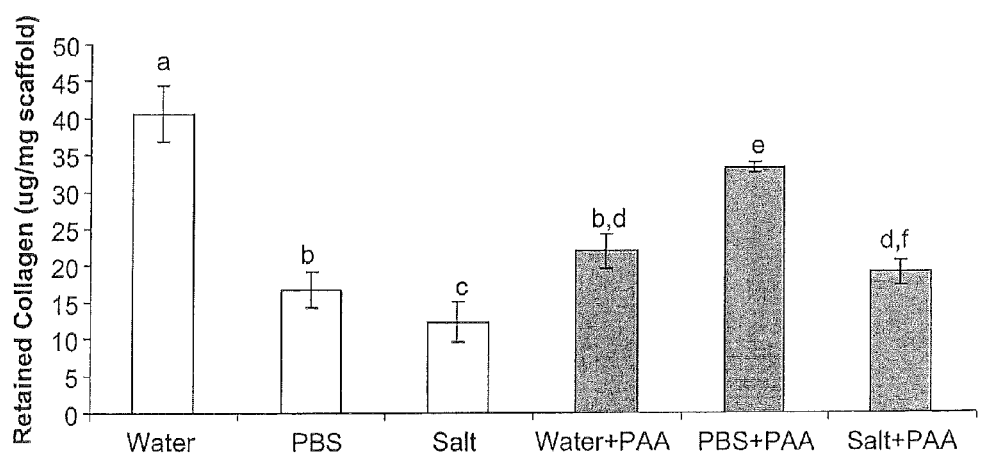
FIG. 19 depicts collagen content in decellularized liver discs. Total collagen analysis was performed using a colorimetric assay. Data are normalized to dry weight of samples and represent mean±S.D. for a minimum of n=4 per group. Different lowercase letters indicate significant differences at p<0.05, p<0.005 or p<0.0005 (comparison values for: b-c, c-d, a-e and b-f were p<0.05; d-e, c-f, a-b, a-c, b-e and a-f were p<0.005; a-d, c-e and e-f were p<0.0005).
Figure 20:
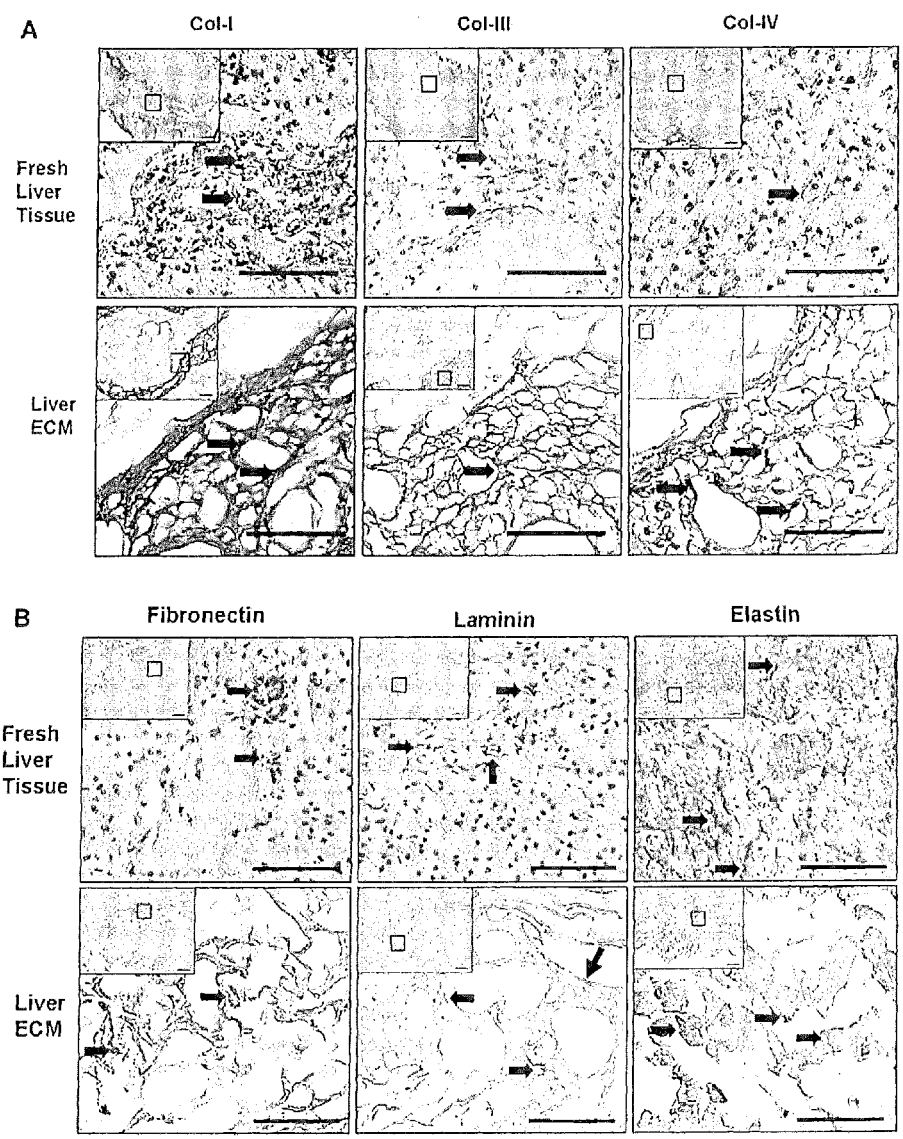
FIG. 20, comprising
Figure 21:
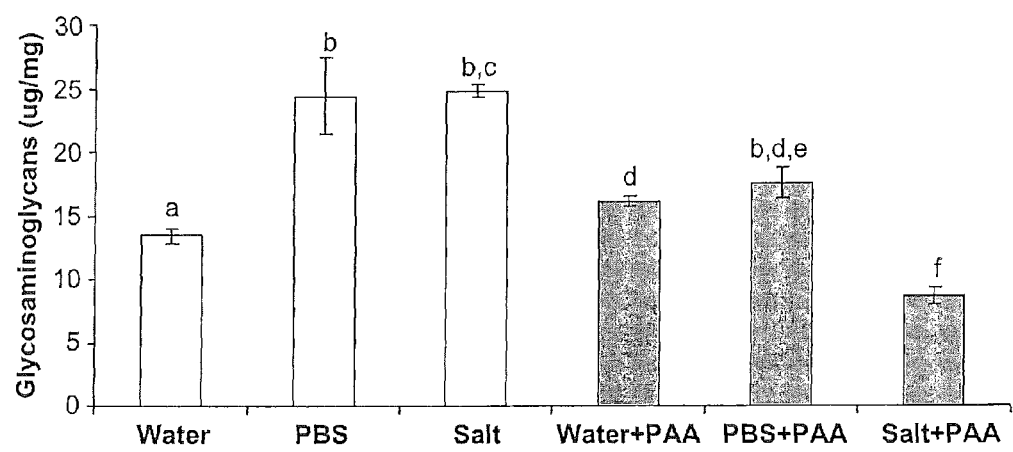
FIG. 21 is an image showing the estimation of total glycosaminoglycan content in decellularized liver discs. Data are normalized to dry weight of samples and represent mean±S.D. for a minimum of n=4 per group. Different lowercase letters indicate statistically significant groups (p<0.05).

Although total collagen was present after all 6 methods of decellularization, Sirius red staining and collagen quantification assays indicated that the water wash method maintained the most collagen in the ECM discs (FIGS. 18B and 19). Collagen-I, -III and -IV content were also better preserved using the water wash method (FIG. 20A). Collagen in these discs was mainly observed around vascular structures and parenchymal areas of the fresh liver and acellular liver ECM. The original amounts of fibronectin, laminin, and elastin were also retained on the decellularized discs, as shown on immunohistochemical analyses. Laminin and elastin expression was intense in vessels and biliary ducts, and fibronectin expression was most prominent in the parenchymal space and some biliary ducts (FIG. 20B), similar to other reports (Baptista et al., 2011, Hepatology, 53:604-17). Proteoglycans were retained among these ECM treated with six methods in Alcian Blue staining (FIG. 18B). Although it is difficult to identify differences in the amount of GAGs in immunostained images, the colorimetric GAG quantification assay showed that both salt and PBS wash methods preserved the most GAGs within liver ECM compared to the other decellularization methods (FIG. 21). Fewer GAGs were retained in the ECM after PAA treatment, similar to a previous report (Rojkind et al., 1980, J Cell Biol, 87:255-63).

Cell Viability and Proliferation on the Liver ECM Discs

Figure 22:
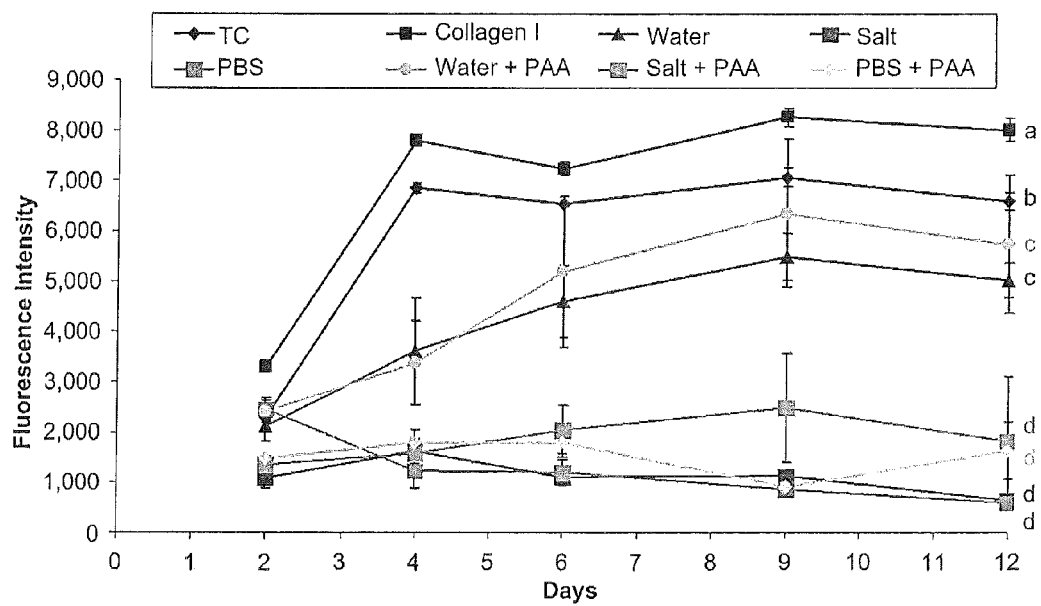
FIG. 22 is an image demonstrating that decellularization method affects the Hep2 cell proliferation seeded onto acellular scaffolds. The proliferation of HepG2 cells seeded onto polystyrene tissue culture wells (TC), collagen I-coated tissue culture wells, and acellular scaffolds prepared using each of the six decellularization methods was monitored over 12 days using the Alamar Blue assay. Different lower-case letters indicate statistically independent groups for days 4-12 ($p<0.05$).
Figure 23:
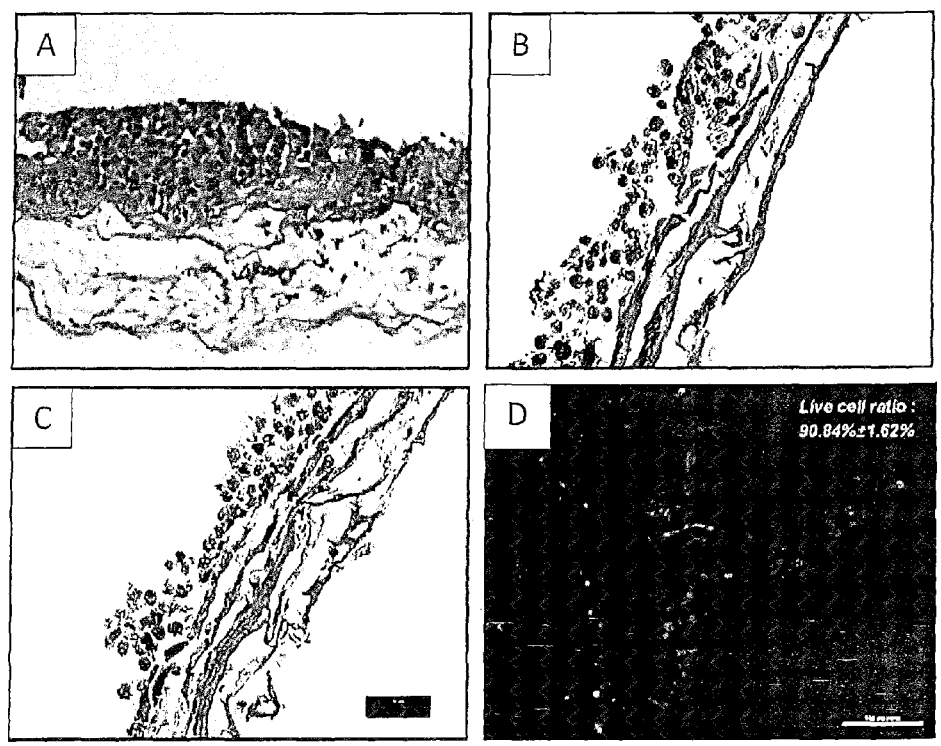
FIG. 23, comprising

Initial cell growth assays were performed using the HepG2 cell line. Although HepG2 cell proliferation was reduced when cells were grown on ECM discs decellularized with water and water+PAA wash methods compared to cells cultured on control (i.e. polystyrene culture plates and dishes coated with collagen type-I), HepG2 proliferation on ECM discs treated with the water wash significantly increased over time compared with the cells grown on the discs treated with PBS, PBS+PAA, salt, and salt+PAA ($p<0.01$) at each time point (FIG. 22). HepG2 cells formed multiple layers on the decellularized liver ECM. Cell-matrix penetration was observed when the cells were cultured on water-washed liver ECM decellularized under dynamic culture conditions (FIG. 23).

Based on these data, the water and water+PAA wash methods of decellularization were compared in studies with human hepatocytes. The water wash without PAA yielded better ECM discs for human hepatocyte growth. The number of hepatocytes remained stable when these cells were cultured on the water-washed ECM discs, while hepatocytes sometimes failed to grow on the ECM discs treated with the water+PAA method. Therefore, the water wash method was selected to generate the decellularized ECM discs for human hepatocyte cultures.

Figure 24:
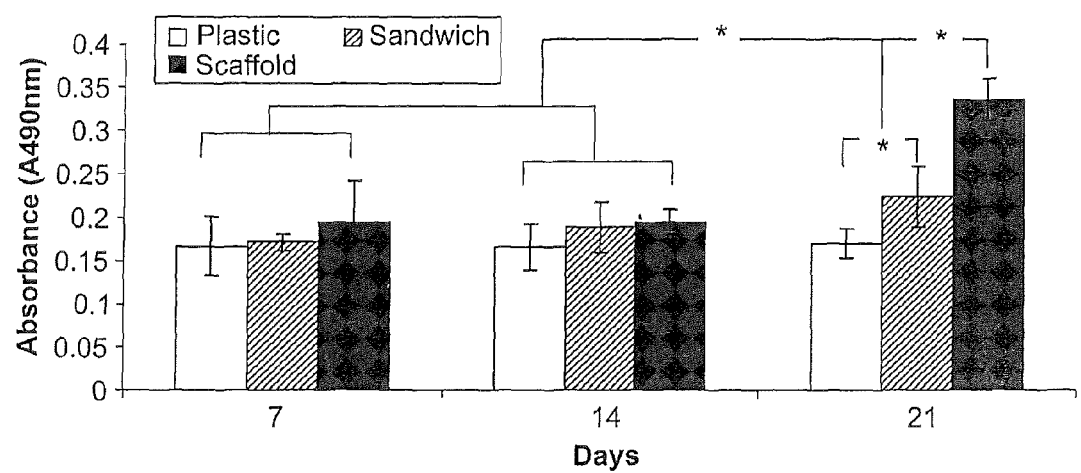
FIG. 24 is an image depicting the proliferation of human hepatocyte cultures on ECM discs prepared using the water decellularization method. MTS assay quantification of relative numbers of primary human hepatocytes cultured on plastic (open bars), in collagen sandwich cultures (striped bars), and on decellularized liver ECM discs (black bars) for up to 21 days. *=$p<0.05$.

To test the specific function of liver cells, human hepatocytes were cultured on either collagen gel sandwich cultures (positive control), polystyrene culture plates (negative control), or the liver ECM discs treated with the water wash method. Although the number of human primary hepatocytes did not obviously change over the first two weeks when the cells were cultured using all three culture conditions, at week 3, there were significantly more cells in the liver ECM disc cultures than the two controls (FIG. 24). In the two control groups, more cells were present in the collagen gel sandwich cultures compared to the polystyrene plates (FIG. 24). Although no cell-matrix penetration was noted, multiple layers of hepatocytes formed under static culture by day 21 (FIG. 23). A live/dead assay indicated that more than 90% of the hepatocytes were alive on the decellularized ECM discs (FIG. 23D).

Albumin Secretion of the Primary Human Hepatocytes

Figure 25:
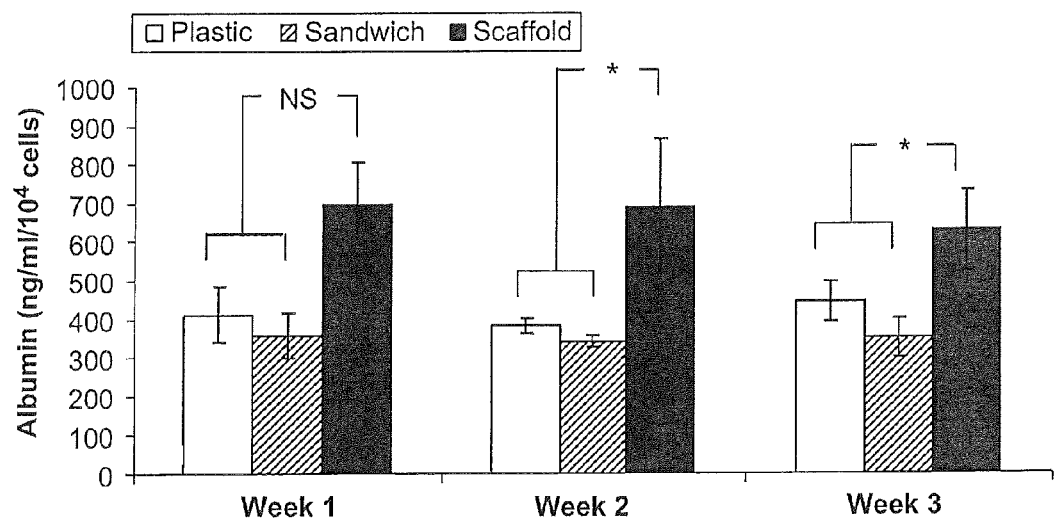
FIG. 25 is an image depicting albumin secretion of primary cultured human hepatocytes grown on liver ECM discs. Culture methods: plastic (open bars), collagen sandwich cultures (striped bars), and decellularized liver ECM discs (black bars). Albumin levels were measured in culture medium on days 7, 14, and 21 by ELISA and normalized to the number of human hepatocytes (MTS assay). NS=Not Significant, *=$p<0.05$.
Figure 26:
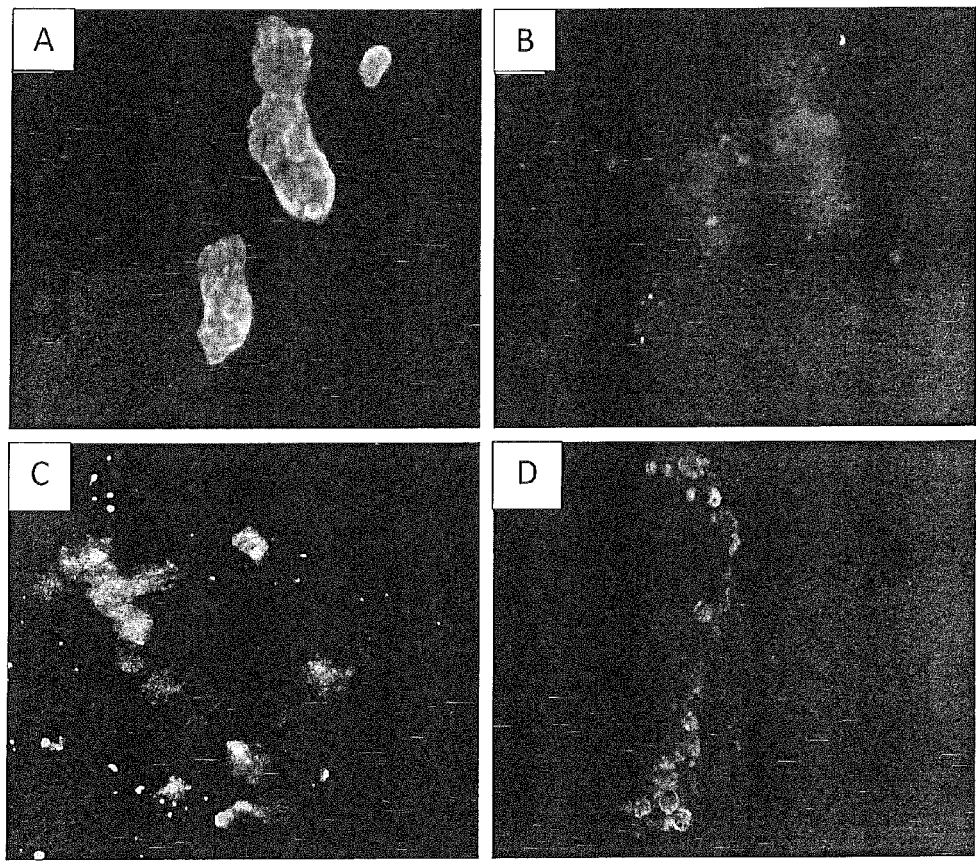
FIG. 26, comprising FIG. 26A through FIG. 26D shows immunofluorescence staining for albumin production by primary human hepatocytes grown on different matrices.

It is critically important to assess whether decellularized liver ECM discs can facilitate and maintain the specific function of primary cultured human hepatocytes in vitro. ELISA analysis showed that albumin secretion into culture medium significantly increased when hepatocytes were cultured on liver ECM discs compared to polystyrene plates and collagen gel sandwich cultures ($p<0.01$) (FIG. 25). Additionally, albumin levels remained stable for up to 3 weeks (FIG. 25). Albumin expression in human hepatocytes was confirmed with intense immunofluorescent staining in sandwich cultures and on liver ECM discs, but not in cells cultured on polystyrene dishes (FIG. 26).

A Micro-Scale System for Culture of Human Hepatocytes

The use of water wash followed by detergents during the decellularization procedure produced optimal liver ECM discs for cell growth, with uniform thicknesses and even surfaces. The water-decellularized ECM retained key liver ECM compounds such as collagens-I, -III and -IV, GAGs, fibronectin, and laminin. A final advantage of water-based decellularization is its cost-effectiveness. Those liver ECM compounds also prompted 3D cell growth of HepG2 cells under dynamic culture and supported the long-term maintenance of phenotype and function of human hepatocytes.

Numerous culture methods have been used or are under investigation for functional cell growth of primary hepatocyte in vitro. Polystyrene culture plates or dishes are most commonly used for cultures of HepG2 cells or primary human or animal hepatocytes. The collagen type-I gel sandwich culture method, in which the cells are cultured between two layers of collagen type-I gel, is considered the "gold standard" culture method for hepatocytes in vitro (Kono et al., 1997, In Vitro Cell Dev Biol Anim, 33:467-72; Peters et al., 2010, Cell Tissue Res, 340:451-7). Co-culturing of hepatocytes with other cell types such as sinusoidal cells (Bader et al., 1996, Exp Cell Res, 226:223-33), endothelial cells (Peters et al., 2010, Cell Tissue Res, 340:451-7; Gerlach et al., 2001, J Surg Res, 100:39-45), and fibroblasts (Cho et al., 2008, Biotechnol Bioeng, 101:345-56) has improved maintenance of liver cell function. In recent years, 3D matrices composed of natural collagen or synthetic biomaterials have been used for culture of hepatocytes (Hoshiba et al., 2006, Biomaterials, 27:4519-28; Mingoia et al., 2007, Toxicol in Vitro, 21:165-73; Park et al., 2006, J Biosci Bioeng, 101:238-42), and also liver tissue slices have been functionally maintained in culture (Amin et al., 2006, Toxicol Pathol, 34:776-84; Chang et al., 2009, J Viral Hepat, 16:359-66; Hart et al., 1983, In Vitro, 19:841-52). Although each of these techniques has advantages, none can satisfactorily maintain liver cell function long enough to assess chronic effects of toxicity. Therefore, for the purposes of high-throughput drug screening, it is critical to establish a novel culture system to maintain morphology and long-term function of human hepatocytes.

In the present study, gentle detergent and decellularization methods was selected to eliminate cellular compounds from thin liver tissue discs to preserve the native ECM molecular composition and architectures. The decellularization method was optimized to fabricate liver ECM derived from swine using six different methods. All six methods removed more than 93% of cellular compounds, but they preserved ECM components to a different degree. The water-based method resulted in scaffolds with the greatest collagen content and the least GAG content (when normalized to dry weight). Additionally, this method generated scaffolds that best maintained the disc size and shape, and preserved fibronectin, laminin, and elastin within the liver ECM. The PBS and salt wash methods reduced collagen content but preserved GAGs, similar to previous studies showing that liver ECM treated with salt solution preserved the maximum PGs/

GAGs (Rojkind et al., 1980, J Cell Biol, 87:255-63). Significantly, HepG2 cells had better growth on liver ECM treated with the water method than with PBS or salt methods.

Most importantly, 3D liver tissue-specific ECM discs fabricated with water-based decellularization showed growth and functional maintenance of primary human hepatocytes. Numbers of viable liver cells significantly increased using this method for 21 days of culture. The liver-specific functions in primary hepatocytes including albumin secretion, urea synthesis, CYP3A4 expression, or expression of tight junction associated proteins have commonly been used in drug development. In the present study, human hepatocytes showed significantly enhanced and sustained albumin secretion over a long time period when cultured on 3D liver tissue-specific ECM discs compared to the cells cultured on 2D polystyrene and collagen gel sandwich cultures. The inclusion of PAA treatment enhanced matrix porosity. Without wishing to be bound by any particular theory, it is believed that primary hepatocytes did not always grow on PAA-treated discs due to incomplete removal of PAA. Although previous studies demonstrated that bladder lamina propria or small intestine submucosa treated with 5% PAA increased matrix porosity and enhanced cell-matrix penetration with bladder smooth muscle cells, urothelial cells or urine-derived stem cells (Liu et al., 2009, Biomaterials, 30:3865-73; Wu et al., 2011, Biomaterials, 32:1317-26), liver cells appeared more sensitive to PAA treatment.

In this study, a micro-scale system for culture of human hepatocytes was developed. This methodology provides a simple and inexpensive means of producing a liver-specific ECM-based culture substrate that enhances hepatocyte growth and function compared to traditional 2D and collagen gel sandwich cultures. Data presented herein indicate that interactions of hepatocytes with 3D tissue-specific ECM improve cell attachment, survival, growth, and long-term viability of the highly functional phenotypes of liver cells. Due to the unique capabilities of liver-derived ECM, this culture system provides desirable cell-substrate interactions and also sustained cell proliferation while maintaining phenotype and function (McClelland et al., 2008, Tissue Eng Part A, 14:59-70). It is believed that these liver ECM scaffolds better represent the natural in vivo environment in an ex vivo system.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A tissue-specific in vitro cell culturing system for expanding a cell while maintaining cellular function, the cell culture system comprising:
   a cell;
   a culture medium; and
   a tissue-specific component;
   wherein said tissue-specific component comprises material isolated from a tissue that normally supports the growth and maturation of the cell in vivo by lyophilizing said tissue, grinding said lyophilized tissue and sterilizing said ground lyophilized tissue;
   wherein said tissue is a whole tissue; and
   wherein said isolated material is in the form of a ground lyophilized particle.

2. The cell culturing system of claim 1, wherein said whole tissue is a homogenate.

3. The cell culturing system of claim 1, wherein said cell is selected from the group consisting of an endothelial cell, a muscle cells, a smooth muscle cell, a fibroblast, an osteoblast, a myoblast, a neuroblast, a glioblast, a germ cell, a hepatocyte, a chondrocyte, a keratinocyte, a cardiac muscle cell, a connective tissue cell, an epithelial cell, a hormone-secreting cell, a cell of the immune system, a neuron, a stem cell, and any combination thereof.

4. The cell culturing system of claim 1, wherein said tissue is selected from the group consisting of heart, kidney, liver, lung, pancreas, spleen, bladder, cartilage, bone, brain, spine cord, peripheral nerve, ureter, urethra, and any combination thereof.

5. The cell culturing system of claim 1, further comprising a secreted factor selected from the group consisting of a growth factor, cytokine, and any combination thereof.

6. The cell culturing system of claim 1, wherein said tissue-specific component is in the form of a sterilized fine particle, wherein the particle size is less than about 40 µm.

7. The cell culturing system of claim 1, wherein said tissue-specific component is incorporated into a 2.5 D tissue particle coating.

8. The cell culturing system of claim 1, wherein said tissue-specific component is incorporated into a 3-D culture gel.

9. The cell culturing system of claim 1, wherein said tissue-specific component is incorporated into a 3-D porous tissue disc.

10. The cell culturing system of claim 1, wherein the tissue specific component further comprises a whole tissue extract supernatant.

11. The cell culturing system of claim 1, wherein said tissue-specific component comprises at least one selected from the group consisting of a tissue-specific whole tissue particle, a tissue-specific whole tissue particulate, and any combination thereof.

12. The cell culturing system of claim 11, wherein said tissue-specific component is incorporated with a biopolymer selected from the group consisting of type I collagen, hyaluronic acid, heparin-conjugated hyaluronic acid, and any combination thereof.

13. A method of maintaining cellular function of a cell cultured in vitro, the method comprising culturing a cell in an in vitro cell culturing system comprising a tissue-specific component isolated from a tissue of a mammal, wherein said tissue-specific component comprises material isolated from a tissue that normally supports the growth and maturation of said cell in vivo by lyophilizing said tissue, grinding said lyophilized tissue and sterilizing said ground lyophilized tissue;
   wherein said tissue is a whole tissue; and
   wherein said isolated material is in the form of a ground lyophilized particle.

14. The method of claim 13, wherein said whole tissue is a homogenate.

15. The method of claim 13, further comprising a cell selected from the group consisting of an endothelial cell, a muscle cells, a smooth muscle cell, a fibroblast, an osteoblast, a myoblast, a neuroblast, a glioblast, a germ cell, a hepatocyte, a chondrocyte, a keratinocyte, a cardiac muscle cell, a connective tissue cell, an epithelial cell, a hormone-secreting cell, a cell of the immune system, a neuron, a stem cell, and any combination thereof.

16. The method of claim 13, wherein said tissue is selected from the group consisting of heart, kidney, liver, lung, pancreas, spleen, bladder, cartilage, bone, brain, spine cord, peripheral nerve, ureter, urethra, and any combination thereof.

17. The method of claim 13, wherein said tissue-specific component further comprises a secreted factor selected from the group consisting of a growth factor, cytokine, and any combination thereof.

18. The method of claim 13, wherein said tissue-specific component is in the form of a sterilized fine particle, wherein the particle size is less than about 40 µm.

19. The method of claim 13, wherein said tissue-specific component is incorporated into a 2.5 D tissue particle coating.

20. The method of claim 13, wherein said tissue-specific component is incorporated into a 3-D culture gel.

21. The method of claim 13, wherein said tissue-specific component is incorporated into a 3-D porous tissue disc.

22. The method of claim 13, wherein the tissue specific component further comprises a whole tissue extract supernatant.

23. The method of claim 13, wherein said tissue-specific component comprises at least one selected from the group consisting of a tissue-specific whole tissue particle, a tissue-specific whole tissue particulate, and any combination thereof.

24. The method of claim 13, wherein said tissue-specific component is incorporated with a biopolymer selected from the group consisting of type I collagen, hyaluronic acid, heparin-conjugated hyaluronic acid, and any combination thereof.

25. A method of making tissue-specific extract for expanding a cell while maintaining cellular function, the method comprising:
    obtaining a tissue from a mammal;
    lyophilizing the tissue;
    powderizing the lyophilized tissue thereby generating a tissue-specific particle;
    forming a suspension comprising said tissue-specific particle by mixing the tissue-specific particle with a culture medium, hydrochloric acid and pepsin thereby generating a tissue-specific particle suspension;
    separating the tissue-specific particle suspension thereby generating a supernatant and a particulate, wherein the supernatant is a tissue-specific extract and wherein the particulate is a tissue-specific particulate; and
    isolating the tissue-specific extract from the particulate, and collecting the tissue-specific extract;
    wherein said tissue is a tissue selected from a whole tissue and a decellularized tissue.

26. A method of making a culture system for expanding a cell while maintaining cellular function, the method comprising:
    applying a tissue-specific component onto a surface, wherein said tissue-specific component comprises material isolated from a tissue that normally supports the growth and maturation of said cell in vivo by lyophilizing said tissue, grinding said lyophilized tissue and sterilizing said ground lyophilized tissue;
    wherein said tissue is a whole tissue; and
    wherein said tissue-specific component comprises at least one selected from the group consisting of a tissue-specific whole tissue particle, a tissue-specific whole tissue particulate, and any combination thereof.

27. A method of making a culture system for expanding a cell while maintaining cellular function, the method comprising:
    mixing a first solution comprising a tissue-specific component with a second solution comprising a biopolymer, thereby generating a hydrogel;
    wherein said tissue-specific component comprises material isolated from a tissue that normally supports the growth and maturation of said cell in vivo by lyophilizing said tissue, grinding said lyophilized tissue and sterilizing said ground lyophilized tissue;
    wherein said tissue is a whole tissue; and
    wherein said tissue-specific component comprises at least one selected from the group consisting of a tissue-specific whole tissue particle, a tissue-specific whole tissue particulate, and any combination thereof.

28. A tissue-specific in vitro cell culturing system for expanding a cell while maintaining cellular function, the cell culture system comprising:
    a cell;
    a culture medium; and
    a tissue-specific component;
    wherein said tissue-specific component comprises material isolated from a tissue that normally supports the growth and maturation of the cell in vivo by lyophilizing said tissue, grinding said lyophilized tissue and sterilizing said ground lyophilized tissue;
    wherein said tissue is selected from the group consisting of a whole tissue and a decellularized tissue;
    wherein said isolated material is in the form of a ground lyophilized particle; and
    wherein said tissue-specific component is incorporated with a biopolymer selected from the group consisting of hyaluronic acid, heparin-conjugated hyaluronic acid, and any combination thereof.

29. The cell culturing system of claim 28, wherein said tissue-specific component comprises material isolated from a whole tissue.

30. The cell culturing system of claim 29, wherein said whole tissue is a homogenate.

31. The cell culturing system of claim 28, wherein said tissue-specific component comprises material isolated from a decellularized tissue.

32. The cell culturing system of claim 31, wherein said decellularized tissue is a homogenate.

33. The cell culturing system of claim 28, wherein said cell is selected from the group consisting of an endothelial cell, a muscle cells, a smooth muscle cell, a fibroblast, an osteoblast, a myoblast, a neuroblast, a glioblast, a germ cell, a hepatocyte, a chondrocyte, a keratinocyte, a cardiac muscle cell, a connective tissue cell, an epithelial cell, a hormone-secreting cell, a cell of the immune system, a neuron, a stem cell, and any combination thereof.

34. The cell culturing system of claim 28, wherein said tissue is selected from the group consisting of heart, kidney, liver, lung, pancreas, spleen, bladder, cartilage, bone, brain, spine cord, peripheral nerve, ureter, urethra, and any combination thereof.

35. The cell culturing system of claim 28, further comprising a secreted factor selected from the group consisting of a growth factor, cytokine, and any combination thereof.

36. The cell culturing system of claim 28, wherein said tissue-specific component is in the form of a sterilized fine particle, wherein the particle size is less than about 40 µm.

37. The cell culturing system of claim 28, wherein said tissue-specific component is incorporated into a 3-D porous tissue disc.

38. The cell culturing system of claim 28, wherein said tissue-specific component is incorporated into a 3-D culture gel.

39. The cell culturing system of claim 28, wherein the tissue specific component further comprises a whole tissue extract supernatant.

40. The cell culturing system of claim 28, wherein said tissue-specific component comprises at least one selected from the group consisting of a tissue-specific whole tissue particle, a tissue-specific decellularized tissue particle, a tissue-specific whole tissue particulate, a tissue-specific decellularized tissue particulate, and any combination thereof.

41. A method of making a culture system for expanding a cell while maintaining cellular function, the method comprising:
    mixing a first solution comprising a tissue-specific component with a second solution comprising a biopolymer, thereby generating a hydrogel;
    wherein the biopolymer is selected from the group consisting of hyaluronic acid, heparin-conjugated hyaluronic acid, and any combination thereof;
    wherein said tissue-specific component comprises material isolated from a tissue that normally supports the growth and maturation of said cell in vivo by lyophilizing said tissue, grinding said lyophilized tissue and sterilizing said ground lyophilized tissue;
    wherein said tissue is selected from the group consisting of a whole tissue and a decellularized tissue; and
    wherein said tissue-specific component comprises at least one selected from the group consisting of a tissue-specific whole tissue particle, a tissue-specific decellularized tissue particle, a tissue-specific whole tissue particulate, a tissue-specific decellularized tissue particulate, and any combination thereof.

42. A method of maintaining cellular function of a cell cultured in vitro, the method comprising culturing a cell in an in vitro cell culturing system comprising a tissue-specific component isolated from a tissue of a mammal, wherein said tissue-specific component comprises material isolated from a tissue that normally supports the growth and maturation of said cell in vivo by lyophilizing said tissue, grinding said lyophilized tissue and sterilizing said ground lyophilized tissue;
    wherein said tissue is selected from the group consisting of a whole tissue and a decellularized tissue;
    wherein said isolated material is in the form of a ground lyophilized particle; and
    wherein said tissue-specific component is incorporated with a biopolymer selected from the group consisting of hyaluronic acid, heparin-conjugated hyaluronic acid, and any combination thereof.

43. The method of claim 42, wherein said tissue-specific component comprises material isolated from a whole tissue.

44. The method of claim 43, wherein said whole tissue is a homogenate.

45. The method of claim 42, wherein said tissue-specific component comprises material isolated from a decellularized tissue.

46. The method of claim 45, wherein said decellularized tissue is a homogenate.

47. The method of claim 42, further comprising a cell selected from the group consisting of an endothelial cell, a muscle cells, a smooth muscle cell, a fibroblast, an osteoblast, a myoblast, a neuroblast, a glioblast, a germ cell, a hepatocyte, a chondrocyte, a keratinocyte, a cardiac muscle cell, a connective tissue cell, an epithelial cell, a hormone-secreting cell, a cell of the immune system, a neuron, a stem cell, and any combination thereof.

48. The method of claim 42, wherein said tissue is selected from the group consisting of heart, kidney, liver, lung, pancreas, spleen, bladder, cartilage, bone, brain, spine cord, peripheral nerve, ureter, urethra, and any combination thereof.

49. The method of claim 42, wherein said tissue-specific component further comprises a secreted factor selected from the group consisting of a growth factor, cytokine, and any combination thereof.

50. The method of claim 42, wherein said tissue-specific component is in the form of a sterilized fine particle, wherein the particle size is less than about 40 µm.

51. The method of claim 42, wherein said tissue-specific component is incorporated into a 3-D culture gel.

52. The method of claim 42, wherein said tissue-specific component is incorporated into a 3-D porous tissue disc.

53. The method of claim 42, wherein the tissue specific component further comprises a whole tissue extract supernatant.

54. The method of claim 42, wherein said tissue-specific component comprises at least one selected from the group consisting of a tissue-specific whole tissue particle, a tissue-specific decellularized tissue particle, a tissue-specific whole tissue particulate, a tissue-specific decellularized tissue particulate, and any combination thereof.

* * * * *